United States Patent
Shim et al.

(10) Patent No.: US 12,024,710 B2
(45) Date of Patent: Jul. 2, 2024

(54) RECOMBINANT MICROORGANISM INCLUDING GENETIC MODIFICATION THAT INCREASES ACTIVITY OF NITROUS OXIDE REDUCTASE PATHWAY AND METHOD OF REDUCING CONCENTRATION OF NITROUS OXIDE IN SAMPLE BY USING THE SAME

(71) Applicant: Samsung Electronics Co., Ltd., Suwon-si (KR)

(72) Inventors: Woo Yong Shim, Hwaseong-si (KR); Seung Hoon Song, Suwon-si (KR); Jae-Young Kim, Suwon-si (KR); Dongsik Yang, Seoul (KR); Yu Kyung Jung, Hwaseong-si (KR)

(73) Assignee: SAMSUNG ELECTRONICS CO., LTD., Gyeonggi-Do (KR)

( * ) Notice: Subject to any disclaimer, the term of this patent is extended or adjusted under 35 U.S.C. 154(b) by 129 days.

(21) Appl. No.: 17/330,711

(22) Filed: May 26, 2021

(65) Prior Publication Data

US 2022/0177896 A1 Jun. 9, 2022

(30) Foreign Application Priority Data

Dec. 4, 2020 (KR) .......... 10-2020-0168728
Apr. 9, 2021 (KR) .......... 10-2021-0046578

(51) Int. Cl.
*C12N 1/20* (2006.01)
*C12N 15/52* (2006.01)
*C12R 1/185* (2006.01)

(52) U.S. Cl.
CPC .............. *C12N 15/52* (2013.01); *C12N 1/20* (2013.01); *C12R 2001/185* (2021.05); *C12Y 107/02004* (2013.01)

(58) Field of Classification Search
CPC ...... C12N 15/70; C12N 9/0004; C12N 15/63; C12P 1/04; C12Y 107/02
USPC .................. 435/252.3, 320.1, 69.1
See application file for complete search history.

(56) References Cited

FOREIGN PATENT DOCUMENTS

| CN | 111346482 A | 6/2020 |
|---|---|---|
| CN | 111534450 A | 8/2020 |
| JP | 1999075842 A | 3/1999 |

OTHER PUBLICATIONS

Davos et al., (Proteins: Structure, Function and Genetics, 2000, vol. 41: 98-107.*
Wristlock et al., (Quarterly Reviews of Biophysics 2003, vol. 36 (3): 307-340.*
Kwiatkowski et al., (Biochemistry 38:11643-11650, 1999.*
Kisselev L., (Structure, 2002, vol. 10: 8-9.*
Lin Zhang, et al., "Functional assembly of nitrous oxide reductase provides insights into copper site maturation," PNAS, Jun. 25, 2019 (Published online Jun. 12, 2019), vol. 116, No. 26, pp. 12822-12827.
Lin Zhang, et al., "The flavinyl transferase ApbE of Pseudomonas stutzeri matures the NosR protein required for nitrous oxide reduction," Biochimica et Biophysica Acta, Nov. 15, 2016, vol. 1858, pp. 95-102.
Rajkumari Kumaraswamy, et al., "Characterization of Microbial Communities Removing Nitrogen Oxides from Flue Gas: the BioDeNOx Process," Applied and Environmental Microbiology, Oct. 2005, vol. 71, No. 10, pp. 6345-6352.
Yu Wang, et al., "Gene cloning, expression, and reducing property enhancement of nitrous oxide reductase from Alcaligenes denitrificans strain TB," Environmental Pollution, 2018, vol. 239, pp. 43-52.

* cited by examiner

Primary Examiner — Robert B Mondesi
Assistant Examiner — Mohammad Y Meah
(74) Attorney, Agent, or Firm — CANTOR COLBURN LLP

(57) ABSTRACT

A recombinant microorganism of the genus *Escherichia*, comprises a genetic modification that increases expression of a nosZ gene encoding NosZ, which is a nitrous oxide reductase, in the recombinant microorganism, wherein the recombinant microorganism comprises a nosR gene encoding NosR, a nosD gene encoding NosD, a nosF gene encoding NosF, a nosY gene encoding NosY, and an apbE gene encoding ApbE, and wherein the nosR gene, the nosD gene, the nosF gene, the nosY gene and the apbE gene are derived from a microorganism of the genus *Pseudomonas*, the genus *Paracoccus*, or a combination thereof.

14 Claims, 5 Drawing Sheets
Specification includes a Sequence Listing.

RECOMBINANT MICROORGANISM INCLUDING GENETIC MODIFICATION THAT INCREASES ACTIVITY OF NITROUS OXIDE REDUCTASE PATHWAY AND METHOD OF REDUCING CONCENTRATION OF NITROUS OXIDE IN SAMPLE BY USING THE SAME

CROSS-REFERENCE TO RELATED APPLICATION

This application is based on and claims priority to Korean Patent Application No. 10-2020-0168728, filed on Dec. 4, 2020, and Korean Patent Application No. 10-2021-0046578, filed on Apr. 9, 2021, in the Korean Intellectual Property Office, and all the benefits accruing therefrom under 35 U.S.C. § 119, the contents of which in their entirety is herein incorporated by reference.

SEQUENCE LISTING

The present application contains a Sequence Listing which has been submitted electronically in ASCII format and is incorporated herein by reference in its entirety. Said ASCII copy, created on Jun. 16, 2023, is named "YPL2661US_ST25" and is 192,443 bytes in size. The Sequence Listing does not go beyond the disclosure of this application as filed.

BACKGROUND

1. Field

The present disclosure relates to a recombinant microorganism including a genetic modification that increases activity of a nitrous oxide reductase pathway, a composition including the recombinant microorganism for use in reducing a concentration of nitrous oxide in a sample, and a method of reducing a concentration of nitrous oxide in a sample.

2. Description of the Related Art

Nitrogen oxide (NOx) is an air pollutant emitted during a combustion process of fuels, and includes $N_2O$, $NO$, $N_2O_3$, $NO_2$, $N_2O_4$, $N_2O_5$, etc. Among the nitrogen oxides, NO and $NO_2$ mainly cause air pollution. $N_2O$, along with carbon dioxide ($CO_2$), methane ($CH_4$), and Freon gas (CFCs), absorbs and stores heat in the atmosphere, causing a greenhouse effect, and is one of the six major greenhouse gases regulated by the Kyoto Protocol. Its global warming potential (GWP) is 310, and the warming effect per unit mass is higher than that of carbon dioxide (1) and methane (21). In addition, nitrogen oxides are also the cause of smog and acid rain, and produce secondary fine particulate matter through chemical reactions in the air, as well as increased concentrations of ground-level ozone, which adversely affect respiratory health.

In a nitrogen oxide removal process, technologies such as selective catalytic reduction (SCR), selective non-catalytic reduction (SNCR), and/or scrubbing and adsorption, which are chemical reduction methods, are employed. Chemical methods have problems such as energy and catalyst costs, as well as treatment of secondary wastes generated therefrom. In addition, SCR or SNCR may generate $N_2O$, which is another greenhouse gas, as a result of incomplete reduction in the process of reducing NO and $N_2O$. Unlike chemical technologies, biological processes are environmentally friendly processes that have advantages such as relatively simple principles, no use of extreme conditions such as high temperature and high pressure, and low generation of secondary waste or wastewater. In a biological process, a microorganism acting as a biological catalyst may be used, instead of a chemical catalyst, to oxidize or reduce NOx or to fix it as a part of a cell.

However, there remains a need for an alternative biological denitrification method using a microorganism.

SUMMARY

Denitrifying bacteria reduce nitrogen oxide to $N_2$ through a dissimilatory reductive process. Recent studies have reported denitrifying bacteria such as *Pseudomonas putida, Pseudomonas denitrificans, Pseudomonas stutzeri, Paracoccus denitrificans,* and *Klebsiella pneumonia*. An alternative method such as a biological denitrification method using a recombinant microorganism based on a bacteria of the genus *Escherichia*, would be advantageous.

An aspect provides a recombinant microorganism including a genetic modification that increases expression of a gene in a nitrous oxide reductase pathway.

Another aspect provides a composition reducing a concentration of nitrous oxide in a sample, the composition including the recombinant microorganism including a genetic modification that increases expression of a gene in a nitrous oxide reductase pathway.

Still another aspect provides a method of reducing a concentration of nitrous oxide in a sample, the method including contacting the recombinant microorganism including a genetic modification that increases expression of a gene in a nitrous oxide reductase pathway to reduce the concentration of nitrous oxide in the sample.

Additional aspects will be set forth in part in the description which follows and, in part, will be apparent from the description, or may be learned by practice of the presented embodiments of the disclosure.

The term "increase in expression", as used herein, refers to a detectable increase in the expression of a given gene. The "increase in expression" means that a gene expression level in a genetically modified (e.g., genetically engineered) cell is greater than the expression level of a comparative cell of the same type that does not have a given genetic modification (e.g., original or "wild-type" cell). For example, a gene expression level of a genetically modified cell may be increased by about 5% or greater, about 10% or greater, about 15% or greater, about 20% or greater, about 30% or greater, about 50% or greater, about 60% or greater, about 70% or greater, or about 100% or greater than an expression level of a non-engineered cell of the same type, i.e., a wild-type cell or a parent cell. A cell having an increased expression of a protein or an enzyme may be identified by using any method known in the art.

The term "copy number increase" may be caused by introduction or amplification of a gene in a cell, and encompasses a cell which has been genetically modified to include a gene that does not naturally exist in a non-engineered cell. The introduction of the gene may be mediated by a vehicle such as a vector. The introduction of the gene may be a transient introduction in which the gene is not integrated into a genome of the cell, or an introduction that results in integration of the gene into the genome of the cell. The introduction may be performed, for example, by introducing a vector into the cell, the vector including a polynucleotide encoding a target polypeptide, and then, replicating the vector in the cell, or integrating the polynucleotide into the genome of the cell. The term "copy number increase" may be an increase the copy number of a gene or genes encoding one or more polypeptides constituting a complex, and which together, exhibit nitrous oxide reductase activity.

The introduction of the gene may be performed via a known method, such as transformation, transfection, or electroporation. The gene may be introduced with or without the use of a vehicle. The term "vehicle", as used herein, refers to a nucleic acid molecule that is able to deliver other nucleic acids linked thereto, to a cell. In view of a nucleic acid sequence mediating introduction of a specific gene, the term "vehicle" may be used interchangeably with a vector, a nucleic acid construct, or a cassette. The vector may include, for example, a plasmid vector, a virus-derived vector, but is not limited thereto. The plasmid includes a circular double-stranded DNA sequence to which additional DNA encoding a gene of interest, may be linked. The vector may include, for example, a plasmid expression vector (e.g., a bacterial plasmid), a virus expression vector, such as a replication-defective retrovirus, an adenovirus, an adeno-associated virus, or a combination thereof. In an aspect, the vector may be a bacterial plasmid including a bacterial origin of replication and selectable marker.

The genetic modification disclosed herein may be performed by any suitable molecular biological method known.

The term "parent cell" refers to an original cell prior to its genetic modification, for example, a non-genetically engineered cell of the same type as an engineered microorganism. With respect to a particular genetic modification, the "parent cell" may be a cell that lacks the particular genetic modification, but is identical in all other respects. Thus, the parent cell may be a cell that is used as a starting material to produce a genetically engineered microorganism having an increased expression level of a given protein (e.g., a protein having an amino acid sequence identity of about 75% or greater with respect to unmodified nitrous oxide reductase protein). The same comparison is also applied to other genetic modifications.

The term "gene", as used herein, refers to a polynucleotide encoding the information for expressing a particular protein, and may include or may not include a 5' non-coding regulatory sequence, a 3'-non-coding regulatory sequence, or a combination thereof.

The term "sequence identity" of a polynucleotide or a polypeptide, as used herein, refers to a degree of identity between nucleotides of a polynucleotide sequence or amino acid residues of a polypeptide sequences, and is obtained after the sequences are aligned so as to obtain a best match in certain comparable regions. The sequence identity is a value that is measured by comparing two sequences in certain comparable regions via optimal alignment of the two sequences, in which portions of the sequences in the certain comparable regions may be added or deleted compared to reference sequences. A percentage of sequence identity may be calculated by, for example, comparing two optimally aligned sequences in the entire comparable regions, determining the number of matching locations in which the same amino acids or nucleic acids appear, dividing the number of matching locations by the total number of locations in the compared regions (i.e., the size of a range), and multiplying the result of the division by 100 to obtain the percentage of the sequence identity. The percentage of the sequence identity may be determined using a known sequence comparison program, for example, BLASTn™ (NCBI), BLASTp™ (NCBI), CLC Main Workbench (CLC bio), or MegAlign™ (DNASTAR Inc).

The term "genetic modification", as used herein, refers to an artificial alteration in a constitution or structure of a genetic material of a cell.

An exogenous gene refers to a gene that is not naturally present in a cell and is introduced into the cell from the outside of the cell. The introduced exogenous gene may be homologous or heterologous with respect to the host cell type into which the gene is introduced. The term "heterologous" means "not native" or "foreign".

An aspect provides a recombinant microorganism of the genus *Escherichia*, including a genetic modification that increases expression of a nosZ gene encoding NosZ, which is a nitrous oxide reductase, in the recombinant microorganism, wherein the recombinant microorganism includes the nosZ gene, a nosR gene encoding NosR, a nosD gene encoding NosD, a nosF gene encoding NosF, a nosY gene encoding NosY, and an apbE gene encoding ApbE, and wherein the nosZ gene, the nosR gene, the nosD gene, the nosF gene, the nosY gene and the apbE gene are derived from a microorganism of the genus *Pseudomonas*, the genus *Paracoccus*, or a combination thereof.

The nitrous oxide reductase may be an enzyme that catalyzes a conversion reaction of $N_2O$ to $N_2$ using $N_2O$ as a substrate. The NosZ is a protein encoded by the nosZ gene, and is an enzyme (nitrous oxide reductase) that catalyzes a conversion reaction of $N_2O$ to $N_2$. The NosZ (e.g., NosZ protein) is a 130 kilodalton (kDa) homodimeric metalloprotein including two copper centers, $Cu_A$ and $Cu_Z$, in each monomer.

The NosR is a protein encoded by the nosR gene, and is a polytopic membrane protein that serves as an electron donor for $N_2O$ reduction. The NosD is a protein encoded by the nosD gene, and is essential for the formation of the [4Cu:2S] copper center $Cu_Z$ in the NosZ protein. In particular, the NosD provides sulfur (S) for NosZ. The NosF and NosY are proteins encoded by the nosF gene and the nosY gene, respectively. NosF and NosY together form a complex, e.g., a tetramer, which serves as an ABC transporter. The ApbE is a protein encoded by the apbE gene, and is a flavinyltransferase that transfers flavin to NosR.

The nitrous oxide may be in the form of Fe(II)(L)-NO. Fe(II)(L)-NO represents a complex formed by chelating a chelating agent L with $Fe^{2+}$ and NO. In the complex, the L may be, for example, ethylenediamine, diethylenetriamine, triethylenetetramine, hexamethylenetetraamine, N-(2-hydroxyethyl)ethylenediamine-triacetic acid (HEDTA), ethylenediamine-tetraacetic acid (EDTA), iminodiacetic acid, nitrilo-triacetic acid (NTA), or diethylenetriaminepentaacetic acid (DTPA). Therefore, Fe(II)(L)-NO may be in a form in which a nitrogen oxide such as $N_2O$, NO, $N_2O_3$, $NO_2$, $N_2O_4$ and $N_2O_5$ are modified to be soluble in an aqueous solution. Fe(II)(L)-NO may be formed by bringing a Fe(II)(L)-containing aqueous solution into contact with nitrogen oxide. The contacting may include mixing an aqueous medium with a liquid sample including liquid nitrogen oxide or bringing the aqueous medium into contact with a gaseous sample including gaseous nitrogen oxide. However, the recombinant microorganism is not limited to this specific mechanism in reducing a concentration of nitrous oxide in a sample.

The genetic modification may be a genetic modification that increases the copy number of the nosZ gene, the copy number of the nosR gene, the copy number of the nosD gene, the copy number of the nosF gene, the copy number of the nosY gene, and the copy number of the apbE gene. The genetic modification may include the introduction of the nosZ, nosR, nosD, nosF, nosY, and apbE genes, for example, via a vehicle such as a vector. The gene(s) may or may not be inserted within a chromosome (genome) of the recombinant microorganism. The introduced genes may include a plurality of copies of the genes, for example, a copy number of the genes may be, independently, 2 or greater, 5 or greater, 10 or greater, 25 or greater, 50 or greater, 100 or greater, or 1000 or greater.

The genes may be derived from a microorganism of the genus *Pseudomonas*. For example, the genes may be independently derived from *Pseudomonas stutzeri, Pseudomonas aeruginosa*, or a combination thereof.

The genes may be derived from a microorganism of the genus *Paracoccus*. For example, the genes may be derived from *Paracoccus versutus*.

The NosZ may be a polypeptide having 75% or greater sequence identity to the amino acid sequence of SEQ ID NO: 1, SEQ ID NO: 4, or SEQ ID NO: 7. The NosR may be a polypeptide having 75% or greater sequence identity to the amino acid sequence of SEQ ID NO: 10, SEQ ID NO: 13, or SEQ ID NO: 16. The NosD may be a polypeptide having 75% or greater sequence identity to the amino acid sequence of SEQ ID NO: 19, SEQ ID NO: 22, or SEQ ID NO: 25. The NosF may be a polypeptide having 75% or greater sequence identity to the amino acid sequence of SEQ ID NO: 28, SEQ ID NO: 31, or SEQ ID NO: 34. The NosY may be a polypeptide having 75% or greater sequence identity to the amino acid sequence of SEQ ID NO: 37, SEQ ID NO: 40, or SEQ ID NO: 43. The ApbE may be a polypeptide having 75% or more sequence greater to the amino acid sequence of SEQ ID NO: 55, SEQ ID NO: 58, or SEQ ID NO: 61.

The nosZ gene may have 75% or greater sequence identity to the nucleotide sequence of SEQ ID NO: 2, SEQ ID NO: 3, SEQ ID NO: 5, SEQ ID NO: 6, SEQ ID NO: 8, or SEQ ID NO: 9. The nosR gene may have 75% or greater sequence identity to the nucleotide sequence of SEQ ID NO: 11, SEQ ID NO: 12, SEQ ID NO: 14, SEQ ID NO: 15, SEQ ID NO: 17, or SEQ ID NO: 18. The nosD gene may have 75% or greater sequence identity to the nucleotide sequence of SEQ ID NO: 20, SEQ ID NO: 21, SEQ ID NO: 23, SEQ ID NO: 24, SEQ ID NO: 26, or SEQ ID NO: 27. The nosF gene may have 75% or greater sequence identity to the nucleotide sequence of SEQ ID NO: 29, SEQ ID NO: 30, SEQ ID NO: 32, SEQ ID NO: 33, SEQ ID NO: 35, or SEQ ID NO: 36. The nosY gene may have 75% or greater sequence identity to the nucleotide sequence of SEQ ID NO: 38, SEQ ID NO: 39, SEQ ID NO: 41, 42, SEQ ID NO: 44, or SEQ ID NO: 45. The ApbE gene may have 75% or greater sequence identity to the nucleotide sequence of SEQ ID NO: 56, SEQ ID NO: 57, SEQ ID NO: 59, SEQ ID NO: 60, SEQ ID NO: 62, or SEQ ID NO: 63.

With regard to the recombinant microorganism, each of the nosZ gene, the nosR gene, the nosD gene, the nosF gene, the nosY gene, and the apbE gene may be introduced into the recombinant microorganism via at least one vector. The vector may be present outside a chromosome of the recombinant microorganism (e.g., not incorporated/integrated in a chromosome of the recombinant microorganism).

With regard to the recombinant microorganism, the nosZ gene and the nosR gene may be included in a first vector, and the nosD gene, the nosF gene, the nosY gene, and the apbE gene may be included in a second vector. The second vector including the nosD gene, the nosF gene, the nosY gene, and the apbE gene may be different from the first vector including the nosZ gene and the nosR gene.

With regard to the recombinant microorganism, the nosZ gene and the nosR gene may be included in a first operon, the nosD gene and the nosF gene may be included in a second operon, the nosY gene and the apbE may be included in a third operon, and the nosD gene, the nosF gene, and the nosY gene may be included in a fourth operon. The first operon including the nosZ gene and the nosR gene, the second operon including the nosD gene and the nosF gene, the third operon including the nosY gene and the apbE, and the fourth operon including the nosD gene, nosF gene, and nosY gene may be included in vectors which are different from each other.

In an aspect, an exogenous nosL gene encoding a heterologous NosL may not be present in the recombinant microorganism. In an exemplary embodiment of the present disclosure, the NosL may be a polypeptide having 75% or greater sequence identity to the amino acid sequence of SEQ ID NO: 46, SEQ ID NO:49, or SEQ ID NO:52. The nosL gene may have 75% or greater sequence identity to the nucleotide sequence of SEQ ID NO: 47, SEQ ID NO:48, SEQ ID NO:50, SEQ ID NO:51, SEQ ID NO:53, or SEQ ID NO:54.

In the present disclosure, the vector includes the tatA gene encoding TatA, the tatB gene encoding TatB, the tatC gene encoding TatC, or a combination thereof. The TatA, TatB, or TatC may be a polypeptide having 75% or greater sequence identity to the amino acid sequence of SEQ ID NO: 64, SEQ ID NO:67, SEQ ID NO:70, SEQ ID NO:73, SEQ ID NO:76, SEQ ID NO:79, SEQ ID NO:82, SEQ ID NO:85, or SEQ ID NO:88. The tatA, tatB, or tatC gene may have 75% or greater sequence identity to the nucleotide sequence of SEQ ID NO: 65, SEQ ID NO: 66, SEQ ID NO:68, SEQ ID NO:69, SEQ ID NO:71, SEQ ID NO:72, SEQ ID NO:74, SEQ ID NO:75, SEQ ID NO:77, SEQ ID NO:78, SEQ ID NO:80, SEQ ID NO:81, SEQ ID NO:83, SEQ ID NO:84, SEQ ID NO:86, SEQ ID NO:87, SEQ ID NO:89, or SEQ ID NO:90.

The recombinant microorganism may be a microorganism of the genus *Escherichia*, for example, *E. coli*.

The recombinant microorganism may reduce a concentration of nitrous oxide in a sample. The reduction may include converting $N_2O$ or $Fe(II)(L)$-NO to $N_2$ by the nitrous oxide reductase. The sample may be in a liquid or gas state. The sample may be industrial wastewater or waste gas. The sample may be any sample, as long as it includes a nitrogen oxide such as nitrous oxide. The nitrogen oxide may include $N_2O$, NO, $N_2O_3$, $NO_2$, $N_2O_4$, $N_2O_5$, or a combination thereof.

Another aspect provides a composition reducing a concentration of nitrous oxide in a sample, the composition including the recombinant microorganism of the genus *Escherichia* including a genetic modification that increases expression of a nosZ gene encoding NosZ, which is a nitrous oxide reductase, wherein the recombinant microorganism comprises the nosZ gene, a nosR gene encoding NosR, a nosD gene encoding NosD, a nosF gene encoding NosF, a nosY gene encoding NosY, and an apbE gene encoding ApbE, and wherein the nosZ gene, the nosR gene, the nosD gene, the nosF gene, the nosY gene and the apbE gene are derived from a microorganism of the genus *Pseudomonas*, the genus *Paracoccus*, or a combination thereof.

With regard to the composition, the recombinant microorganism, the sample, and the nitrous oxide are the same as described above.

With regard to the composition, the term "reducing" refers to reduction of a concentration of nitrous oxide present in a sample, and may include a complete removal of the nitric oxide from the sample. The sample may be a gas or a liquid. The sample may not naturally include the recombinant microorganism. The composition may further include a substance that increases the solubility of nitrous oxide in a medium or a culture. The nitrous oxide may be in the form of Fe(II)(L)-NO.

The composition may be used for reducing a concentration of nitrogen oxide in a sample by contacting the composition with the sample. The contacting may be performed in a liquid phase. The contacting may be performed by, for example, bringing a culture including the recombinant microorganism cultured in a culture medium into contact with the sample. The contacting may be performed under conditions in which the microorganism grows. The contacting may be performed in a sealed container. The contacting may be performed under anaerobic conditions. The contacting may include culturing or incubating the recombinant microorganism in the presence of the nitrogen oxide-containing sample. The contacting includes culturing the recombinant microorganism in a sealed container and under conditions in which the recombinant microorganism grows.

The culture medium may be a chemically defined medium. As used herein, "chemically defined medium" refers to a medium in which the chemical composition is known. The chemically defined medium may be a medium that does not include a complex component, such as serum or a hydrolysate. The liquid medium may include, for example, an LB medium, an M9 medium, a phosphate buffer, or a Tris buffer. The medium may include $Mg^{2+}$ ions at a concentration of about 0.1 millimolar (mM) to about 7.5 mM, about 0.5 mM to about 7.5 mM, about 0.5 mM to about 5.0 mM, about 0.5 mM to about 2.5 mM, about 0.5 mM to about 1.5 mM, or about 1.0 mM to about 2.5 mM.

Still another aspect provides a method of reducing a concentration of nitrous oxide in a sample, the method including contacting the recombinant microorganism of the genus *Escherichia* with the nitrous oxide-containing sample, wherein the recombinant microorganism is of the genus *Escherichia* and includes a genetic modification that increases expression of a nosZ gene encoding NosZ, which is a nitrous oxide reductase, wherein the recombinant microorganism includes the nosZ gene, a nosR gene encoding NosR, a nosD gene encoding NosD, a nosF gene encoding NosF, a nosY gene encoding NosY, and an apbE gene encoding ApbE, wherein the nosZ gene, the nosR gene, the nosD gene, the nosF gene, the nosY gene, and the apbE gene are which are derived from a microorganism of the genus *Pseudomonas* or *Paracoccus*.

With regard to the method, the recombinant microorganism and the nitrous oxide-containing sample are the same as described above.

With regard to the method, the contacting may be performed in a liquid phase. The contacting may be performed by, for example, bringing a culture of the recombinant microorganism cultured in the medium into contact with the sample. The contacting may be performed under conditions where the recombinant microorganism grows. The contacting may be performed in a sealed container. The medium may be a chemically defined medium. The chemically defined medium may be a medium that does not include a complex component such as serum or a hydrolysate. The liquid medium may include an LB medium, an M9 medium, a phosphate buffer, and a Tris buffer. The medium may include $Mg^{2+}$ ions in a concentration of about 0.1 mM to about 7.5 mM, about 0.5 mM to about 7.5 mM, about 0.5 mM to about 5.0 mM, about 0.5 mM to about 2.5 mM, about 0.5 mM to about 1.5 mM, or about 1.0 mM to about 2.5 mM.

The contacting may be performed when the growth of the recombinant microorganism is an exponential phase or a stationary phase. The culturing may be performed under anaerobic conditions. The contacting may be performed in a sealed container and under conditions in which the recombinant microorganism may be viable. The conditions, where the recombinant microorganism may be viable, may be conditions where the recombinant microorganism is capable of proliferating and/or allowed to proliferate.

With regard to the method, the sample may be in a liquid or gas state. The sample may be industrial wastewater or waste gas. The sample may be actively or passively brought into contact with the culture of the recombinant microorganism. The sample may be, for example, sparged into the culture of the recombinant microorganism. In other words, the sample may be blown through the medium or the culture. The sparging may include blowing of the sample from the bottom to the top of the medium or the culture of the recombinant microorganism. The sparging may include injecting of droplets of the sample.

With regard to the method, the contacting may be performed in a batch or continuous manner. The contacting may further include, for example, bringing the reduced sample, i.e., the contacted sample obtained in the reducing, into contact with a fresh recombinant microorganism including the genetic modification that increases expression of the nosZ gene encoding NosZ, which is a nitrous oxide reductase, and which includes the nosZ gene, a nosR gene encoding NosR, a nosD gene encoding NosD, a nosF gene encoding NosF, a nosY gene encoding NosY, and an apbE gene encoding ApbE, wherein the nosZ gene, the nosR gene, the nosD gene, the nosF gene, the nosY gene and the apbE gene are derived from a microorganism of the genus *Pseudomonas*, the genus *Paracoccus*, or a combination thereof. The contacting of the reduced sample with the fresh recombinant microorganism may be performed two times or greater, for example, three times, five times, or ten times or greater. The contacting may be repeated until the concentration of nitrous oxide in the sample reaches a desired minimum concentration.

Still another aspect provides a method of preparing a recombinant microorganism, the method including introducing a genetic modification that increases expression of a nosZ gene encoding NosZ, which is a nitrous oxide reductase, into a microorganism of the genus *Escherichia*, wherein the genetic modification includes introduction of the nosZ gene, a nosR gene encoding NosR, a nosD gene encoding NosD, a nosF gene encoding NosF, a nosY gene encoding NosY, and an apbE gene encoding ApbE into the microorganism of the genus *Escherichia*, wherein the nosZ gene, the nosR gene, the nosD gene, the nosF gene, the nosY gene and the apbE gene are derived from a microorganism of the genus *Pseudomonas*, the genus *Paracoccus*, or a combination thereof. The method may be a method of preparing a microorganism, the method including introducing the genes into the microorganism. The introducing of the genes may be introducing of vehicles including the genes into the microorganism.

A recombinant microorganism according to an aspect may be used in removing nitrous oxide in a sample.

A composition according to another aspect may be used in reducing a concentration of nitrous oxide in a sample.

A method of reducing a concentration of nitrous oxide in a sample according to still another aspect may efficiently reduce the concentration of nitrous oxide in the sample.

BRIEF DESCRIPTION OF THE DRAWINGS

The above and other aspects, features, and advantages of certain embodiments of the disclosure will be more apparent from the following description taken in conjunction with the accompanying drawings, in which.

DETAILED DESCRIPTION

Figure 1A:
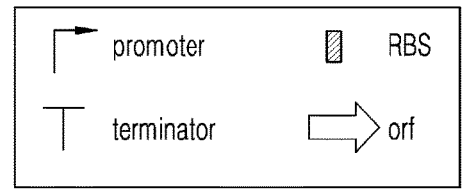
FIG. 1A is an illustration of a norVW gene in the chromosome of E. coli.
Figure 1A:
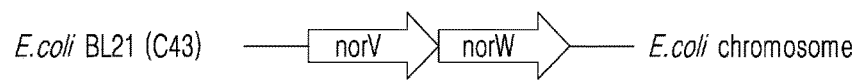

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects.

The terminology used herein is for the purpose of describing particular embodiments only and is not intended to be limiting. "At least one" is not to be construed as limiting "a" or "an." As used herein, "a," "an," "the," and "at least one" do not denote a limitation of quantity, and are intended to cover both the singular and plural, unless the context clearly indicates otherwise. For example, "an element" has the same meaning as "at least one element," unless the context clearly indicates otherwise. "Or" means "and/or." As used herein, the term "and/or" includes any and all combinations of one or more of the associated listed items. It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

"About" or "approximately" as used herein is inclusive of the stated value and means within an acceptable range of deviation for the particular value as determined by one of ordinary skill in the art, considering the measurement in question and the error associated with measurement of the particular quantity (i.e., the limitations of the measurement system). For example, "about" can mean within one or more standard deviations, or within ±30%, 20%, 10% or 5% of the stated value.

Unless otherwise defined, all terms (including technical and scientific terms) used herein have the same meaning as commonly understood by one of ordinary skill in the art to which this disclosure belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein, Hereinafter, the present disclosure will be described in more detail with reference to exemplary embodiments. However, these exemplary embodiments are only for illustrating the present disclosure, and the scope of the present disclosure is not limited to these exemplary embodiments.

Example 1: Development of Recombinant Microorganism of Genus Escherichia Having $N_2$-Producing Ability In this exemplary embodiment, a nosZ gene encoding a key enzyme nitrous oxide reductase (NosZ) and the accessory genes essential for activity of the NosZ enzyme, i.e., nosR, nosL, nosD, nosF, nosY, apbE, and tat genes, were extracted from nos operons or gene clusters and genomes of three kinds of natural denitrifying bacteria: Pseudomonas stutzeri, Pseudomonas aeruginosa, and Paracoccus versutus. Each of the genes was codon-optimized for E. coli, and then introduced into E. coli. As a result, a recombinant microorganism of the genus Escherichia having $N_2$-producing ability by converting $N_2O$ to $N_2$, i.e., a recombinant E. coli, was prepared. To examine whether the recombinant E. coli had the $N_2$-producing ability, the recombinant E. coli was cultured in the presence of a substrate containing a radioactive isotope $^{15}N$, i.e., $^{15}N_2O$ and FeEDTA-$^{15}NO$, and then the amount of $^{15}N_2$ in the culture or in the upper air layer in the culture, was measured.

1. Identification of Genes Essential for Conversion of In Vivo $N_2O$ to $N_2$ in E. coli In detail, 8 different genes, i.e., nosZ, nosR, nosL, nosD, nosF, nosY, apbE, and tat genes, which exist in nitrous oxide reductase clusters of natural denitrifying bacteria of the genus Pseudomonas and the genus Paracoccus, e.g., Pseudomonas stutzeri (Ps), Pseudomonas aeruginosa (Pa), and Paracoccus versutus (Pv), were introduced in combination into E. coli to obtain recombinant E. coli. Next, the 6 different genes essential for the ability of the recombinant E. coli to convert in vivo $N_2O$ to $N_2$, e.g., nosZ, nosR, nosD, nosF, nosY, and apbE genes, were determined by examining the ability of the obtained recombinant E. coli to convert in vivo $N_2O$ to $N_2$.

The functions of the respective gene products are considered to be as follows. NosZ is a protein encoded by the nosZ gene, and is an enzyme that catalyzes a conversion reaction of $N_2O$ to $N_2$, i.e., nitrous oxide reductase. NosZ is a 130 kDa, homodimeric metalloprotein including two copper centers, i.e., $Cu_A$ and $Cu_Z$, in each monomer. NosR is a protein encoded by the nosR gene, and may be a polytopic membrane protein that serves as an electron donor for $N_2O$ reduction. NosD is a protein encoded by the nosD gene, and is essential for the formation of the [4Cu:2S] site $Cu_Z$ of the NosZ protein. NosD may provide sulfur (S) for NosZ. NosF and NosY are proteins encoded by the nosF gene and the nosY gene, respectively, and NosF and NosY together form a complex, e.g., a tetramer, to serve as an ABC transporter. ApbE is a protein encoded by the apbE gene, and may be a flavinyltransferase that transfers flavin to NosR.

2. Construction of Vector and Preparation of Recombinant *E. coli* Transformed with this Vector (1) Construction of Vector Expression vectors used in this exemplary embodiment were pET28a, pETDuet™-1, and pACYCDuet™-1 vectors. pET28a, in which a lac operator is operably linked to a T7 promoter, includes a kanamycin resistance $Kan^R$ gene as a selection marker. pETDuet™-1 vector, in which a lac operator is operably linked to a T7 promoter, includes an ampicillin resistance $Amp^R$ gene as a selection marker. pACYC-Duet™1 vector, in which a lac operator is operably linked to a T7 promoter, includes a chloramphenicol resistance $Cm^R$ gene as a selection marker.

The NosZ has the amino acid sequence of SEQ ID NO: 1, SEQ ID NO: 4, or SEQ ID NO: 7. The NosR has the amino acid sequence of SEQ ID NO: 10, SEQ ID NO: 13, or SEQ ID NO: 16. The NosD has the amino acid sequence of SEQ ID NO: 19, SEQ ID NO: 22, or SEQ ID NO: 25. The NosF has the amino acid sequence of SEQ ID NO: 28, SEQ ID NO: 31, or SEQ ID NO: 34. The NosY has the amino acid sequence of SEQ ID NO: 37, SEQ ID NO: 40, or SEQ ID NO: 43. The ApbE has the amino acid sequence of SEQ ID NO: 55, SEQ ID NO: 58, or SEQ ID NO: 61.

Further, the nosZ gene has the nucleotide sequence of SEQ ID NO: 2, SEQ ID NO: 3, SEQ ID NO: 5, SEQ ID NO: 6, SEQ ID NO: 8, or SEQ ID NO: 9. The nosR gene has the nucleotide sequence of SEQ ID NO: 11, SEQ ID NO: 12, SEQ ID NO: 14, 15, SEQ ID NO: 17, or SEQ ID NO: 18. The nosD gene has the nucleotide sequence of SEQ ID NO: 20, SEQ ID NO: 21, SEQ ID NO: 23, SEQ ID NO: 24, SEQ ID NO: 26, or SEQ ID NO: 27. The nosF gene has the nucleotide sequence of SEQ ID NO: 29, SEQ ID NO: 30, SEQ ID NO: 32, SEQ ID NO: 33, SEQ ID NO: 35, or SEQ ID NO: 36. The nosY gene has the nucleotide sequence of SEQ ID NO: 38, SEQ ID NO: 39, SEQ ID NO: 41, SEQ ID NO: 42, SEQ ID NO: 44, or SEQ ID NO: 45. The ApbE gene has the nucleotide sequence of SEQ ID NO: 56, SEQ ID NO: 57, SEQ ID NO: 59, SEQ ID NO: 60, SEQ ID NO: 62, or SEQ ID NO: 63. Further, the NosL has the amino acid sequence of SEQ ID NO: 46, SEQ ID NO: 49, or SEQ ID NO: 52. The nosL gene has the nucleotide sequence of SEQ ID NO: 47, SEQ ID NO: 48, SEQ ID NO: 50, SEQ ID NO: 51, SEQ ID NO: 53, or SEQ ID NO: 54.

Further, the tatA, tatB, or tatC has the amino acid sequence of SEQ ID NO:64, SEQ ID NO: 67, SEQ ID NO: 70, SEQ ID NO: 73, SEQ ID NO: 76, SEQ ID NO: 79, SEQ ID NO: 82, SEQ ID NO: 85, or SEQ ID NO: 88. The tatA, tatB, or tatC gene has the nucleotide sequence of SEQ ID NO: 65, SEQ ID NO: 66, SEQ ID NO: 68, SEQ ID NO: 69, SEQ ID NO: 71, SEQ ID NO: 72, SEQ ID NO: 74, SEQ ID NO: 75, SEQ ID NO: 77, SEQ ID NO: 78, SEQ ID NO: 80, SEQ ID NO: 81, SEQ ID NO: 83, SEQ ID NO: 84, 86, SEQ ID NO: 87, SEQ ID NO: 89, or SEQ ID NO: 90.

The origin and characteristics of the above-mentioned proteins and nucleotides encoding the same are listed in the sequence list. Among the above genes, genes used in the expression vector of *E. coli* in this exemplary embodiment were those optimized by considering the codon frequency used in *E. coli* for the nucleotide sequence of a natural gene, and information thereof is described in the sequence list.

Figure 1B:
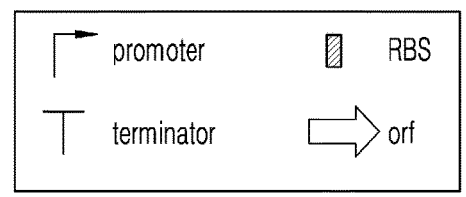
FIG. 1B is a map of a pPs2/Pa2/Pv2 vector.
Figure 1B:
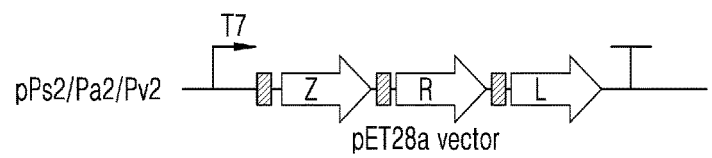

FIG. 1A shows a norVW site in the chromosome of *E. coli* and maps of the pPs2/Pa2/Pv2 vector and the pPs4/Pa4/Pv4 vector introduced into *E. coli*. In FIG. 1A, norVW indicates nitrous oxide reductase of *E. coli*. In FIG. 1B pPs2/Pa2/Pv2 vector, nosZ (Z), nosR (R) and nosL (L) genes, derived from *P. stutzeri*, *P. aeruginosa*, and *P. versutus*, were commonly operably linked to a T7 promoter in pET28a vector, and a ribosome binding site (RBS) indicates an AAGGAG sequence, which is an *E. coli* RBS sequence. In this regard, the nosZ gene includes a sequence encoding his-tag.

The nosZ, nosR, and nosL genes were amplified from three different strains of microorganisms by PCR using primer sets and using DNA synthesized by codon optimization as a template, and the resulting products were introduced into the vector at an NcoI enzyme restriction site. For the nosZ, nosR, and nosL genes of *P. stutzeri*, primer sets of SEQ ID NOs: 91 and 92; SEQ ID NOs: 93 and 94; and SEQ ID NOs: 95 and 96 were used, respectively. For the nosZ, nosR and nosL genes of *P. aeruginosa*, primer sets of SEQ ID NOs: 97 and 98; SEQ ID NOs: 99 and 100; and SEQ ID NOs: 101 and 102 were used, respectively. For the nosZ, nosR and nosL genes of *P. versutus*, primer sets of SEQ ID NOs: 103 and 104; SEQ ID NOs: 105 and 106; and SEQ ID NOs: 107 and 108 were used, respectively.

Figure 1C:
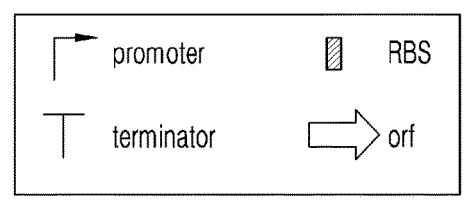
FIG. 1C is a map of a pPs4/Pa4/Pv4 vector.
Figure 1C:
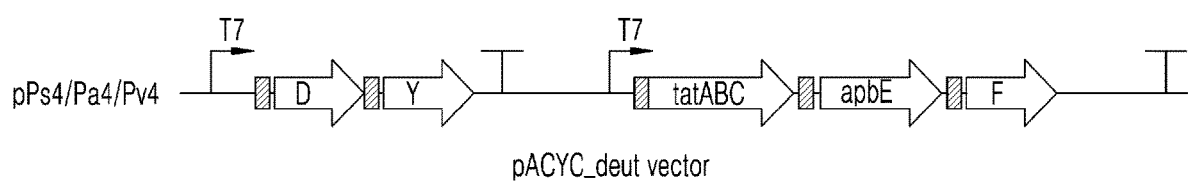

In FIG. 1C, the pPs4/Pa4/Pv4 vector, nosD and nosY genes, derived from *P. stutzeri*, *P. aeruginosa*, or *P. versutus*, were commonly operably linked to a T7 promoter in a pACYC-duet vector, tatABC, apbE, and nosF genes are commonly operably linked to another T7 promoter, and RBS of each gene indicates an *E. coli* RBS AAGGAG sequence. The nosD, nosY, tatABC, apbE, and nosF genes from each of three strains of microorganisms were amplified by PCR using the following primer sets and DNA synthesized by codon optimization as a template. The resulting PCT products of the nosD and nosY genes were introduced into an NcoI enzyme restriction site, and the resulting products of the tatABC, apbE, and nosF genes were introduced into an NdeI enzyme restriction site. For the nosD, nosY, tatABC, apbE, and nosF genes of *P. stutzeri*, primer sets of SEQ ID NOs: 109 and 110; SEQ ID NOs: 111 and 112; SEQ ID NOs: 113 and 114; SEQ ID NOs: 115 and 116; and SEQ ID NOs: 117 and 118 were used, respectively. For the nosD, nosY, tatABC, apbE, and nosF genes of *P. aeruginosa*, primer sets of SEQ ID NOs: 119 and 120; SEQ ID NOs: 121 and 122; SEQ ID NOs: 123 and 124; SEQ ID NOs: 125 and 126; and SEQ ID NOs: 127 and 128 were used, respectively. For the nosD, nosY, tatABC, apbE, and nosF genes of *P. versutus*, primer sets of SEQ ID NOs: 129 and 130; SEQ ID NOs: 131 and 132; SEQ ID NOs: 133 and 134; SEQ ID NOs: 135 and 136; and SEQ ID NOs: 137 and 138 were used, respectively. The tatABC of *P. stutzeri*, *P. aeruginosa*, and *P. versutus* is a codon-optimized sequence including all of the tatA, tatB, and tatC genes, and has the nucleotide sequence of SEQ ID NO: 139, 140, or 141.

Further, in FIG. 1, each vector excluding the nosL gene or the nosR gene from pPs2/Pa2/Pv2, and each vector excluding the nosY gene, the tatABC gene, and the apbE gene; the tatABC gene, the apbE gene, and the nosF gene; the tatABC gene and the apbE gene; or the tatABC gene from pPs4/Pa4/Pv4, were prepared. One vector was selected from the pPs2/Pa2/Pv2-based vectors, and one vector was selected from the pPs4/Pa4/Pv4-based vectors, and these two vectors were introduced into *E. coli* such that gene combinations selected from the eight genes were expressed in the recombinant *E. coli*. The recombinant *E. coli* including these gene combinations was cultured in the presence of $N_2O$ or Fe(II)EDTA-NO, and the $N_2$-producing ability thereof was examined to identify gene combinations essential for $N_2$ production in *E. coli*. Here, with regard to apbE, one kind of P. stutzeri (Ps), i.e., Ps_apbE, one kind of P. aeruginosa (Pa), i.e., Pa_apbE, and one kind of P. versutus (Pv), i.e., Pv_apbE were introduced.

Figure 2:
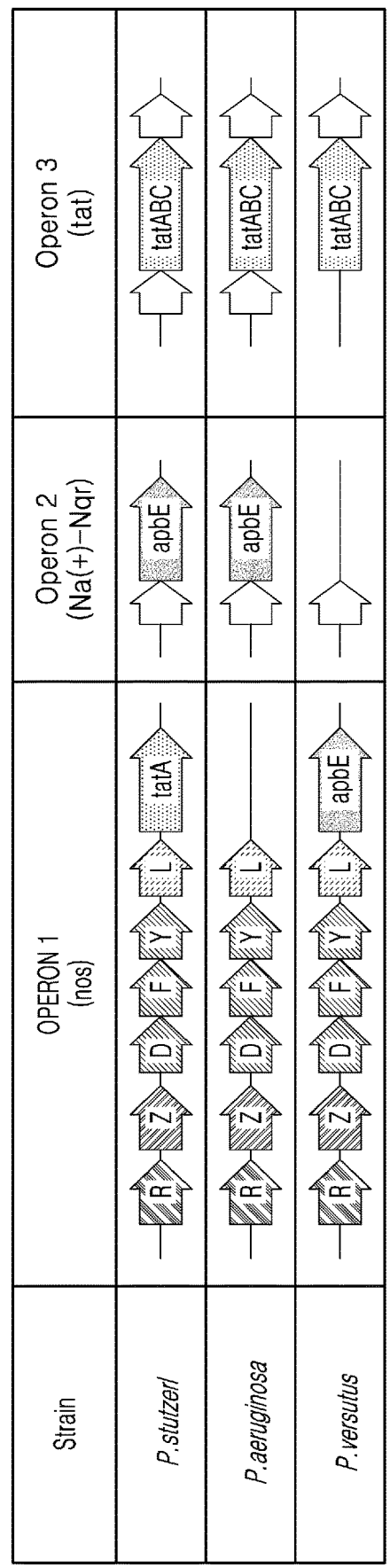
FIG. 2 illustrates the genetic maps of the nitrous oxide reductase pathways of P. stutzeri, P. aeruginosa, and P. versutus.

FIG. 2 shows the genetic maps of the nitrous oxide reductase pathways of P. stutzeri, P. aeruginosa, and P. versutus.

(2) Preparation of Recombinant E. coli Having $N_2$-Producing Ability and Examination of Activity Thereof Two vectors consisting of one vector of the pPs2/Pa2/Pv2-based vectors and one vector of pPs4/Pa4/Pv4-based vectors prepared in (1) were introduced into E. coli strain C43 (DE3) by transformation to prepare recombinant E. coli. The transformation was performed by electroporation. In this regard, each gene introduced into E. coli was a gene derived from the same strain.

(2.1) Culture for NosZ Maturation Stage

The recombinant E. coli was cultured at 37° C. in a 2×YT medium containing 50 micrograms per milliliter (μg/mL) riboflavin and 0.25 mM $CuCl_2$ in an Erlenmeyer flask until the $OD_{600}$ of the culture reached 0.6, and then 1 mM isopropyl β-D-1-thiogalactopyranoside (IPTG) was added and the bacteria were cultured at 30° C. and with shaking at a speed of 140 rotations per minute (rpm) overnight to induce gene expression. Next, the cells were harvested and used for the subsequent $N_2$ production reaction.

(2.2) Culture for Production of $N_2$ from $^{15}N_2O$

The recombinant E. coli cells were added to an M9 medium (pH 7.0) containing 5 grams per liter (g/L) of glucose and 1.25 mM $^{15}N_2O$ (g) in a serum bottle and cultured to a density of $OD_{600=1}$ to prepare 30 mL of a culture mixture, which was then added to a 60-ml serum bottle and cultured at 30° C. and 140 rpm under stirring. The $^{15}N_2O$ (g) concentration represents a concentration with respect to a volume of the culture upper layer. At this time, the bottle was sealed with a stopper to prepare anaerobic conditions. A control group was the same as above, except that E. coli including an empty vector was used.

Next, the gas in the headspace of the reaction serum bottle was sampled and the production amount of $^{15}N_2$ was analyzed by GC-MS.

Figure 3:
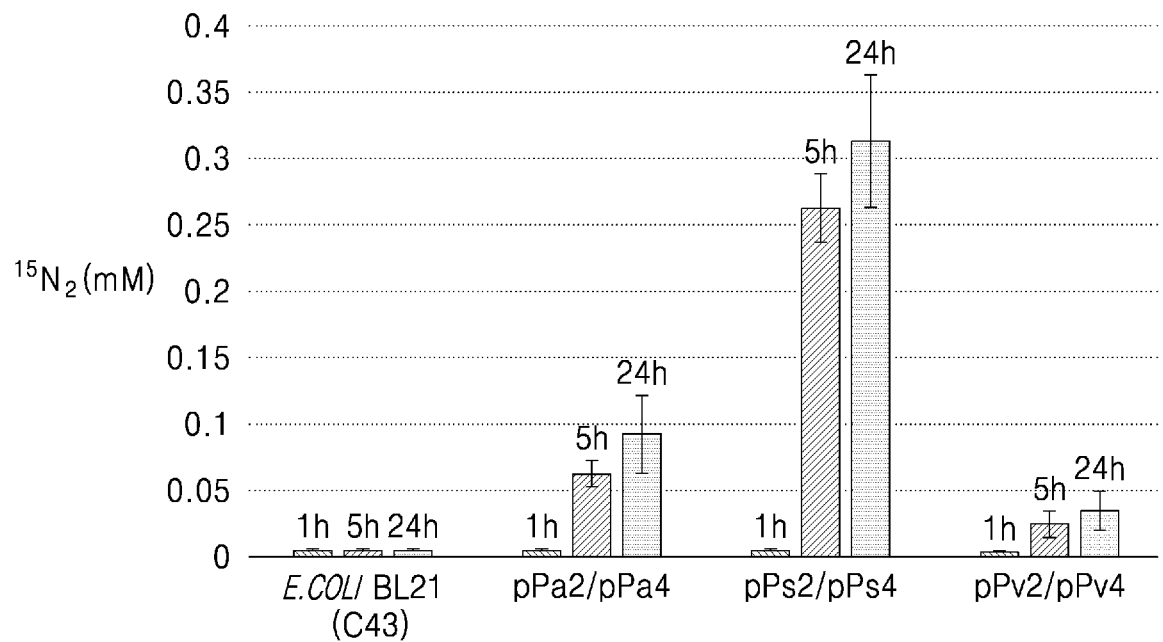
FIG. 3 shows results of converting $N_2O$ to $N_2$ using a recombinant E. coli including a pPs2/Pa2/Pv2 vector including a nosZ gene, a nosR gene, and a nosL gene, and a pPs4/Pa4/Pv4 vector including a nosD gene, a nosY gene, a nosF gene, a tatABC gene, and an apbE gene, in which nitrous oxide pathways are enhanced.

The results are shown in FIG. 3 and in Table 1 below. FIG. 3 shows the results of converting $N_2O$ to $N_2$ using the recombinant E. coli including the pPs2/Pa2/Pv2 vector including the nosZ gene, the nosR gene, and the nosL gene, and the pPs4/Pa4/Pv4 vector including the nosD gene, the nosY gene, the nosF gene, the tatABC gene, and the apbE gene, and in which the nitrous oxide pathways are enhanced.

As shown in FIG. 3, when the recombinant E. coli pPa2/pPa4 and pPs2/pPs4 were used, $N_2$ production was remarkably increased 5 hours and 24 hours later, as compared with E. coli BL31(C43) including the empty vector. In particular, the largest $N_2$ production was observed in the recombinant E. coli pPs2/pPs4. These results indicate that, even though the same nosZ, nosR, nosL, nosD, nosY, tatABC, apbE, and nosF genes are included, their expression levels in E. coli cells vary depending on their origin. In FIG. 3, pPa2/pPa4, pPs2/pPs4, and pPv2/pPv4 represent the recombinant E. coli including the pPs2 vector and the pPs4 vector, the recombinant E. coli including the pPs2 vector and the pPs4 vector, and the recombinant E. coli including the pPv2 vector and the pPv4 vector, respectively.

In addition, the production amount of $N_2$ by recombinant E. coli including each gene combination selected from the eight genes is shown in Tables 1, 2 and 3 below. Table 1 shows the production amount of $N_2$ (mM), when the recombinant E. coli including a combination of nos genes derived from P. stutzeri was cultured in the presence of $N_2O$ for 24 hours. Table 2 shows the production amount of $N_2$ (mM), when the recombinant E. coli including a combination of nos genes derived from P. aeruginosa was cultured in the presence of $N_2O$ for 24 hours. Table 3 shows the production amount of $N_2$ (mM), when the recombinant E. coli including a combination of nos genes derived from P. versutus was cultured in the presence of $N_2O$ for 24 hours.

TABLE 1

| | | Genes in pACYC_DEUT-1 vector | | | |
|---|---|---|---|---|---|
| | D, F | D, Y | D, F, Y | D, F, Y, apbE | D, F, Y, apbE, tatA |
| Genes in pET28a vector | Z | — | — | — | — | — |
| | ZR | — | — | — | 0.22 | 0.23 |
| | ZRL | — | — | — | 0.31 | 0.32 |

TABLE 2

| | | Genes in pACYC_DEUT-1 vector | | | |
|---|---|---|---|---|---|
| | D, F | D, Y | D, F, Y | D, F, Y, apbE | D, F, Y, apbE, tatA |
| Genes in pET28a vector | Z | — | — | — | — | — |
| | ZR | — | — | — | 0.07 | 0.07 |
| | ZRL | — | — | — | 0.08 | 0.08 |

TABLE 3

| | | Genes in pACYC_DEUT-1 vector | | | |
|---|---|---|---|---|---|
| | D, F | D, Y | D, F, Y | D, F, Y, apbE | D, F, Y, apbE, tatA |
| Genes in pET28a vector | Z | — | — | — | — | — |
| | ZR | — | — | — | 0.06 | 0.06 |
| | ZRL | — | — | — | 0.07 | 0.07 |

As shown in Tables, 1, 2 and 3, it was confirmed that, among the eight genes of the nitrous oxide reductase pathway, six genes, i.e., nosZ, nosR, nosD, nosF, nosY, and apbE genes, are essential genes.

(2.3) Culture for Production of $N_2$ from Fe(II)EDTA-$^{15}NO$

The recombinant E. coli cells obtained in (2.1) were added to an M9 medium (pH 7.0) containing 5 g/L glucose and 1.25 mM Fe(II)EDTA-$^{15}NO$ at a cell density of $OD_{600}=1$ to prepare a reaction mixture.

30 mL of the reaction mixture was added to a 60-ml serum bottle and then cultured at 30° C. and 140 rpm under stirring. The serum bottle was maintained in an anaerobic chamber and allowed to be under anaerobic conditions. A control group was the same as above, except that E. coli including an empty vector was used.

Next, the gas in the headspace of the reaction serum bottle was sampled and the production amount of $^{15}N_2$ was analyzed by GC-MS.

Figure 4:
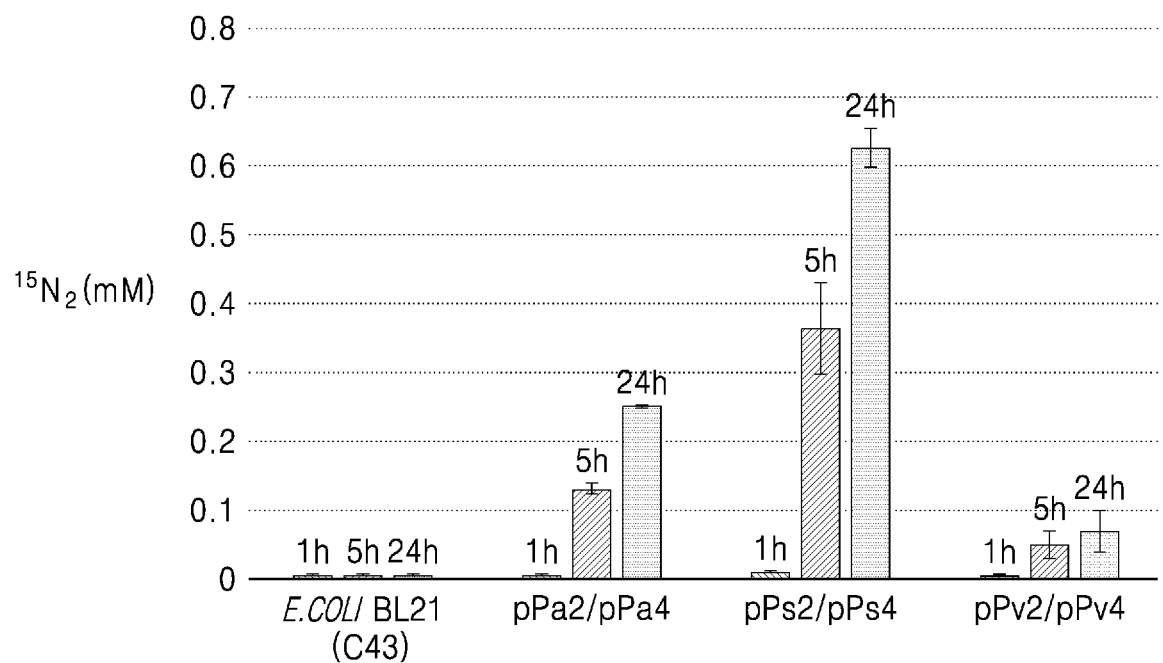
FIG. 4 is a graph of $^{15}N_2$ concentration (mM) versus test sample, which shows the results of converting $N_2O$ to $N_2$ using recombinant E. coli in which the nitrous oxide pathway is enhanced.

The results are shown in FIG. 4. FIG. 4 shows the results of converting $N_2O$ to $N_2$ using the recombinant E. coli in which nitrous oxide pathways are enhanced.

As shown in FIG. 4, when the recombinant E. coli pPa2/pPa4 and pPs2/pPs4 were used, $N_2$ production was remarkably increased 5 hours and 24 hours later, as compared with E. coli BL31(C43) including the empty vector. In particular, the largest $N_2$ production was observed in the recombinant E. coli pPs2/pPs4.

These results indicate that, even though the same nosZ, nosR, nosL, nosD, nosY, tatABC, apbE, and nosF genes are included, their expression levels in *E. coli* cells vary depend upon their origin. In FIG. 4, pPa2/pPa4, pPs2/pPs4, and pPv2/pPv4 represent the recombinant *E. coli* including the pPa2 vector and the pPa4 vector, the recombinant *E. coli* including the pPs2 vector and the pPs4 vector, and the recombinant *E. coli* including the pPv2 vector and the pPv4 vector, respectively.

Example 2: Evaluation of In Vitro Activity of Recombinant Nitrous Oxide Reductase NosZ In this exemplary embodiment, a nosZ gene encoding the enzyme nitrous oxide reductase (NosZ) and accessory genes essential for activity of the NosZ enzyme, i.e., nosR, nosL, nosD, nosF, nosY, apbE, and tat genes, were extracted from nos operons or gene clusters and genomes of three different strains of natural denitrifying bacteria (*Pseudomonas stutzeri*, *Pseudomonas aeruginosa*, and *Paracoccus versutus*), codon-optimized for *E. coli*, and then introduced into *E. coli*. As a result, a recombinant microorganism of the genus *Escherichia* having $N_2$-producing ability by converting $N_2O$ to $N_2$, i.e., a recombinant *E. coli*, was prepared. A cell lysate of the recombinant *E. coli* was obtained. To examine whether the cell lysate had the $N_2$-producing ability, the recombinant *E. coli* was cultured in the presence of a substrate containing a radioactive isotope $^{15}N$, i.e., $^{15}N_2O$ and FeEDTA-$^{15}NO$, and then the amount of $^{15}N_2$ in the culture thereof or the upper air layer in the culture was measured.

1. Construction of Vector and Preparation of Recombinant *E. coli* Transformed with this Vector
(1) Construction of Vector Expression vectors used in this exemplary embodiment were pETDuet™-1 and pACYCDuet™1 vectors (Novagen). pETDuet™-1 vector, in which a lac operator is operably linked to a T7 promoter, includes an ampicillin resistance $Amp^R$ gene as a selection marker. pACYCDuet™1 vector, in which a lac operator is operably linked to a T7 promoter, includes a chloramphenicol resistance $Cm^R$ gene as a selection marker.

Figure 5A:
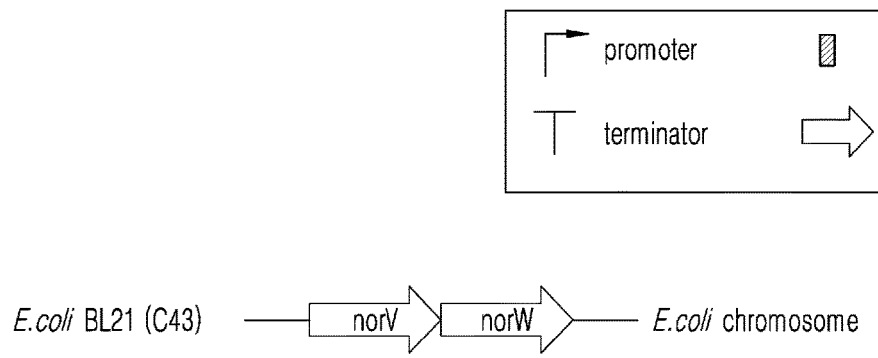
FIG. 5A is an illustration of a norVW site in the chromosome of E. coli.
Figure 5B:
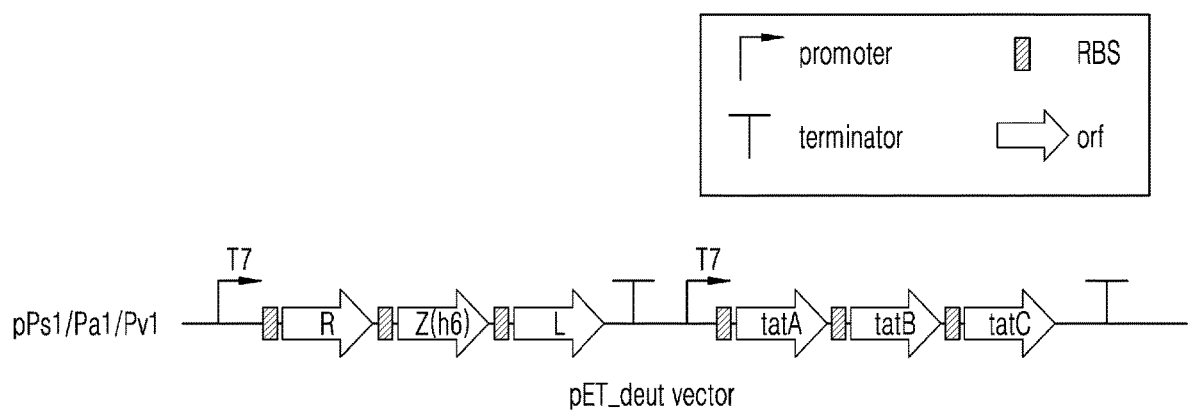
FIG. 5B is a map of a pPs1/Pa1/Pv1 vector.
Figure 5C:
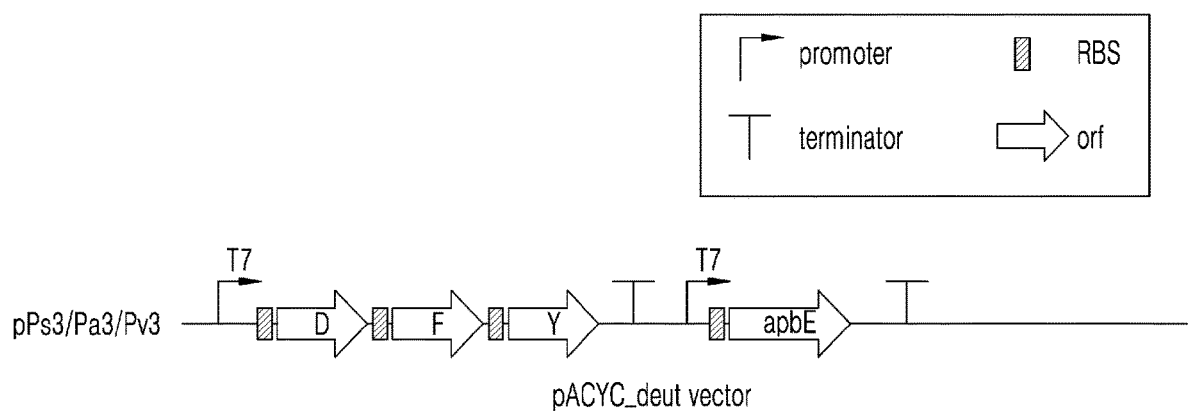
FIG. 5C is a map of a pPs3/Pa3/Pv3 vector.

FIG. 5 shows a norVW site in the chromosome of *E. coli* and maps of the pPs1/Pa1/Pv1 vector and the pPs3/Pa3/Pv3 vector introduced into *E. coli*. In FIG. 5A, norVW refers to the nitrous oxide reductase of *E. coli*; in FIG. 5B the pPs2/Pa2/Pv2 vector, the nosZ, nosR and nosL genes, derived from *P. stutzeri*, *P. aeruginosa*, or *P. versutus*, were commonly operably linked to a T7 promoter in pET_deut vector, and a ribosome binding site (RBS) having an *E. coli* RBS AAGGAG sequence; and in FIG. 5C, the pPs4/Pa4/Pv4 vector the nosD, nosY, tatA, tatB, and tatC genes, derived from *P. stutzeri*, *P. aeruginosa*, and *P. versutus*, were commonly operably linked to a T7 promoter, and a ribosome binding site (RBS) has an *E. coli* RBS AAGGAG sequence. In this regard, the nosZ gene includes a sequence encoding his-tag.

The nosZ, nosR, and nosL genes of three kinds of microorganisms were amplified by PCR using primer sets described in Example 1, DNA was synthesized by codon optimization as a template, and the resulting products were introduced into NcoI enzyme restriction site. Further, the tatA, tatB and tatC genes of three kinds of microorganisms were amplified by PCR using primer sets described in Example 1 and DNA was synthesized by codon optimization as a template, and the resulting products were introduced into NdeI enzyme restriction site.

In the pPs3/Pa3/Pv3 vector, the nosD, nosF, and nosY genes derived from *P. stutzeri*, *P. aeruginosa*, or *P. versutus*, were commonly operably linked to a T7 promoter in pACYC-duet vector, apbE gene was commonly operably linked to a T7 promoter, and RBS of each gene has an *E. coli* RBS AAGGAG sequence. The nosD, nosF, nosY, and apbE genes of three kinds of microorganisms were amplified by PCR using primer sets described in Example 1 and DNA synthesized by codon optimization as a template, and the resulting products of the nosD, nosF, and nosY genes were introduced into NcoI enzyme restriction site, and the resulting product of the apbE gene was introduced into NdeI enzyme restriction site.

(2) Preparation of Recombinant *E. coli* Having $N_2$-Producing Ability and Examination of Activity Thereof Two vectors consisting of the pPs1/Pa1/Pv1 vector and the pPs4/Pa4/Pv4 vector prepared in (1) were introduced into *E. coli* C43 (DE3) by transformation to prepare recombinant *E. coli*. The transformation was performed by electroporation. In this regard, each gene introduced into *E. coli* was a gene derived from the same strain.

(2.1) Culture for NosZ Maturation Stage

The recombinant *E. coli* was cultured at 37° C. in a 2×YT medium containing 50 μg/mL riboflavin and 0.25 mM $CuCl_2$ in an Erlenmeyer flask until the $OD_{600}$ reached 0.6, and then 1 mM IPTG was added and the bacteria were cultured at 30° C. with shaking at 140 rpm overnight to induce gene expression. Next, the recombinant *E. coli* cells were sonicated in a lysis buffer (50 mM $NaH_2PO_4$, 300 mM NaCl, 10 mM imidazole, pH 8.0). As a result, a cell lysate was obtained, and NosZ was purified from the cell lysate by a general method using Ni-NTA affinity column and the following two buffers: Ni-NTA washing buffer (50 mM $NaH_2PO_4$, 300 mM NaCl, 20 mM imidazole, pH 8.0) and Ni-NTA elution Buffer (50 mM $NaH_2PO_4$, 300 mM NaCl, 250 mM imidazole, pH 8.0).

Subsequently, the purified NosZ was brought into contact with $N_2O$ and used in the $N_2$ production reaction.

(2.2) Production of $N_2$ from $^{15}N_2O$ by Purified NosZ 0.2 mg/ml of purified NosZ obtained in (2.1), 2.0 mM benzyl viologen, 1.0 mM sodium dithionite, and 1.25 mM $^{15}N_2O(g)$ were added to water (pH 7.0) to prepare an aqueous reaction solution. 30 mL of the aqueous reaction solution was added to a 60 ml serum bottle, and cultured under stirring at 30° C. and 140 rpm. At this time, the bottle was sealed with a stopper to prepare anaerobic conditions. A control group was the same as above, except that an aqueous solution containing bovine serum albumin (BSA) was used.

Next, the gas in the headspace of the reaction serum bottle was sampled and the production amount of $^{15}N_2$ was analyzed by GC-MS.

Figure 6:
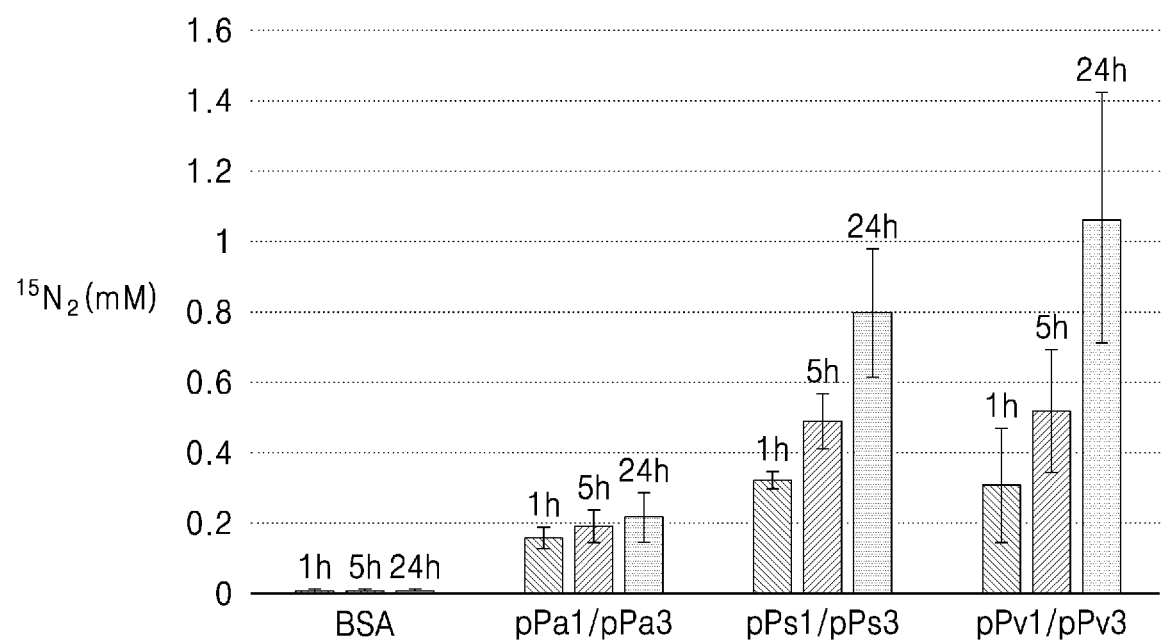
FIG. 6 is a graph of $^{15}N_2$ concentration (mM) versus test sample, which shows the results of converting $N_2O$ to $N_2$ using a recombinant E. coli including a pPs1/Pa1/Pv1 vector including a nosZ gene, a nosR gene, a nosL gene, a tatA, a tatB, and a tatC gene, and a pPs3/Pa3/pv3 vector including a nosD gene, a nosF gene, a nosY gene, an apbE gene, and in which nitrous oxide pathways are enhanced.

The results are shown in FIG. 6. FIG. 6 shows results of converting $N_2O$ to $N_2$ using NosZ derived from the recombinant *E. coli* including the pPs1/Pa1/Pv1 vector including the nosZ gene, the nosR gene, the nosL gene, the tatA, the tatB, and the tatC gene, and the pPs3/Pa3/pv3 vector including the nosD gene, the nosF gene, the nosY gene, and the apbE gene, in which nitrous oxide pathways are enhanced.

As shown in FIG. 6, when the recombinant *E. coli* pPa1/pPa3, pPs1/pPs3, and pPv1/pPv3-derived NosZ was used, $N_2$ production was remarkably increased 5 hours and 24 hours later, as compared with the control group containing BSA. In particular, the largest $N_2$ production was observed in the recombinant *E. coli* pPv1/pPv3.

These results indicate that, even though the same nosZ, nosR, nosL, nosD, nosY, tatABC, apbE, and nosF genes are included, their expression levels in *E. coli* cells vary depending on their origin, and they may not have activity in vivo, despite having in vitro activity.

In FIG. 6, pPa1/pPa3, pPs1/pPs3, and pPv1/pPv3 represent the recombinant *E. coli* including the pPa1 vector and the pPs3 vector, the recombinant *E. coli* including the pPs1 vector and the pPs3 vector, and the recombinant *E. coli* including the pPv1 vector and the pPv3 vector.

It should be understood that embodiments described herein should be considered in a descriptive sense only and not for purposes of limitation. Descriptions of features or aspects within each embodiment should be considered as available for other similar features or aspects in other embodiments. While one or more embodiments have been described with reference to the figures, it will be understood by those of ordinary skill in the art that various changes in form and details may be made therein without departing from the spirit and scope as defined by the following claims.

What is claimed is:

1. A recombinant microorganism of the genus *Escherichia* comprising a genetic modification that increases expression of a nosZ gene encoding NosZ, which is a nitrous oxide reductase, in the recombinant microorganism, wherein:
the NosZ is a polypeptide having 90% or greater sequence identity to the amino acid sequence of SEQ ID NO: 1, SEQ ID NO: 4, or SEQ ID NO: 7;
the recombinant microorganism comprises the nosZ gene, a nosR gene encoding NosR, a nosD gene encoding NosD, a nosF gene encoding NosF, a nosY gene encoding NosY, and an apbE gene encoding ApbE;
the nosZ gene, the nosR gene, the nosD gene, the nosF gene, the nosY gene and the apbE gene originate from a microorganism of the genus *Pseudomonas*, the genus *Paracoccus*, or a combination thereof; and
the nosZ gene and the nosR gene are comprised in a first vector, and the nosD gene, the nosF gene, the nosY gene, and the apbE gene are comprised in a second vector which is different from the first vector comprising the nosZ gene and the nosR gene; or
the nosZ gene and the nosR gene are comprised in a first operon, and the nosD gene, the nosF gene, the nosY gene, and the apbE gene are comprised in a second operon which is different from the first operon comprising the nosZ gene and the nosR gene.

2. The recombinant microorganism of claim 1, wherein the genetic modification comprises an increase in a copy number of the nosZ gene, a copy number of the nosR gene, a copy number of the nosD gene, a copy number of the nosF gene, a copy number of the nosY gene, or a copy number of the apbE gene, or a combination thereof.

3. The recombinant microorganism of claim 1, wherein:
the NosR is a polypeptide having 75% or greater sequence identity to the amino acid sequence of SEQ ID NO: 10, SEQ ID NO: 13, or SEQ ID NO: 16,
the NosD is a polypeptide having 75% or greater sequence identity to the amino acid sequence of SEQ ID NO: 19, SEQ ID NO: 22, or SEQ ID NO: 25,
the NosF is a polypeptide having 75% or greater sequence identity to the amino acid sequence of SEQ ID NO: 28, SEQ ID NO: 31, or SEQ ID NO: 34,
the NosY is a polypeptide having 75% or greater sequence identity to the amino acid sequence of SEQ ID NO: 37, SEQ ID NO: 40, or SEQ ID NO: 43, and
the ApbE is a polypeptide having 75% or greater sequence identity to the amino acid sequence of SEQ ID NO: 55, SEQ ID NO: 58, or SEQ ID NO: 61.

4. The recombinant microorganism of claim 1, wherein the microorganism does not comprise an exogenous nosL gene encoding a heterologous NosL.

5. A composition for reducing a concentration of nitrous oxide in a sample, the composition comprising:
a recombinant microorganism of the genus *Escherichia* comprising a genetic modification that increases expression of a nosZ gene encoding NosZ, which is a nitrous oxide reductase, in the recombinant microorganism, wherein:
the NosZ is a polypeptide having 90% or greater sequence identity to the amino acid sequence of SEQ ID NO: 1, SEQ ID NO: 4 or SEQ ID NO: 7;
the recombinant microorganism comprises the nosZ gene, a nosR gene encoding NosR, a nosD gene encoding NosD, a nosF gene encoding NosF, a nosY gene encoding NosY, and an apbE gene encoding ApbE;
the nosZ gene, the nosR gene, the nosD gene, the nosF gene, the nosY gene and the apbE gene originate from a microorganism of the genus *Pseudomonas*, the genus *Paracoccus*, or a combination thereof; and
the nosZ gene and the nosR gene are comprised in a first vector, and the nosD gene, the nosF gene, the nosY gene, and the apbE gene are comprised in a second vector which is different from the first vector comprising the nosZ gene and the nosR gene; or
the nosZ gene and the nosR gene are comprised in a first operon, and the nosD gene, the nosF gene, the nosY gene, and the apbE gene are comprised in a second operon which is different from the first operon comprising the nosZ gene and the nosR gene.

6. The composition of claim 5, wherein the genetic modification comprises an increase in a copy number of the nosZ gene, a copy number of the nosR gene, a copy number of the nosD gene, a copy number of the nosF gene, a copy number of the nosY gene, or a copy number of the apbE gene, or a combination thereof.

7. The composition of claim 5, wherein;
the NosR is a polypeptide having 75% or greater sequence identity to the amino acid sequence of SEQ ID NO: 10, SEQ ID NO: 13, or SEQ ID NO: 16,
the NosD is a polypeptide having 75% or greater sequence identity to the amino acid sequence of SEQ ID NO: 19, SEQ ID NO: 22, or SEQ ID NO: 25,
the NosF is a polypeptide having 75% or greater sequence identity to the amino acid sequence of SEQ ID NO: 28, SEQ ID NO: 31, or SEQ ID NO: 34,
the NosY is a polypeptide having 75% or greater sequence identity to the amino acid sequence of SEQ ID NO: 37, SEQ ID NO: 40, or SEQ ID NO: 43 and
the ApbE is a polypeptide having 75% or greater sequence identity to the amino acid sequence of SEQ ID NO: 55, SEQ ID NO: 58, or SEQ ID NO: 61.

8. The composition of claim 5, wherein the recombinant microorganism does not comprise an exogenous nosL gene encoding a heterologous NosL.

9. A method of reducing a concentration of nitrous oxide in a sample, the method comprising contacting a recombinant microorganism with a sample containing nitrous oxide to reduce the concentration of nitrous oxide in the sample, wherein:
the recombinant microorganism is of the genus *Escherichia* and comprises a genetic modification that increases expression of a nosZ gene encoding NosZ, which is a nitrous oxide reductase, in the recombinant microorganism;
the NosZ is a polypeptide having 90% or greater sequence identity to the amino acid sequence of SEQ ID NO: 1, SEQ ID NO: 4 or SEQ ID NO: 7;

the recombinant microorganism comprises the nosZ gene, a nosR gene encoding NosR, a nosD gene encoding NosD, a nosF gene encoding NosF, a nosY gene encoding NosY, and an apbE gene encoding ApbE;

the nosZ gene, the nosR gene, the nosD gene, the nosF gene, the nosY gene, and the apbE gene originate from a microorganism of the genus *Pseudomonas*, the genus *Paracoccus*, or a combination thereof; and the nosZ gene and the nosR gene are comprised in a first vector, and the nosD gene, the nosF gene, the nosY gene, and the apbE gene are comprised in a second vector which is different from the first vector comprising the nosZ gene and the nosR gene; or the nosZ gene and the nosR gene are comprised in a first operon, and the nosD gene, the nosF gene, the nosY gene, and the apbE gene are comprised in a second operon which is different from the first operon comprising the nosZ gene and the nosR gene.

10. The method of claim 9, wherein the genetic modification comprises an increase in a copy number of the nosZ gene, a copy number of the nosR gene, a copy number of the nosD gene, a copy number of the nosF gene, a copy number of the nosY gene, or a copy number of the apbE gene, or a combination thereof.

11. The method of claim 9, wherein:
the NosR is a polypeptide having 75% or greater sequence identity to the amino acid sequence of SEQ ID NO: 10, SEQ ID NO: 13, or SEQ ID NO: 16,
the NosD is a polypeptide having 75% or greater sequence identity to the amino acid sequence of SEQ ID NO: 19, SEQ ID NO: 22, or SEQ ID NO: 25,
the NosF is a polypeptide having 75% or greater sequence identity to the amino acid sequence of SEQ ID NO: 28, SEQ ID NO: 31, or SEQ ID NO: 34,
the NosY is a polypeptide having 75% or greater sequence identity to the amino acid sequence of SEQ ID NO: 37, SEQ ID NO: 40, or SEQ ID NO: 43 and
the ApbE is a polypeptide having 75% or greater sequence identity to the amino acid sequence of SEQ ID NO: 55, SEQ ID NO: 58, or SEQ ID NO: 61.

12. The method of claim 9, wherein the recombinant microorganism does not comprise an exogenous nosL gene encoding a heterologous NosL.

13. The method of claim 9, wherein the contacting is performed under anaerobic conditions in a sealed container.

14. The method of claim 9, wherein the contacting comprises culturing or incubating the recombinant microorganism in the presence of the nitrous oxide-containing sample.

\* \* \* \* \*

SEQUENCE LISTING

```
<160> NUMBER OF SEQ ID NOS: 141

<210> SEQ ID NO 1
<211> LENGTH: 638
<212> TYPE: PRT
<213> ORGANISM: Pseudomonas stutzeri

<400> SEQUENCE: 1

Met Ser Asp Asn Asp Ser Lys Asn Thr Pro Gln Thr Leu Glu Lys Asn
1               5                   10                  15

Gly Leu Ser Arg Arg Gly Phe Leu Gly Ala Ser Ala Leu Thr Gly Ala
            20                  25                  30

Ala Val Ala Ala Thr Ala Leu Gly Gly Ala Val Met Ser Arg Glu Ser
        35                  40                  45

Trp Ala Ala Val Lys Asp Ala Gln Ser Lys Ile His Val Gly Pro
    50                  55                  60

Gly Glu Leu Asp Glu Tyr Tyr Gly Phe Trp Ser Gly His Gln Gly
65                  70                  75                  80

Glu Val Arg Val Leu Gly Val Pro Ser Met Arg Glu Leu Met Arg Ile
                85                  90                  95

Pro Val Phe Asn Val Asp Ser Ala Thr Gly Trp Gly Leu Thr Asn Glu
            100                 105                 110

Ser Arg Ala Ile Met Gly Asp Ser Ala Lys Phe Leu Asn Gly Asp Cys
        115                 120                 125

His His Pro His Ile Ser Met Thr Asn Gly Lys Tyr Asp Gly Lys Tyr
    130                 135                 140

Leu Phe Ile Asn Asp Lys Ala Asn Ser Arg Val Ala Arg Ile Arg Leu
145                 150                 155                 160

Asp Ile Met Lys Cys Asp Lys Met Ile Thr Val Pro Asn Val Gln Ala
                165                 170                 175

Ile His Gly Leu Arg Leu Gln Lys Val Pro His Thr Lys Tyr Val Phe
            180                 185                 190

Ala Asn Ala Glu Phe Ile Ile Pro His Pro Asn Asp Gly Lys Val Phe
        195                 200                 205

Asp Leu Gln Asp Glu Asn Ser Tyr Thr Met Tyr Asn Ala Ile Asp Ala
    210                 215                 220

Glu Ser Met Glu Met Ala Phe Gln Val Ile Val Asp Gly Asn Leu Asp
225                 230                 235                 240

Asn Thr Asp Ala Asp Tyr Thr Gly Arg Phe Ala Ala Thr Cys Tyr
                245                 250                 255

Asn Ser Glu Lys Ala Phe Asp Leu Gly Gly Met Met Arg Asn Glu Arg
            260                 265                 270

Asp Trp Val Val Phe Asp Ile His Ala Ile Glu Lys Ala Val Lys
        275                 280                 285

Ala Gly Lys Phe Ile Thr Leu Gly Asp Ser Lys Val Pro Val Val Asp
    290                 295                 300
```

```
Gly Arg Lys Lys Asp Gly Lys Asn Ser Glu Phe Thr Arg Tyr Val Pro
305                 310                 315                 320

Val Pro Lys Asn Pro His Gly Leu Asn Thr Ser Ser Asp Gly Lys Tyr
            325                 330                 335

Phe Ile Ala Asn Gly Lys Leu Ser Pro Thr Cys Ser Met Ile Ala Ile
        340                 345                 350

Asp Met Leu Pro Asp Leu Phe Ala Gly Lys Leu Lys Asp Glu Arg Asp
    355                 360                 365

Val Val Val Gly Glu Pro Leu Gly Leu Gly Pro Leu His Thr Thr
370                 375                 380

Phe Asp Gly Arg Gly Asn Ala Tyr Thr Thr Leu Phe Ile Asp Ser Gln
385                 390                 395                 400

Val Val Lys Trp Asn Met Glu Glu Ala Arg Arg Ala Tyr Lys Gly Glu
            405                 410                 415

Lys Val Asn Tyr Ile Lys Gln Lys Leu Asp Val His Tyr Gln Pro Gly
        420                 425                 430

His Leu His Ala Ser Leu Cys Glu Thr Ser Glu Ala Asp Gly Lys Trp
    435                 440                 445

Leu Val Ala Leu Ser Lys Phe Ser Lys Asp Arg Phe Leu Pro Thr Gly
450                 455                 460

Pro Leu His Pro Glu Asn Asp Gln Leu Ile Asp Ile Ser Gly Asp Glu
465                 470                 475                 480

Met Lys Leu Val His Asp Gly Pro Thr Phe Ala Glu Pro His Asp Cys
            485                 490                 495

Ile Met Ala Arg Arg Asp Gln Ile Lys Thr Lys Lys Ile Trp Asp Arg
        500                 505                 510

Asn Asp Pro Phe Phe Ala Pro Thr Val Lys Met Ala Glu Lys Asp Gly
    515                 520                 525

Ile Asn Leu Thr Thr Asp Asn Lys Val Ile Arg Asp Gly Asn Lys Val
530                 535                 540

Arg Val Tyr Met Thr Ser Met Ala Pro Ala Tyr Gly Ile Thr Asp Phe
545                 550                 555                 560

Thr Val Lys Gln Gly Asp Glu Val Thr Val Val Thr Asn Ile Asp
            565                 570                 575

Gln Ile Glu Asp Val Ser His Gly Phe Val Val Asn His Gly Val
        580                 585                 590

Ser Met Glu Ile Ser Pro Gln Gln Thr Ser Ser Ile Thr Phe Val Ala
    595                 600                 605

Asp Lys Pro Gly Leu His Trp Tyr Tyr Cys Ser Trp Phe Cys His Ala
610                 615                 620

Leu His Met Glu Met Val Gly Arg Met Ile Val Glu Pro Ala
625                 630                 635

<210> SEQ ID NO 2
<211> LENGTH: 1917
<212> TYPE: DNA
<213> ORGANISM: Pseudomonas stutzeri

<400> SEQUENCE: 2
atgagcgaca atgattccaa gaacaccccg caaacgctgg agaagaacgg cctgagtcgc      60
cgcggcttcc tcggcgccag tgccctgacc ggtgccgcgg tggcggccac tgccctgggt     120
ggtgctgtca tgagccgcga aagctgggcg cagccgtca aggacgcaca atccaagatt      180
cacgtcggcc cgggcgaact ggacgagtat tacggcttct ggtccggcgg tcaccagggc     240
```

```
gaagtccgcg tgctgggcgt accgtccatg cgcgagctga tgcgtattcc ggtgttcaac      300
gtcgactccg ccaccggctg gggcctgacc aacgaaagcc gcgcgatcat gggcgacagc      360
gccaagttcc tgaacggcga ctgccaccac ccgcacatct ccatgaccaa cggcaagtac      420
gacggcaagt acctgttcat caacgacaag gccaacagcc gcgtcgcgcg tatccgcctc      480
gacatcatga agtgcgacaa gatgatcacc gtgccgaacg tgcaggcgat ccacggtctg      540
cgtctgcaga aggtgccgca caccaagtac gtcttcgcca acgccgagtt catcatcccg      600
cacccgaacg atggcaaggt cttcgacctg caggatgaga cagctacac catgtacaac       660
gccatcgatg cggaaagcat ggagatggcc ttccaggtga tcgtcgacgg caacctcgac      720
aacaccgacg ccgactacac cggccgcttc gccgctgcta cctgctacaa ctcggagaag      780
gccttcgacc tgggcgggat gatgcgcaac gagcgtgact gggtggtggt attcgacatc      840
cacgcgatcg aaaaagccgt caaggccggc aagttcatca ccctgggcga ctccaaggta      900
ccggtggtcg atgggcgcaa gaaggacggc aagaacagcg agttcacccg ctacgtgccg      960
gtgccgaaga acccccatgg cctgaacact tcttccgatg caagtactt catcgccaac      1020
ggcaagctgt cgccgacctg ctcgatgatc gccatcgaca tgctgcccga cctgttcgcc     1080
ggcaaactga aggacgagcg tgacgtggtg gtcggtgagc cggaactggg tctcggcccg     1140
ctgcacacca ccttcgacgg tcgcggcaac gcctacacca cgctgttcat cgacagccag     1200
gtggtcaagt ggaacatgga agaggcccgt cgcgcctaca agggcgagaa ggtcaactac     1260
atcaagcaga agctcgacgt gcactaccag ccgggccacc tgcacgcctc gctgtgcgaa     1320
accagcgaag ccgacggcaa gtggctggtg gcgctgtcca agttctccaa ggaccgcttc     1380
ctgcctaccg gccgctgca cccggaaaac gatcagctga tcgatatctc cggcgacgag      1440
atgaagctgg tgcacgacgg cccgactttc gccgagccgc acgactgcat catggcccgc     1500
cgcgatcaga tcaagaccaa gaagatctgg accgcaacg atccgttctt cgcgccgacc      1560
gtgaagatgg ccgagaagga cggtatcaac ctgactaccg acaacaaggt catccgcgac     1620
ggcaacaagg ttcgtgtcta catgaccctcc atggcgccgg cctacggcat caccgacttc     1680
accgtgaagc agggtgacga agtgactgtc gtggtgacca catcgacca gatcgaagac      1740
gtgtcccacg gcttcgtggt ggtcaaccat ggcgtgagca tggagatcag cccgcagcag     1800
acctcgtcca ttaccttcgt ggcggacaag cccggcctgc actggtacta ctgcagctgg     1860
ttctgccacg cgctgcacat ggagatggtc ggccgcatga tcgtcgaacc ggcctga       1917
```

<210> SEQ ID NO 3
<211> LENGTH: 1917
<212> TYPE: DNA
<213> ORGANISM: Artificial
<220> FEATURE:
<223> OTHER INFORMATION: codon optimized Ps nosZ gene

<400> SEQUENCE: 3

```
atgtccgaca atgacagcaa aaatacgcca cagactctgg agaagaacgg ttgtcgcgg        60
cgcggctttt taggggcgag cgcattgaca ggtgctgctg tagcagcgac agctctcggc      120
ggtgctgtca tgtcgcgcga gtcgtgggct gcagccgtga agatgctca atcgaaaatc       180
catgttgggc caggggaact cgatgaatac tacggcttct ggtcgggtgg gcatcagggg     240
gaagtccgtg ttctgggcgt ccctagtatg cgtgaactca tgcggattcc tgtattcaac      300
gtcgactcag ccacaggttg gggcctcaca aatgaaagcc gtgccattat gggtgattcc      360
gcaaagttcc tcaatggcga ttgtcatcat ccacacatct cgatgactaa cggcaaatat     420
```

```
gatggtaaat acttatttat taatgacaag gccaatagtc gggttgcacg gattcgcctc    480
gatattatga agtgcgataa aatgattaca gtcccaaacg tacaggctat ccatggcctc    540
cggcttcaaa aggtaccgca tacaaagtac gtcttcgcga acgcggaatt catcattcct    600
catccaaatg acggcaaggt cttcgattta caagacgaga attcctatac gatgtacaat    660
gcgattgacg cagaaagcat ggaaatggcc tttcaggtga ttgtcgatgg aacttagac     720 aacacagacg ccgactatac tggtcggttc gcagcagcta catgttacaa ctctgagaaa    780
gcctttgacc ttggtggtat gatgcggaat gagcgtgact gggtcgttgt attcgacatt    840
catgctattg aaaaggcagt aaagccggc aagtttatta cgttaggcga ttctaaagtg     900
ccagtggtag acggccgcaa gaaggatggt aagaactccg agttcacgcg ctacgtgcct    960
gtgccaaaaa acccacatgg tttaaatact tcgagtgacg gtaagtattt catcgcaaac    1020
gggaaactca gcccgacatg ctctatgatt gcgattgata tgcttccgga cctgttcgct    1080
gggaaactca aggatgaacg tgatgtggtt gttggtgagc cagaacttgg gctgggtcct    1140
ctgcacacta cgtttgacgg gcgcgggaat gcctacacaa cactgtttat cgactcccaa    1200
gttgtgaagt ggaacatgga agaagcgcgc cgtgcttaca aaggggagaa ggttaattat    1260
attaaacaga agcttgacgt ccattatcaa ccggggcatc tccatgcttc gttgtgtgag    1320
acgtcagaag cagatggtaa atggctggtg gctttatcta aattttcgaa ggaccgtttc    1380
ctgccaactg gtcctctcca cccggagaac gaccagttaa tcgacatcag cggggacgaa    1440
atgaagctgg tgcacgacgg ccctacgttt gcggaacctc acgactgtat tatgcacgt     1500 cgggaccaaa ttaaaacgaa gaaaatctgg gatcgcaatg acccgttttt tgcacctacg    1560
gtcaagatgg cagagaagga tggtatcaac ttgactaccg ataacaaggt gatccgggat    1620
gggaataaag ttcgcgtgta catgactagt atggcacctg cctacgggat taccgatttc    1680
accgtgaaac aaggtgacga agttaccgtt gtggttacaa atatcgatca aattgaggac    1740
gtcagtcacg gttttgtcgt agtcaatcac ggtgtatcaa tggaaatctc accacaacag    1800
acatcttcca ttacgtttgt cgccgacaaa ccggggttac attggtacta ttgtagctgg    1860
ttctgccatg cccttcatat ggagatggta ggtcgcatga ttgtagaacc agcatga       1917
```

<210> SEQ ID NO 4
<211> LENGTH: 636
<212> TYPE: PRT
<213> ORGANISM: Pseudomonas aeruginosa

<400> SEQUENCE: 4

```
Met Ser Asp Asp Thr Lys Ser Pro His Glu Glu Thr His Gly Leu Asn
1               5                   10                  15

Arg Arg Gly Phe Leu Gly Ala Ser Ala Leu Thr Gly Ala Ala Ala Leu
            20                  25                  30

Val Gly Ala Ser Ala Leu Gly Ser Ala Val Val Gly Arg Glu Ala Arg
        35                  40                  45

Ala Ala Gly Lys Gly Glu Arg Ser Lys Ala Glu Val Ala Pro Gly Glu
    50                  55                  60

Leu Asp Glu Tyr Tyr Gly Phe Trp Ser Gly His Ser Gly Glu Val
65                  70                  75                  80

Arg Val Leu Gly Val Pro Ser Met Arg Glu Leu Met Arg Ile Pro Val
                85                  90                  95

Phe Asn Val Asp Ser Ala Thr Gly Trp Gly Leu Thr Asn Glu Ser Lys
            100                 105                 110
```

-continued

```
Arg Val Leu Gly Asp Ser Ala Arg Phe Leu Asn Gly Asp Cys His His
            115                 120                 125

Pro His Ile Ser Met Thr Asp Gly Lys Tyr Asp Gly Lys Tyr Leu Phe
130                 135                 140

Ile Asn Asp Lys Ala Asn Ser Arg Val Ala Arg Ile Arg Leu Asp Val
145                 150                 155                 160

Met Lys Cys Asp Arg Ile Val Thr Ile Pro Asn Val Gln Ala Ile His
                165                 170                 175

Gly Leu Arg Leu Gln Lys Val Pro His Thr Arg Tyr Val Phe Cys Asn
            180                 185                 190

Ala Glu Phe Ile Ile Pro His Pro Asn Asp Gly Ser Thr Phe Asp Leu
        195                 200                 205

Ser Gly Asp Asn Ala Phe Thr Leu Tyr Asn Ala Ile Asp Ala Glu Thr
    210                 215                 220

Met Glu Val Ala Trp Gln Val Ile Val Asp Gly Asn Leu Asp Asn Thr
225                 230                 235                 240

Asp Met Asp Tyr Ser Gly Arg Phe Ala Ala Ser Thr Cys Tyr Asn Ser
                245                 250                 255

Glu Lys Ala Val Asp Leu Gly Gly Met Met Arg Asn Glu Arg Asp Trp
            260                 265                 270

Val Val Val Phe Asp Ile Pro Arg Ile Glu Ala Glu Ile Lys Ala Lys
        275                 280                 285

Arg Phe Val Thr Leu Gly Asp Ser Lys Val Pro Val Asp Gly Arg
    290                 295                 300

Arg Lys Asp Gly Lys Asp Ser Pro Val Thr Arg Tyr Ile Pro Val Pro
305                 310                 315                 320

Lys Asn Pro His Gly Leu Asn Thr Ser Pro Asp Gly Lys Tyr Phe Ile
                325                 330                 335

Ala Asn Gly Lys Leu Ser Pro Thr Cys Thr Met Ile Ala Ile Glu Arg
            340                 345                 350

Leu Gly Asp Leu Phe Ala Gly Lys Leu Ala Asp Pro Arg Asp Val Val
        355                 360                 365

Val Gly Glu Pro Glu Leu Gly Leu Gly Pro Leu His Thr Thr Phe Asp
    370                 375                 380

Gly Arg Gly Asn Ala Tyr Thr Thr Leu Phe Ile Asp Ser Gln Leu Val
385                 390                 395                 400

Lys Trp Asn Leu Ala Asp Ala Val Arg Ala Tyr Lys Gly Glu Lys Val
                405                 410                 415

Asp Tyr Ile Arg Gln Lys Leu Asp Val Gln Tyr Gln Pro Gly His Asn
            420                 425                 430

His Ala Thr Leu Cys Glu Thr Ser Glu Ala Asp Gly Lys Trp Ile Val
        435                 440                 445

Val Leu Ser Lys Phe Ser Lys Asp Arg Phe Leu Pro Thr Gly Pro Leu
    450                 455                 460

His Pro Glu Asn Asp Gln Leu Ile Asp Ile Ser Gly Glu Glu Met Lys
465                 470                 475                 480

Leu Val His Asp Gly Pro Thr Phe Ala Glu Pro His Asp Cys Ile Leu
                485                 490                 495

Ala Arg Arg Asp Gln Ile Lys Thr Arg Lys Ile Trp Asp Arg Lys Asp
            500                 505                 510

Pro Phe Phe Ala Glu Thr Val Lys Arg Ala Glu Lys Asp Gly Ile Asp
        515                 520                 525
```

```
Leu Met Lys Asp Asn Lys Val Ile Arg Glu Gly Asn Lys Val Arg Val
    530                 535                 540

Tyr Met Val Ser Met Ala Pro Ser Phe Gly Leu Thr Glu Phe Lys Val
545                 550                 555                 560

Lys Gln Gly Asp Glu Val Thr Val Thr Ile Thr Asn Leu Asp Glu Ile
                565                 570                 575

Glu Asp Val Thr His Gly Phe Val Met Val Asn His Gly Val Cys Met
            580                 585                 590

Glu Ile Ser Pro Gln Gln Thr Ser Ile Thr Phe Val Ala Asp Lys
        595                 600                 605

Pro Gly Val His Trp Tyr Tyr Cys Ser Trp Phe Cys His Ala Leu His
610                 615                 620

Met Glu Met Cys Gly Arg Met Leu Val Glu Lys Ala
625                 630                 635

<210> SEQ ID NO 5
<211> LENGTH: 1911
<212> TYPE: DNA
<213> ORGANISM: Pseudomonas aeruginosa

<400> SEQUENCE: 5
atgagcgacg acacgaaaag cccccacgaa gaaacccacg gcctgaaccg ccgcggcttc    60
ctcggcgcct cggcgctgac cggagccgcc gccctggttg cgccagcgc cctgggcagc    120 gcggtggtcg gccgcgaggc ccgggccgcg ggcaagggcg agcgcagcaa ggccgaggtc    180
gcccccggcg aactggatga gtactacggg ttctggagcg gcggacattc cggcgaagta    240
cgcgtgctcg gcgtgccgtc gatgcgcgag ctgatgcgca taccggtgtt caacgtcgac    300
tcggccaccg gctggggcct gaccaacgag agcaagcggg tcctcggcga cagcgcgcgc    360
ttcctcaacg gcgactgcca ccatccgcac atctcgatga ccgacggcaa gtacgacggc    420
aagtacctgt tcatcaacga caaggccaac agccgggtcg cgcgcatccg cctggacgtc    480
atgaaatgcg accgcatcgt caccattccc aacgtccagg cgatccacgg cctgcgcctg    540
caaaaggtgc gcataccccg ctacgtgttc tgcaacgccg agttcatcat ccccatcccc    600
aacgacggct cgaccttcga cctgtccggc gacaacgcct tcaccctgta caacgccatc    660
gacgccgaga ccatggaagt ggcctggcag gtgatcgtcg acggcaacct cgacaacacc    720
gacatggact cagcggcag gttcgccgcc tccacctgct acaactcgga aaaggccgtc    780
gacctcggcg catgatgcg caacgagcgc gactgggtgg tggtgttcga catcccgcgc    840
atcgaggcca gatcaaggc gaagcgcttc gtcaccctcg gcgactcgaa ggtgccggtg    900
gtcgacggcc ggcgcaagga cggcaaggac agcccggtga cccgctacat cccggtaccg    960
aagaaccccc acgggctgaa cacctcgccg gacggcaagt acttcatcgc caacggcaag    1020
ctctcgccga cctgcaccat gatcgccatc gagcgcctcg gcgacctgtt cgccggcaag    1080
ctggccgacc cgcgcgacgt ggtggtgggc gagccggaac tgggcctcgg cccgctgcac    1140
accactttcg atggccgagg caacgcctat accacgctgt catcgacag ccagttggtg    1200 aagtggaacc tcgccgacgc ggtgcgcgc tacaagggcg agaaggtcga ctacatccgc    1260
cagaagctcg acgtgcagta ccagccgggg cacaaccacg ccactctgtg cgagaccagc    1320
gaagccgacg gcaagtggat cgtggtgctc agcaagttct ccaaggaccg cttcctgccc    1380
accggtccgc tgcaccccga gaacgaccag ttgatcgaca tttccggcga ggaaatgaag    1440
ctggtccacg acgccccgac cttcgccgaa ccgcacgatt gcatcctcgc cgccgcgac    1500
```

```
cagatcaaga cccgcaagat ctgggaccgc aaggacccgt tcttcgccga gacggtcaag   1560
cgcgcggaaa aggacggcat cgacctgatg aaggacaaca aggtcatccg cgagggcaac   1620
aaggtccgcg tctacatggt ctcgatggcg ccctccttcg gcctcaccga gttcaaggtg   1680
aagcagggcg acgaagtcac cgtgaccatc accaacctcg acgagatcga ggacgtgacc   1740
cacggcttcg tcatggtcaa ccacggcgtc tgcatggaga tcagcccgca acagacctcg   1800
tcgatcacct tcgtcgccga taagcccggg gtgcactggt actactgcag ctggttctgc   1860
cacgccctgc acatggaaat gtgcgggcgg atgctggtgg aaaaggcttg a            1911
```

<210> SEQ ID NO 6
<211> LENGTH: 1911
<212> TYPE: DNA
<213> ORGANISM: Artificial
<220> FEATURE:
<223> OTHER INFORMATION: codon optimized Pa nosZ gene

<400> SEQUENCE: 6

```
atgtccgatg ataccaaatc cccgcacgag gagactcatg gctcaatcg ccggggtttt    60 ctcggtgctt ctgctctcac cggcgcggca gctcttgtag gggcatctgc cttgggttca   120
gctgtcgttg gcgggaagc tcgggctgct gggaagggcg aacgttctaa ggctgaagtc    180
gcgccagggg aacttgacga gtattatggc ttctggtcgg gtggtcattc gggcgaggta   240
cgggttttgg gcgtaccatc catgcgtgaa ctcatgcgga ttcctgtgtt caatgtggat    300
agtgcaacag gttgggggtt gactaatgaa tcgaagcgcg tccttgggga ttcagcccgt    360
ttcttaaacg gggattgcca tcatcctcat atcagcatga ccgatggcaa atacgatggc    420
aaatatttgt ttatcaatga taaagcgaac tcacgggtag cacgtatccg tctggatgtt    480
atgaagtgtg accgtattgt cacaattcca acgtccaag ccattcacgg cctccggttg     540
cagaaggtgc cgcatacacg ctacgtattt tgtaatgccg agtttattat tccacaccca    600
aacgatggct ctacctttga tttaagcggg gacaacgcgt tcaccctgta caacgcaatc    660
gatgctgaaa ctatggaagt tgcttggcag gttatcgtgg atgggaactt agataacacc    720
gacatggatt actctgggcg cttcgccgcg tcgacttgtt acaattctga aaaggcagtg    780
gacctgggtg ggatgatgcg gaacgagcgc gactgggtag tcgtcttcga cattccgcgt    840
attgaggccg agatcaaggc gaaacggttt gtaacactcg gggattcaaa agttccagtt    900
gtagatggtc gccgtaagga cggcaaagac agccctgtta cgcgctatat cccagtacct    960
aaaaacccgc acggtctcaa caccagtcct gatggcaagt actttatcgc gaatggtaaa   1020
ctgtcaccta catgcaccat gattgcaatc gaacgtttag gtgatttgtt tgctgggaag   1080
cttgccgacc cacgtgatgt ggtagtaggc gaaccagagc tcgggctggg gccgctccat   1140
accacgtttg atggtcgggg taatgcgtat actaccttat tcatcgactc gcagttagtg   1200
aagtggaact tagctgacgc agtacgggcc tacaagggcg aaaaagttga ctatattcgt   1260
caaaagttag acgtacagta ccagccgggc cacaatcacg caacgttatg tgaaacttct   1320
gaagcagatg ggaagtggat cgtagttctg tccaaatttt caaaagatcg ctttctccct   1380
acaggtccat acatccagaa aaatgatcaa cttatcgaca tttcggggga agagatgaaa   1440
ctggtacacg atggtcctac attcgcggaa ccacacgatt gtatcctcgc gcggcgtgat   1500
cagattaaga ctcgcaagat ttgggaccgg aaggatccgt ttttcgctga gactgtgaag   1560
cgtgccgaaa aggatggcat cgaccttatg aaggacaata aggtaatccg cgaggggaac   1620
aaagtacgcg tctacatggt ttcaatggca ccttctttcg ggctcaccga atttaaagta   1680
```

```
aaacaaggcg atgaggtgac ggttactatt acaaatttag acgaaatcga agacgtgacg    1740
cacggttttg tgatggtgaa ccatggggta tgcatggaga tttcgccaca acaaacttct    1800
tctatcacgt ttgtcgctga taaaccaggc gtacattggt actattgtag ttggttctgt    1860
catgctttac acatggagat gtgcggtcgg atgctggtgg agaaggcttg a             1911
```

<210> SEQ ID NO 7
<211> LENGTH: 653
<212> TYPE: PRT
<213> ORGANISM: Pseudomonas versutus

<400> SEQUENCE: 7

```
Met Glu Thr Lys Gln Gln Asn Gly Leu Ser Arg Arg Ala Leu Leu Gly
1               5                   10                  15

Ala Thr Ala Gly Gly Ala Ala Met Ala Gly Ala Phe Gly Gly Arg Leu
            20                  25                  30

Ala Leu Gly Pro Ala Val Ile Gly Ala Gly Ala Gly Val Ala Thr
        35                  40                  45

Ala Ala Gly Ser Gly Ala Ala Leu Ala Ala Ser Gly Asp Gly Ala Val
    50                  55                  60

Ala Pro Gly Gln Leu Asp Asp Tyr Tyr Gly Phe Trp Ser Ser Gly Gln
65                  70                  75                  80

Thr Gly Glu Leu Arg Ile Leu Gly Val Pro Ser Met Arg Glu Leu Met
                85                  90                  95

Arg Val Pro Val Phe Asn Arg Cys Ser Ala Thr Gly Trp Gly Ile Thr
            100                 105                 110

Asn Glu Ser Ile Leu Ile His Glu Arg Thr Met Ser Glu Arg Thr Arg
        115                 120                 125

Lys His Leu Ala Ala Asn Gly Lys Arg Ile His Asp Asn Gly Asp Leu
    130                 135                 140

His His Val His Met Ser Phe Thr Glu Gly Lys Tyr Asp Gly Arg Phe
145                 150                 155                 160

Leu Phe Met Asn Asp Lys Ala Asn Thr Arg Val Ala Arg Val Arg Cys
                165                 170                 175

Asp Val Met Lys Cys Asp Ala Ile Leu Glu Val Pro Asn Ala Lys Ala
            180                 185                 190

Ile His Gly Leu Arg Pro Gln Lys Trp Pro Arg Ser Asn Tyr Val Phe
        195                 200                 205

Cys Asn Gly Glu Asp Glu Ala Pro Leu Ile Asn Asp Gly Thr Thr Met
    210                 215                 220

Asp Asp Ile Ser Thr Tyr Val Asn Val Phe Thr Ala Val Asp Ala Asp
225                 230                 235                 240

Lys Trp Glu Val Ala Trp Gln Val Leu Val Ser Gly Asn Leu Asp Asn
                245                 250                 255

Cys Asp Ala Asp Tyr Glu Gly Lys Trp Ala Phe Ser Thr Ser Tyr Asn
            260                 265                 270

Ser Glu Met Gly Met Thr Leu Pro Glu Met Thr Glu Ala Glu Met Asp
        275                 280                 285

His Val Val Phe Asn Ile Ala Glu Ile Glu Lys Ala Ile Glu Ala
    290                 295                 300

Gly Asn Phe Glu Glu Ile Asn Gly Cys Lys Val Leu Asp Gly Arg Lys
305                 310                 315                 320

Glu Ala Asn Ser Gln Phe Thr Arg Tyr Ile Pro Ile Ala Asn Asn Pro
                325                 330                 335
```

His Gly Cys Asn Met Ala Pro Asp Lys Lys His Leu Val Val Ala Gly
                340                 345                 350

Lys Leu Ser Pro Thr Val Thr Val Leu Asp Val Thr Arg Phe Asp Ala
            355                 360                 365

Val Phe Asn Glu Asn Ala Asp Pro Arg Ser Ala Val Ala Glu Pro
    370                 375                 380

Glu Leu Gly Leu Gly Pro Leu His Thr Ala Phe Asp Gly Arg Gly Asn
385                 390                 395                 400

Ala Tyr Thr Ser Leu Phe Leu Asp Ser Gln Val Val Lys Trp Asn Ile
                405                 410                 415

Glu Glu Ala Ile Arg Ala Tyr Ala Gly Glu Gln Val Asp Pro Ile Lys
            420                 425                 430

Asp Lys Ile Asp Val His Tyr Gln Pro Gly His Leu Lys Thr Val Met
            435                 440                 445

Gly Glu Thr Leu Asp Ala Ser Asn Asp Trp Met Val Cys Leu Ser Lys
    450                 455                 460

Phe Ser Lys Asp Arg Phe Leu Asn Val Gly Pro Leu Lys Pro Glu Asn
465                 470                 475                 480

Asp Gln Leu Ile Asp Ile Ser Gly Asp Lys Met Val Leu Val His Asp
                485                 490                 495

Gly Pro Thr Phe Ala Glu Pro His Asp Ala Ile Ala Val His Pro Ser
            500                 505                 510

Ile Met Ser Ser Val Ile Lys Ser Val Trp Asp Arg Asn Asp Pro Met
            515                 520                 525

Trp Ala Glu Thr Arg Lys Gln Ala Glu Ala Asp Gly Val Asn Ile Asp
    530                 535                 540

Glu Trp Thr Asp Gln Ile Ile Arg Asp Gly Asn Lys Val Arg Val Tyr
545                 550                 555                 560

Met Ser Ser Val Ala Pro Ser Phe Ser Val Glu Ser Phe Thr Val Thr
                565                 570                 575

Glu Gly Asp Glu Val Thr Val Ile Val Thr Asn Leu Asp Glu Ile Asp
            580                 585                 590

Asp Leu Thr His Gly Phe Thr Met Gly Asn His Gly Val Ala Met Glu
            595                 600                 605

Ile Ser Pro Gln Gln Thr Ser Ser Val Thr Phe Val Ala Ala Asn Pro
    610                 615                 620

Gly Val Tyr Trp Tyr Tyr Cys Gln Trp Phe Cys His Ala Leu His Met
625                 630                 635                 640

Glu Met Arg Gly Arg Met Met Val Glu Pro Lys Ala Ala
                645                 650

<210> SEQ ID NO 8
<211> LENGTH: 1962
<212> TYPE: DNA
<213> ORGANISM: Pseudomonas versutus

<400> SEQUENCE: 8
atggaaacca aacagcaaaa cggcctgagc cgccgcgcgc ttctgggcgc gaccgccggc        60
ggtgcggcca tggccggcgc gttcgggggg cgcctgcgc tgggaccggc cgtgatcggt        120
gcgggcgccg cggcgtcgc caccgccgcc ggcagcggcg cggcgctggc cgccagcggc        180
gacggcgcgg tcgcgccggg ccagctggac gactattacg gcttctggtc ctcgggccag        240
accggcgagc tgcgcatcct gggcgttccc tcgatgcgcg agctgatgcg ggtgccggtc        300

| | | |
|---|---|---|
| ttcaaccgct gctcggccac cggctggggc atcaccaacg agtcgatcct catccacgaa | 360 | |
| cgcaccatga gcgagcggac gaggaagcac cttgccgcca acggcaagcg catccacgac | 420 | |
| aacggcgacc tgcaccacgt ccacatgtcc tttaccgagg gcaagtatga cggccgcttc | 480 | |
| ctgttcatga cgacaaggc caatacccgc gtggcgcggg tgcgctgcga cgtgatgaaa | 540 | |
| tgcgacgcca tcctggaggt gccgaacgcc aaggccatcc acggcctgcg cccgcagaaa | 600 | |
| tggccgcgca gcaactatgt gttctgcaac ggcgaggacg aggcgccgct gatcaacgac | 660 | |
| ggcaccacga tggacgacat ctcgacctat gtgaacgtct tcaccgccgt cgatgccgac | 720 | |
| aagtgggaag tcgcctggca ggtgctggtc tcgggcaacc tcgacaactg cgatgccgat | 780 | |
| tacgagggca atgggccttt ctcgacctcg tataactcgg agatgggcat gaccctgccc | 840 | |
| gagatgaccg aagccgagat ggaccatgtc gtggtcttca acatcgccga gatcgaaaag | 900 | |
| gccatcgagg ccggcaattt tgaagagatc aacggctgca aggtgctgga cggccggaaa | 960 | |
| gaggcgaaca gccagttcac ccgctacatc ccgatcgcca acaacccgca tggctgcaac | 1020 | |
| atggccccgg acaagaagca cctggtcgtc gcgggcaagc tgtcgcccac ggtgacggtg | 1080 | |
| ctggacgtga ccaggttcga cgcggtgttc aacgagaatg ccgatccgcg cagcgccgtg | 1140 | |
| gtggccgagc cggaactggg cctgggcccg ctgcacaccg ccttcgacgg gcgcggcaac | 1200 | |
| gcctatacct cgctgtttct cgacagccag gtggtcaagt ggaacatcga ggaggcgatc | 1260 | |
| cgcgcctatg ccggcgagca ggtcgatccg atcaaggaca gatcgacgt gcattaccag | 1320 | |
| cccggccacc tcaagacggt gatgggcgag acgctggacg ccagcaacga ctggatggtc | 1380 | |
| tgcctgtcca gttctcgaa ggaccgcttc ctgaacgtcg gccgctgaa gccggaaaac | 1440 | |
| gaccagctga tcgacatctc gggcgacaag atggtgctgg tccatgacgg cccgaccttt | 1500 | |
| gccgagccgc atgacgccat cgccgtgcat ccctcgatca tgtcgagcgt catcaagtcg | 1560 | |
| gtctgggacc gcaacgatcc catgtgggcc gaaacccgca agcaggccga ggccgacggc | 1620 | |
| gtcaacatcg acgaatggac cgaccagatc atccgcgacg caacaaggt gcgggtctac | 1680 | |
| atgtccagcg tcgcgcccag cttctcggtc gaaagcttca ccgtgaccga gggcgacgag | 1740 | |
| gtcacggtca tcgtcaccaa ccttgacgag atcgacgacc tgacccacgg tttcaccatg | 1800 | |
| ggcaaccacg tgtcgccat ggagatctcg ccccagcaga cctcgtcggt gactttcgtc | 1860 | |
| gccgccaatc cggggtgta ctggtattat tgccagtggt tctgccatgc gctgcacatg | 1920 | |
| gaaatgcgcg gccgcatgat ggtcgagccg aaggcggcct ga | 1962 | |

<210> SEQ ID NO 9
<211> LENGTH: 1962
<212> TYPE: DNA
<213> ORGANISM: Artificial
<220> FEATURE:
<223> OTHER INFORMATION: codon optimized Pv nosZ gene

<400> SEQUENCE: 9

| | | |
|---|---|---|
| atggaaacaa aacagcagaa cggtttatca cgtcgtgcac tgctcggtgc cacggcaggg | 60 | |
| ggtgcggcca tggcgggtgc gttcggcggc cgcttggcat taggtccggc agtaattggt | 120 | |
| gcaggtgctg caggcgttgc gaccgcggca ggctctgggg cagcgctcgc ggcgagcggt | 180 | |
| gacggcgcgg ttgctccagg gcagttagat gactactatg gcttttggtc gtccggtcaa | 240 | |
| actggcgagc tccgcatttt aggcgttcct tcgatgcggg agttaatgcg tgtcccagta | 300 | |
| tttaatcgtt gttccgcaac gggttgggc attacgaacg aatcaatctt aatccatgaa | 360 | |
| cggactatgt ccgaacgcac tcgtaagcac ctcgcagcga acggtaagcg tatccacgat | 420 | |

```
aatgggacc tgcaccacgt acacatgtct ttcactgaag gcaagtacga tgggcgtttc    480
cttttcatga atgacaaggc caatactcgt gttgcacggg tacgttgcga cgttatgaaa    540
tgcgatgcta ttctggaggt tcctaacgca aaagcaattc atggtttacg gccacaaaag    600
tggcctcgga gtaattatgt attctgtaac ggcgaggacg aagcccctct catcaatgac    660
ggcacgacga tggatgacat ttctacgtac gtgaatgtat ttacggccgt ggacgcggac    720
aaatgggaag tagcctggca agtactggtc tctggtaatc tggacaattg tgacgcggat    780
tacgaaggca agtgggcttt ttctacctca tacaatagtg aaatgggtat gactctcccg    840
gagatgacgg aggccgagat ggaccatgtg gtagtgttta acattgcaga gattgaaaaa    900
gcgattgagg cggggaattt cgaggaaatt aacgggtgca agtcttgga cggtcgtaag    960 gaggccaatt cccagttcac acggtatatc cctattgcaa ataacccaca cggttgtaac   1020
atggccccgg ataaaaagca tctggtagta gcaggcaagt tgtctcctac cgtaacagtt   1080
ttagatgtta cgcgcttcga tgcggtgttt aatgaaaatg cagatcctcg ctcagcagtt   1140
gtcgctgagc cagaacttgg tttgggtccg ctgcacactg catttgacgg cgggggaat    1200 gcatacacat ctttgtttct cgactcgcaa gtcgttaaat ggaacatcga agaggcgatt   1260
cgcgcttatg ctggcgagca agtcgatccg atcaaagaca aaatcgacgt acattatcag   1320
ccgggtcatc ttaagacagt tatgggcgag actttggacg cctcgaacga ctggatggtc   1380
tgcctttcca agttttcgaa agatcggttt ctcaacgttg cccactcaa gccagaaaat    1440 gatcaactca ttgacatttc tggtgacaag atggtacttg tccacgatgg gccgacattt   1500
gccgagcctc acgatgcaat gcagtgcac ccttcaatca tgagtagtgt tattaaatcc    1560
gtctgggacc gcaatgaccc gatgtgggcg gagactcgga agcaggccga ggctgatggc   1620
gttaatattg atgagtggac cgaccagatt atccgtgacg gcaacaaagt tcgggtatat   1680
atgagttcgg tagctccgag cttttcagtg gaaagtttta ccgttactga gggtgatgag   1740
gtaacggtca ttgttacgaa cctcgacgag atcgatgatc tgactcacgg gttcacgatg   1800
ggcaatcacg gggtagccat ggagatcagt ccacaacaaa catcgtcggt aacctttgtt   1860
gcagccaatc cggcgttta ttggtattat tgtcagtggt tctgtcacgc attacatatg    1920
gaaatgcgcg gtcgcatgat ggtggaacca aaagctgcgt ga                      1962
```

<210> SEQ ID NO 10
<211> LENGTH: 726
<212> TYPE: PRT
<213> ORGANISM: Pseudomonas stutzeri

<400> SEQUENCE: 10

```
Met Lys Pro Leu Gly Phe Ala Val Val Gly Thr Ser Arg Arg Trp Val
1               5                   10                  15

Ala Gly Phe Ala Ile Leu Leu Ala Leu Met Phe Cys Val Ser Val Ala
            20                  25                  30

Gln Ala Lys Glu Tyr Glu Ala Glu Gln Gln Arg Ile Glu Leu Leu Phe
        35                  40                  45

Pro Lys Val Thr Glu Ile Ser Glu Pro Glu Gly Glu Tyr Gln Val Arg
    50                  55                  60

Thr Leu Ala Asp Gly Val Gly Thr Ile Tyr Gly Tyr Ala Phe Gln Ser
65                  70                  75                  80

Ile Asn Val Thr Asp Met Pro Ala Tyr Ser Gly Lys Pro Ile Asn Met
                85                  90                  95
```

```
Gln Ile Leu Leu Asp Pro Lys Gly Val Ile Asp Ala Tyr Met Leu
            100                 105                 110
Glu His His Glu Pro Ile Val Leu Ile Gly Ile Pro Glu Gln Lys Val
        115                 120                 125
His Asp Phe Asn Ala Asn Tyr Ser Gly Ile His Val Asp Gln Arg Val
    130                 135                 140
Val Val Gly Arg Ser Ser Asp Lys Ser Ala Val Thr Val Asp Ala Val
145                 150                 155                 160
Thr Gly Ala Thr Val Thr Val Met Val Ile Asn Glu Ile Val Met Arg
                165                 170                 175
Ala Ala His Thr Val Ala Val Asp Leu Gly Leu Val Glu Ala Gly Ala
            180                 185                 190
Thr Ala Arg Pro Lys Pro Ala Leu Val Arg Glu Asp Val Phe Gln Pro
        195                 200                 205
Thr Ser Trp Thr Glu Leu Val Gly Asn Gly Ala Ile Arg Arg Met His
    210                 215                 220
Leu Thr Arg Gly Gln Val Asp Asp Ala Phe Lys Gly Thr Glu Ala Glu
225                 230                 235                 240
Gly Val Asp Val Ala Ala Ala Glu Gln Arg Asp Glu Thr Phe Ile Asp
                245                 250                 255
Leu Tyr Ala Thr His Leu Asn Pro Pro Thr Ile Gly Arg Asn Leu Leu
            260                 265                 270
Gly Glu Arg Gln Tyr Ala Asp Leu Met Ala Asn Leu Lys Pro Gly Glu
        275                 280                 285
His Ala Phe Ala Val Leu Ala Asn Gly Glu Tyr Ser Phe Lys Gly Ser
    290                 295                 300
Gly Tyr Val Arg Gly Gly Ile Phe Asp Arg Val Gln Leu Arg Gln Phe
305                 310                 315                 320
Gly Asp Thr Ile Ser Phe Arg Asp Leu Asp Phe Ile Arg Leu Ser Asp
                325                 330                 335
Val Tyr Ala Glu Gly Met Pro Glu Phe Glu Met Ala Ile Phe Thr
            340                 345                 350
Ala Arg Glu Gln Tyr Arg Phe Asp Pro Gly Ser Pro Trp Asn Leu Glu
        355                 360                 365
Leu Leu Val Arg Arg Gln Val Gly Pro Val Glu Ser Ile Phe Thr Ser
    370                 375                 380
Phe Glu Met Pro Tyr Val Met Pro Glu Glu Tyr Ile Glu Arg Val Pro
385                 390                 395                 400
Leu Thr Ala Glu Glu Leu Ala Ala Ile Glu Glu Ala Asn Arg Pro Leu
                405                 410                 415
Trp Val Asn Ile Trp Tyr Gln Lys Ser Phe Gln Val Gly Val Ile Leu
            420                 425                 430
Val Ala Leu Ala Leu Leu Thr Val Ile Leu Phe Leu Gln Asp Lys Phe
        435                 440                 445
Thr Gln His Pro Asn Phe Leu Lys Arg Leu Arg His Gly Tyr Leu Val
    450                 455                 460
Phe Thr Val Val Phe Ile Gly Trp Tyr Ala Leu Gly Gln Leu Ser Val
465                 470                 475                 480
Val Asn Val Leu Thr Phe Val His Ala Leu Val Gln Asp Phe Arg Trp
                485                 490                 495
Glu Leu Phe Leu Thr Asp Pro Val Ile Phe Ile Leu Trp Val Phe Thr
            500                 505                 510
Ala Ala Ser Ile Leu Leu Trp Gly Arg Gly Val Phe Cys Gly Trp Leu
```

```
                515                 520                 525
    Cys Pro Phe Gly Ala Leu Gln Glu Leu Ile Asn Glu Ala Ala Arg Lys
        530                 535                 540
    Leu Lys Ile Pro Gln Tyr Asp Leu Pro Phe Gly Val His Glu Arg Leu
    545                 550                 555                 560
    Trp Ala Ile Lys Tyr Ile Val Leu Leu Val Leu Phe Gly Ile Ser Leu
                    565                 570                 575
    Glu Ser Met Met Met Ala Glu Lys Ala Ala Glu Ile Glu Pro Phe Lys
                580                 585                 590
    Thr Ala Ile Thr Leu Lys Phe Asp Arg Gln Trp Trp Phe Val Ala Tyr
                595                 600                 605
    Ala Val Phe Leu Leu Val Ile Asn Ile Phe Thr Arg Lys Val Tyr Cys
                610                 615                 620
    Arg Tyr Val Cys Pro Leu Gly Ala Gly Leu Ala Ile Thr Gly Arg Phe
    625                 630                 635                 640
    Arg Leu Phe Asp Trp Leu Lys Arg Arg Lys Glu Cys Gly Asn Pro Cys
                    645                 650                 655
    Gln Ile Cys Ala Asn Glu Cys Glu Val Gln Ala Ile His Pro Asp Gly
                660                 665                 670
    His Ile Asn His Asn Glu Cys His Tyr Cys Leu Asp Cys Gln Met Thr
                675                 680                 685
    Tyr His Asn Glu Asn Lys Cys Pro Pro Leu Ile Gln Lys Asn Lys Arg
    690                 695                 700
    Lys Lys Arg Asp Lys Lys Ala Pro Val Gly Ala Glu Leu Ile Pro Val
    705                 710                 715                 720
    Val Gln Val Val Glu Pro
                        725

<210> SEQ ID NO 11
<211> LENGTH: 2181
<212> TYPE: DNA
<213> ORGANISM: Pseudomonas stutzeri

<400> SEQUENCE: 11
atgaaacccc taggttttgc agtcgtcggc acctcgcgcc gctgggtagc tggctttgcg      60
atcctcctgg ctttgatgtt ctgtgtatcc gtggcacagg caaaagagta cgaagcagag     120
cagcaacgca tcgagttgct tttcccgaaa gtcaccgaaa tttccgagcc cgagggcgag     180
taccaggtgc gcacccttgc ggacggggtg ggcacgatct acgggtacgc cttccagagc     240
atcaacgtca cggacatgcc ggcctactcc ggcaagccga tcaacatgca gatcctgctc     300
gaccccaagg gcgtcatcgt cgatgcttac atgctcgagc accacgaacc catcgtgctc     360
atcggtattc ccgagcagaa ggttcacgac ttcaacgcca actacagcgg catccacgtc     420
gaccagcgcg tggtagtcgg tcgttccagc gacaagagcg cggtcacggt cgacgccgtt     480
accggcgcca ccgtgaccgt gatggtgatc aacgagatcg tcatgcgtgc ggcccacacc     540
gtggcggtgg atctggggct ggtcgaggcg ggggccaccg cgcgacccaa gccggcgctg     600
gtgcgcgagg acgtcttcca gccgaccagc tggaccgagc tggtgggcaa tggcgccatc     660
cgccgcatgc acctgacccg tggccaggtc gacgatgcct tcaagggcac cgaggccgag     720
ggtgtcgacg ttgccgcggc ggaacagcgc gacgaaacct tcatcgatct ctacgccacg     780
cacctgaacc cgccgaccat cggccgcaac ctgctgggcg agcgccagta cgccgatctg     840
atggcgaacc tcaagcccgg cgagcatgcc ttcgcggtgc tggccaacgg cgaatactca     900
```

```
ttcaagggct cgggttacgt gcgtggcggc atcttcgatc gggtgcagct gcgccagttc    960
ggcgacacca tcagcttccg cgacctggac ttcatccgtc tatccgacgt gtatgccgaa   1020
ggcatgccgg aattcttcga gatggcgatc ttcactgccc gcgagcagta tcgcttcgat   1080
ccgggctcgc cctggaacct cgagcttctg gtgcgtcgcc aggtcggccc ggtggagagc   1140
atcttcacca gcttcgagat gccctacgtg atgcccgagg agtacatcga gcgggtgccg   1200
ctgaccgccg aagagctggc cgccatcgag aagccaacc ggccgctgtg ggtcaacatc   1260
tggtaccaga gagcttcca ggtgggggtg atcctggtcg cgctggcgct gctgacggtc   1320
atcctcttcc tgcaggacaa gttcacccag catcccaact tcctcaagcg gctgcgccat   1380
ggctacctgg tcttcaccgt ggtgttcatc ggctggtatg ccctggggca actgtcggtg   1440
gtcaacgtgc tgaccttcgt ccatgcgctg gtgcaggact tccgctggga gctgttcctg   1500
accgatccgg tgatcttcat tctctgggta ttcaccgccg ctagcattct gctgtggggg   1560
cgtggcgtgt tctgcggctg gctgtgcccc ttcggcgccc tgcaggagct gatcaacgag   1620
gccgcgcgca agctgaagat tccccagtac gacctgccct tcggcgttca cgagcggctc   1680
tgggccatca agtacatcgt gctgctggtg cttttcggca tctcgctgga atccatgatg   1740
atggccgaga aggccgccga gatcgaaccc ttcaagaccg ccatcacgct gaagttcgac   1800
cgccagtggt ggttcgtcgc ctacgcggtg ttcctgctgg taatcaacat cttcactcgc   1860
aaggtctatt gccgctacgt ctgcccgctg ggcgcggggc tggcgatcac cggtcgcttc   1920
cggctgttcg actggctcaa gcggcgcaag gaatgcggca cccctgtca gatctgtgcc   1980
aacgaatgcg aagtgcaggc gattcatccg gacgggcata tcaaccacaa cgaatgccat   2040
tactgcctgg actgccagat gacctaccac aacgaaaaca gtgcccgcc gcttattcag   2100
aagaacaagc gcaagaagcg cgacaagaaa gcgccggtcg gggccgagct gatccctgta   2160
gtgcaagtgg tggaaccctg a                                              2181
```

<210> SEQ ID NO 12
<211> LENGTH: 2181
<212> TYPE: DNA
<213> ORGANISM: Artificial
<220> FEATURE:
<223> OTHER INFORMATION: codon optimized Ps nosR gene

<400> SEQUENCE: 12

```
atgaagccgt taggtttcgc cgtcgtaggc acatcccgcc gctgggttgc tggtttcgca     60
atcctgctcg ccctgatgtt ttgtgttagt gtagcgcagg ctaaagagta cgaagcagag    120
caacagcgca ttgaattact ctttcctaaa gtgactgaga tctcagaacc ggagggcgaa    180
taccaagtgc gtacgcttgc agatggtgtg ggtacgatct atgggtatgc cttccagtcc    240
atcaatgtaa ccgatatgcc ggcgtatagt ggtaaaccga tcaatatgca gattctcctg    300
gacccaaagg gggtaatcgt cgacgcttac atgctcgagc accatgaacc tattgtgctg    360
atcggtattc cggaacagaa agttcacgac ttcaacgcta attacagtgg gatccatgtt    420
gaccagcgcg ttgtcgtagg tcgtagttcc gataaatcgg cagttaccgt ggatgccgtc    480
actggcgcta ccgtcacagt aatggtcatc aacgagatcg tcatgcgcgc ggctcacacg    540
gtcgcagtag atttgggtct cgttgaggct ggtgccactg cccgcccgaa gccggcatta    600
gtgcgcgaag acgttttcca gccaacatcg tggaccgagc ttgtgggcaa tggggctatt    660
cgccgtatgc acttaacccg cggtcaagtt gacgatgcct taaaggtac tgaagctgag    720
ggcgtggatg ttgctgccgc tgagcagcgc gacgaaacct ttattgactt atatgcgacc    780
```

```
catcttaacc cacctacaat cggtcgtaac ttacttgggg aacgccagta tgcggatctg    840
atggcaaatc tgaaaccagg cgagcacgct tcgccgtttt tagcgaatgg cgagtacagc    900
ttcaaagggt ccggctatgt gcgcggcggg attttttgatc gcgtgcaact ccgtcagttt    960
ggggacacta tctcttttcg tgatttggat tttattcgtc tttctgacgt atatgcggaa   1020
ggtatgccag agttttcga atggcaatt tttactgcac gcgaacaata ccgctttgac   1080
ccagggtctc cgtggaatct cgaattattg gtacgccgtc aagtcggtcc agtcgagtca   1140
atctttactt cattcgaaat gccttacgtg atgcctgaag aatacatcga gcgcgtgccg   1200
cttaccgctg aagaacttgc cgcaatcgag gaagcgaacc gccctctttg ggtcaatatc   1260
tggtatcaga atcgtttca gttggggtg atcctggtcg cccttgctct cttaacggta   1320
attttgttcc ttcaagacaa atttacccag catcctaact tccttaagcg cttgcgccat   1380
ggctacctcg tattcaccgt cgttttttatt ggctggtatg cattaggcca gttatctgtc   1440
gtgaacgtgc ttacattcgt tcacgcactt gtgcaggact tcgctggga gctgtttctc   1500
accgaccctg tgatcttcat cctgtgggtc ttcaccgctg ccagcattct tctctggggg   1560
cgcgggtct tttgtggg tg ctgtgtcca tttggcgccc tccaggaact tatcaatgaa   1620
gccgcgcgca agctgaagat cccgcagtat gatcttccgt ttggcgttca tgagcgcctt   1680
tgggccatta gtatatcgt actgctggtc ttatttggta tctctttaga gtcaatgatg   1740
atggcggaaa aggccgcaga aattgagcct tttaaaactg cgatcacact gaaattcgac   1800
cgccaatggt ggttcgtggc ctatgccgtt tccttgttgg ttatcaatat tttcacccgc   1860
aaggtttatt gccgttatgt ttgtcctctc ggtgccggcc tcgctatcac cggtcgtttt   1920
cgcttatttg attggcttaa acgtcgtaaa gagtgtggca acccgtgtca gatctgtgct   1980
aacgagtgcg aggtacaggc gatccatcct gatgggcaca tcaaccacaa tgagtgtcac   2040
tattgcttgg actgccaaat gacgtaccat aatgaaaaca agtgtccacc gttgattcaa   2100
aagaataagc gtaaaaagcg cgacaaaaaa gccccggtag gcgcagagtt aatcccagtg   2160
gtccaagtgg ttgagccttg a                                            2181
```

<210> SEQ ID NO 13
<211> LENGTH: 715
<212> TYPE: PRT
<213> ORGANISM: Pseudomonas aeruginosa

<400> SEQUENCE: 13

Met Arg Ala Leu Arg Phe Ser Ala Gly Ser Trp Arg Cys Val Phe Ala
1               5                   10                  15

Trp Met Leu Leu Leu Val Gly Leu Ala Ala Gln Gly Ala Glu Leu Ser
            20                  25                  30

Glu Leu Glu Arg Leu Arg Ile Ala Gln Val Phe Pro Ala Val Glu Arg
        35                  40                  45

Ile Gly Asp Pro Glu Gly Asp Tyr Gly Val Arg Arg Leu Ser Lys Gly
    50                  55                  60

Glu Glu Thr Leu Gly Tyr Ala Phe Gln Thr Leu Ser Val Thr Asp Ile
65                  70                  75                  80

Pro Ala Tyr Ser Gly Lys Pro Ile Asn Leu Gln Val Ile Leu Asp Pro
                85                  90                  95

Gln Ala Val Ile Arg Asp Ala Tyr Val Leu Glu His His Glu Pro Ile
            100                 105                 110

Leu Leu Ile Gly Ile Pro Glu Glu Lys Leu His Ala Phe Ser Ala Arg

```
                115                 120                 125
Tyr Asp Gly Val Arg Ala Asp Gln Arg Val Val Gly Arg Ser Ser
130                 135                 140
Asp Pro Gln Ala Val Thr Val Asp Ala Val Ser Gly Ala Thr Val Thr
145                 150                 155                 160
Val Met Val Val Asn Glu Ile Val Met Arg Ala Ala His Thr Val Ala
                165                 170                 175
Val Ser Leu Gly Leu Ile Glu Asp Arg Gly Asn Val Arg Pro Lys Pro
            180                 185                 190
Ala Gln Val Arg Gln Pro Ala Ala Thr Ala Asn Trp Ser Glu Leu
        195                 200                 205
Leu Gly Asn Gly Ala Ile Arg Arg Leu Gln Leu Ser Arg Gly Gln Ile
210                 215                 220
Asp Asp Ala Phe Lys Gly Ser Glu Ala Glu Gly Ile Gly Glu Ala Asp
225                 230                 235                 240
Ala Ala His Arg Asp Glu Pro Phe Ile Asp Leu Tyr Ser Ala Leu Leu
                245                 250                 255
Asn Pro Pro Ala Val Gly Arg Ser Leu Leu Gly Asp Asn Gln Tyr Arg
            260                 265                 270
Glu Leu Met Ala Ser Leu Lys Pro Gly Glu Tyr Ala Phe Val Val Leu
        275                 280                 285
Gly Asp Gly Glu Tyr Ser Phe Lys Gly Ser Gly Tyr Val Arg Gly Gly
290                 295                 300
Ile Phe Asp Arg Val Gln Leu Arg Gln Phe Gly Asp Ile Ile Ser Phe
305                 310                 315                 320
Arg Asp Leu Asp Tyr Gln Arg Leu Ser Asp Val Tyr Ala Glu Gly Met
                325                 330                 335
Pro Glu Phe Arg Glu Met Ala Ile Phe Val Ala Arg Ala Ser Gln Arg
            340                 345                 350
Phe Asp Pro Gly Ser Pro Trp Thr Leu Glu Leu Leu Val Arg Arg Gln
        355                 360                 365
Thr Gly Pro Val Ala Gly Val Phe Thr Ser Phe Glu Leu Ala Cys Gln
370                 375                 380
Thr Pro Glu Glu Tyr Leu Glu Arg Pro Gln Pro Thr Ala Glu Glu Leu
385                 390                 395                 400
Ala Ala Leu Glu Glu Ala Ala Arg Pro Leu Trp Leu Arg Val Trp Tyr
                405                 410                 415
Gln Lys Ser Phe Gln Val Gly Val Leu Cys Thr Ala Leu Val Leu Leu
            420                 425                 430
Leu Ala Ile Leu Phe Leu Gln Asp Arg Leu Val Arg Arg Pro Arg Leu
        435                 440                 445
Met Gln Arg Leu Arg Thr Gly Tyr Leu Ala Phe Thr Leu Val Tyr Leu
        450                 455                 460
Gly Trp Tyr Ser Leu Gly Gln Leu Ser Val Val Asn Val Leu Thr Phe
465                 470                 475                 480
Val His Ala Leu Phe Glu Gly Phe Arg Trp Glu Leu Phe Leu Ser Asp
                485                 490                 495
Pro Leu Leu Phe Ile Leu Trp Thr Phe Thr Ala Ala Ser Leu Leu Leu
            500                 505                 510
Trp Gly Arg Gly Val Phe Cys Gly Trp Leu Cys Pro Phe Gly Ala Leu
        515                 520                 525
Gln Glu Leu Leu Asn Glu Leu Ala Arg Lys Leu Arg Val Pro Gln Phe
        530                 535                 540
```

Gln Val Pro Phe Ala Val His Glu Arg Leu Trp Ala Ile Lys Tyr Ile
545                 550                 555                 560

Ile Leu Leu Val Leu Phe Gly Leu Ser Leu Glu Ser Leu Ala Leu Ala
            565                 570                 575

Glu Gln Ala Ala Glu Val Glu Pro Phe Lys Thr Ala Ile Thr Leu Gly
        580                 585                 590

Phe Asp Arg Gln Trp Trp Phe Val Ala Tyr Val Ala Leu Leu Val
        595                 600                 605

Val Asn Leu Phe Thr Arg Lys Val Tyr Cys Arg Tyr Leu Cys Pro Leu
            610                 615                 620

Gly Ala Ala Leu Ala Ile Pro Ala Lys Ala Arg Leu Phe Asp Trp Leu
625                 630                 635                 640

Lys Arg Arg Ala Glu Cys Gly Arg Pro Cys Gln Leu Cys Ala Arg Glu
                645                 650                 655

Cys Glu Ile Gln Ala Ile His Pro Asp Gly Arg Ile Glu Thr Asn Glu
            660                 665                 670

Cys His Tyr Cys Leu Asp Cys Gln Met Thr Tyr His Asp Gln Asp Lys
        675                 680                 685

Cys Pro Pro Leu Val Asn Lys Arg Lys Arg Ala Lys Ser Ala Pro
690                 695                 700

Ala Asp Asn Ala Arg Ile Pro Ala Glu Asn Leu
705                 710                 715

<210> SEQ ID NO 14
<211> LENGTH: 2148
<212> TYPE: DNA
<213> ORGANISM: Pseudomonas aeruginosa

<400> SEQUENCE: 14

```
atgcgcgccc ttcgttttc cgccggatcg tggcggtgtg tcttcgcctg gatgctcctg      60
ctggtcggcc tcgccgccca gggtgccgaa ctcagcgagt ggagcgcct gcgcatcgcc     120 caggtattcc ccgcggtcga gcggatcggc gaccccgaag gcgactacgg cgtacgccgc    180
ctgagcaagg gcgaggaaac cctcggctac gccttccaga ccctcagcgt caccgacatc    240
ccggcttact ccggcaagcc gatcaacctg caggtgatcc tcgatccgca ggcggttatc    300
cgcgacgcct acgtcctcga caccacgaa ccgatcctgc tgatcggtat cccggaagag    360
aagctgcacg ccttcagcgc caggtacgac ggcgtgcgcg ccgaccagcg ggtggtggtc    420
ggccgctcca gcgacccgca ggcggttacc gtcgacgcgg tgagcggcgc cacggtgacg    480
gtgatggtgg tcaacgagat cgtcatgcgc gccgcacata cggtggcggt ttccctcggc    540
ctgatcgagg accgcggcaa tgtgcggccc aaaccggcgc aggtgcgcca gcaaccggca    600
gcgaccgcaa actggagcga actgctcggc aacgggcgga tccgccgcct gcagttgagt    660
cgcgggcaga tcgacgacgc cttcaagggc agcgaggccg aaggcatcgg cgaagccgac    720
gcggcgcacc gcgacgagcc gttcatcgat ctctacagcg ccctgctcaa ccctcccgcg    780
gtgggccgca gcctgctcgg cgacaaccag taccgcgaac tgatggcgtc gctgaagcca    840
ggcgaatacg ccttcgtcgt gctcggcgac ggcgagtatt ccttcaaggg ttccggctac    900
gtgcgcggtg gcatcttcga tcgggtccaa ctgcgccagt tcggcgacat catcagcttc    960
cgcgacctcg actaccagcg cctgtccgga gtctatgccg aaggcatgcc ggagttccgc   1020
gagatggcga tcttcgtcgc ccgcgccagc cagcgttttcg atccgggctc gccctggacc   1080
ctggagttgc tcgtgcggcg ccagaccggc ccggtggcgg gggtattcac cagcttcgag   1140
```

```
ctggcctgcc agacgcccga ggaatacctg gagcggccgc agccaacggc cgaggaactg      1200
gccgccctgg aagaggctgc ccggccgctg tggctgcggg tctggtacca gaagagtttc      1260
caggtcgggg tcctctgtac cgccctcgtc ctgctcctgg cgatcctctt cctccaggac      1320
cgcctggtgc gacggccgcg cctgatgcag cgactgcgca ccggctacct ggcgttcacc      1380
ctggtctacc tgggctggta cagcctcggc cagctatcgg tggtcaacgt gctgaccttc      1440
gtccacgcgc tgttcgaagg cttccgctgg gagctgttcc tcagcgaccc gctgctgttc      1500
atcctctgga ccttcaccgc agccagcctg ctgctctggg ccgcggcgt gttctgcggc       1560 tggctgtgcc cgttcggtgc gctacaggaa ctgctcaacg aactcgcgcg caagctccgc      1620
gtgccgcagt tccaggtgcc gttcgccgtg cacgagcggc tctgggcgat caagtacatc      1680
atcctgctgg tgctcttcgg tctctcccct gaatccctgg cgctggccga gcaggccgcg      1740
gaggtggagc cgttcaagac cgccatcacc ctcggcttcg accgccagtg gtggttcgtc      1800
gcctacgccg tcgcgctgct ggtggtcaac ctgttcaccc gcaaggtcta ttgccgctac      1860
ctctgcccgc tgggcgcggc cctggcgatc ccggccaagg cgcgcctgtt cgactggctc      1920
aagcgccgtg cggaatgcgg caggccctgc cagctctgtg cccgcgaatg cgagatccag      1980
gcgatccatc ccgacggccg catcgagacc aacgaatgcc actactgcct cgactgccag      2040
atgacctacc acgaccagga caagtgcccg ccgctggtga caagcgcaa gaagcgcgcg       2100 aagagcgcgc cggcggacaa cgcgcggata cccgcggaga acctctga                  2148
```

<210> SEQ ID NO 15
<211> LENGTH: 2148
<212> TYPE: DNA
<213> ORGANISM: Artificial
<220> FEATURE:
<223> OTHER INFORMATION: codon optimized Pa nosR gene

<400> SEQUENCE: 15

```
atgcgcgcac ttcgtttctc ggcgggctcc tggcgctgcg tctttgcatg gatgttactg       60
cttgttgggt tagctgctca gggtgcagaa ctctccgaac ttgagcgctt acgtatcgca      120
caagtattcc ctgctgttga gcgtatcggg gatcctgaag gtgattatgg ggtgcgccgt      180
ctctccaaag gggaagaaac attggggtac gcgttccaaa cactcagcgt aaccgatatt      240
ccggcctact ccgggaagcc aatcaacctc caggttattt tggatcctca ggctgtcatc      300
cgtgatgcat acgtactcga acatcacgaa ccgatcctct taattggcat ccctgaggaa      360
aagctgcacg ccttctctgc ccgttacgac ggggtacgcg cagaccaacg cgtagtagtg      420
gggcgctcaa gtgatccaca agctgtaaca gtagacgctg tctcgggtgc aacggtgacg      480
gttatggtcg taaatgaaat cgtaatgcgt gcagctcaca cagtggccgt gagtcttggc      540
ctcattgagg accgcggcaa tgtccgtcca aaaccggctc aggtacgtca gcagcctgcg      600
gctacagcca attggtcaga gctgttaggg aatggcgcaa tccgccgcct gcaacttagt      660
cgcgggcaga ttgatgatgc gttcaagggg agcgaagccg agggtatcgg cgaagcagat      720
gccgcgcatc gcgatgaacc tttcatcgac ttgtacagcg ccctgcttaa tccgccagcg      780
gtaggccgct ccctcctggg ggacaaccaa taccgcgagc ttatgcgtc tctcaaacct       840 ggtgaatacg cttttgtggt gcttggtgat ggtgagtact cttttaaagg gtctggctac      900
gttcgcggcg ggattttga ccgcgttcag ttgcgccaat cggtgatat tatttcgttt        960 cgcgacttgg attatcaacg cttgtccgac gtgtatgccg aaggtatgcc ggaattccgc      1020
```

```
gaaatggcaa tctttgtcgc gcgcgcgtca caacgttttg accctggttc tccgtggacc   1080
ctggagttat tagtacgccg tcaaaccggg ccggtggccg gcgtgtttac ctcctttgag   1140
cttgcgtgcc aaacaccaga ggagtatctt gaacgccctc aacctacagc agaagagctt   1200
gcggccctgg aagaggctgc gcgcccactt tggcttcgcg tttggtacca gaagagtttt   1260
caggtcggcg tgctctgcac ggcattggtg ttactgcttg cgatcttatt tcttcaggat   1320
cgtcttgtgc gtcgtccgcg cttgatgcaa cgtcttcgca cggggtacct ggctttcacg   1380
ttagtttact taggttggta cagcctcggt caattgagtg ttgtcaatgt tcttactttt   1440
gttcatgctt tgttcgaggg ttttcgctgg gaattgtttc tttctgatcc gctcctgttt   1500
attctttgga cgtttacggc cgcctcattg ttgctgtggg gccgcggcgt cttttgtggg   1560
tggttatgtc cttttggtgc tttacaagag ttgctcaacg agctggcacg taagctgcgc   1620
gtgccgcaat tccaagttcc gtttgcggtt catgagcgct tgtgggctat taagtatatc   1680
attctgttag ttctgttcgg cttaagctta gagagcttgg cattagctga gcaagctgca   1740
gaagtcgaac catttaagac agcaattacc ttagggtttg atcgccagtg gtggttcgtg   1800
gcgtacgccg tcgcattatt ggtggtcaat ctgtttacac gtaaggtcta ctgccgctat   1860 cttttgtccgc tcggggctgc actggcaatt ccagccaaag ctcgtttgtt tgactggctc   1920
aaacgtcgcg ctgaatgcgg gcgcccatgc cagttgtgcg cccgcgagtg tgaaatccaa   1980
gcaattcacc cggacggtcg cattgagacg aatgagtgtc actattgcct cgattgtcaa   2040
atgacatacc atgatcagga taagtgtccg cctcttgtga acaagcgcaa aaagcgcgcc   2100
aaatcagctc cggcggataa cgcacgtatc cctgcggaga acctctga             2148
```

<210> SEQ ID NO 16
<211> LENGTH: 729
<212> TYPE: PRT
<213> ORGANISM: Pseudomonas versutus
<400> SEQUENCE: 16

```
Met Lys Ile Leu Arg Leu Val Leu Thr Ile Ala Ser Leu Leu Leu Pro
1               5                   10                  15

Ala Leu Pro Ala Ala Ala Glu Ser Val Leu Ala Gln Leu Leu Pro Glu
            20                  25                  30

Gln Asn Ala Gly Glu Leu Val Pro Gly Ala Asp Gly Phe Gly Pro Ile
        35                  40                  45

Arg Ala Asp Leu Ala Val Ala Pro Val Leu Lys Gly Gly Glu Thr Val
    50                  55                  60

Ala His Ala Phe Val Thr Ser Asp Phe Val Gly Thr Thr Gly Tyr Ser
65                  70                  75                  80

Gly Lys Pro Ile His Thr Leu Val Ala Leu Asp Lys Asp Ala Lys Val
                85                  90                  95

Ala Gly Val Arg Leu Val Lys His Ser Glu Pro Ile Val Leu Ile Gly
            100                 105                 110

Ile Pro Glu Ala Lys Val Lys Ala Leu Val Glu Gly Tyr Arg Gly Leu
        115                 120                 125

Asp Leu Val Ala Glu Ala Gln Ser Gly Gly Thr Ala His Glu Val Glu
    130                 135                 140

Ile Ile Ser Gly Ala Thr Val Thr Val Met Val Ile Asp Asp Ser Ile
145                 150                 155                 160

Val Arg Ser Gly Leu Lys Val Ala Arg Ala Leu Gly Leu Gly Gly Leu
                165                 170                 175
```

```
Ala Ala Glu Thr Val Ala Ala Gly Pro Lys Phe Glu Ile Asp Pro Asp
            180                 185                 190

Ala Ala Pro Ser Ala Asp Trp His Glu Met Glu Gly Asp Gly Thr Leu
        195                 200                 205

Arg Arg Leu Ser Leu Asp Val Gly Gln Val Asn Ala Ala Phe Ala Ala
    210                 215                 220

Asn Pro Asp Arg Arg Ala Ala Glu Arg Ala Leu Ser Glu Ala Pro Asp
225                 230                 235                 240

Thr Thr Phe Ile Glu Met Gln Ala Gly Leu Val Ser Val Pro Ala Ile
                245                 250                 255

Gly Lys Ala Leu Leu Gly Asp Ala Gln Ala Ala Asn Leu Gln Ala Trp
            260                 265                 270

Leu Ala Pro Gly Asp Gln Ala Ile Ala Val Met Gly Arg Gly Leu Tyr
        275                 280                 285

Ser Phe Lys Gly Ser Gly Tyr Val Arg Gly Gly Ile Phe Asp Arg Ile
    290                 295                 300

Val Leu Ile Gln Asp Asp Val Ser Val Arg Phe Arg Asp Arg Asp His
305                 310                 315                 320

Arg Arg Leu Asn Ala Val Ala Ala Asp Gly Ala Pro Asp Phe Thr Glu
                325                 330                 335

Met Asp Leu Phe Lys Ile Pro Ala Ala Ser Gly Phe Asp Pro Thr Lys
            340                 345                 350

Pro Phe Arg Ile Gln Leu Leu Val His Arg Glu Val Gly Pro Ile Glu
        355                 360                 365

Lys Val Phe His Thr Phe Asp Leu Gly Tyr Gln Leu Pro Gln Lys Tyr
    370                 375                 380

Leu Arg Ser Val Ala Ala Pro Ala Pro Ala Pro Glu Ala Ala Ala Pro
385                 390                 395                 400

Val Ala Gln Ser Asp Glu Ser Gln Ala Gln Ala Gln Leu Trp Lys Arg
                405                 410                 415

Ile Trp Leu Asp Ser Lys Pro Lys Ile Ala Gly Leu Ala Ala Met Leu
            420                 425                 430

Leu Val Leu Thr Gly Ala Phe Phe Gln Ser Phe Ala Thr Arg Asn
        435                 440                 445

Glu Arg Ala Phe Tyr Ile Phe Arg Met Gly Phe Leu Thr Val Thr Leu
    450                 455                 460

Ile Phe Leu Gly Trp Tyr Ala Asn Ala Gln Leu Ser Val Val Asn Leu
465                 470                 475                 480

Met Ala Leu Phe Gly Ser Leu Val Asn Gly Phe Ser Trp Gln Ala Phe
                485                 490                 495

Leu Leu Asp Pro Leu Thr Phe Ile Leu Trp Phe Ala Val Ala Ala Ala
            500                 505                 510

Leu Leu Phe Trp Gly Arg Gly Ala Tyr Cys Gly Trp Leu Cys Pro Phe
        515                 520                 525

Gly Ala Leu Gln Glu Leu Thr Asn Gln Ile Ala Arg Lys Leu Arg Ile
    530                 535                 540

Pro Gln Trp Thr Leu Pro Trp Gly Leu His Glu Arg Leu Trp Pro Val
545                 550                 555                 560

Lys Tyr Met Ile Phe Leu Gly Leu Phe Gly Val Ser Leu Met Ser Val
                565                 570                 575

Glu Gln Ala Glu His Leu Ala Glu Val Glu Pro Phe Lys Thr Ala Ile
            580                 585                 590

Ile Leu Lys Phe Ile Arg Ala Trp Pro Phe Val Ala Tyr Ala Ala Ala
```

```
                  595                 600                 605
Leu Leu Ile Ala Gly Leu Phe Val Glu Arg Phe Tyr Cys Arg Tyr Leu
    610                 615                 620

Cys Pro Leu Gly Ala Ala Leu Ala Ile Pro Ala Arg Met Arg Met Phe
625                 630                 635                 640

Asp Trp Leu Lys Arg Tyr His Glu Cys Gly Asn Pro Cys Gln Ile Cys
                645                 650                 655

Ala Gln Gln Cys Pro Val Gln Ser Ile His Pro Thr Gly Glu Ile Asn
            660                 665                 670

Pro Asn Glu Cys Ile Asn Cys Met His Cys Gln Val Leu Tyr Gln Ser
        675                 680                 685

Lys Thr Thr Cys Pro Val Val Ile Arg Lys Leu Lys Arg Arg Glu Ala
    690                 695                 700

Val Ala Ala Gly Ser Thr Pro Lys Leu Gly Gln Pro Pro Ala Gly His
705                 710                 715                 720

Pro Asn Ala Thr Arg Lys Ile Glu Ala
                725

<210> SEQ ID NO 17
<211> LENGTH: 2190
<212> TYPE: DNA
<213> ORGANISM: Pseudomonas versutus

<400> SEQUENCE: 17
atgaagatcc tccgccttgt cctgacgatc gcatcgctgt tgctgccggc cctgccggcc     60
gccgccgaaa gcgtgctggc gcagctgctg ccggagcaga cgcgggcga gctggtgccc    120
ggcgccgacg gtttcggacc gatccgcgcc gatctggccg tggcgccggt gctgaagggg    180
ggcgagaccg tcgcccatgc cttcgtcacc tcggatttcg tcggcaccac cggctattcc    240
ggcaagccca tccatacgct cgtcgcgctg gacaaggacg cgaaggtggc cggcgtccgg    300
ctggtcaagc attccgaacc catcgtgctg atcggcatcc ccgaggccaa ggtcaaggcg    360
ctggtcgagg gctaccgggg ccttgacctc gtggccgagg cgcaatcggg cggcacggcg    420
catgaggtcg agatcatctc gggcgccacg gtcacggtga tggtgatcga cgattccatc    480
gtgcgctcgg ggctgaaggt cgcgcgcgcg ctcggccttg cgggctggc cgccgaaacc    540
gtggccgccg cccgaagtt cgagatcgac cccgacgcgg ccccctcggc cgactggcac    600
gagatggagg cgacggcac cctgcgccgg ctgtcgctgg acgtgggcca ggtgaacgcg    660
gcctttgccg ccaatcccga ccgccgcgcc gccgagcgcg cgctgtccga ggcgccggac    720
accaccttca tcgagatgca ggccgggctg gtctcggtcc cggccatcgg caaggcgctg    780
ctgggcgatg cgcaggccgc gaacctgcag gcctggctgg cgccgggcga ccaggccatc    840
gcggtgatgg gccgcgggct ctacagcttc aagggctcgg gctatgtccg cggcggcatc    900
ttcgaccgca cgtgctgat ccaggacgac gtctcggtgc gcttccgcga ccgcgaccat    960
cgccggctga cgccgtcgc tgccgatggc gcgccggatt tcaccgagat ggacctgttc   1020
aagatccccg cggcttcggg cttcgacccg accaagccct ccgcatcca gctgctggtg   1080
catcgcgagg tcgggccgat cgagaaggtc ttccacacct cgacctgggg ctatcagctg   1140
ccgcagaaat acctgcgcag cgttgccgcc cccgcacccg cgcccgaggc ggcggcaccc   1200
gtggcccagt ccgacgaaag ccaggcccag cgcagctgt ggaagcggat ctggctggat   1260
tccaagccca gatcgccgg gcttgccgcc atgctgctgg tgctgacggg ggcattcttc   1320
ttccagagct tcgcgacccg gaacgagcgc gccttctaca tcttccgcat gggctttctg   1380
```

```
accgtgacgc tgatcttcct gggctggtat gccaatgcgc agctttcggt cgtgaacctg    1440
atggcgctgt tcggcagcct ggtgaacggc ttcagctggc aggccttcct gctggacccg    1500
ctgaccttca tcctgtggtt cgcggtcgcc gccgcgctgc tgttctgggg ccggggcgcc    1560
tattgcggct ggctttgccc cttcggcgcg ctgaagagc tgaccaacca gatcgcgcgc     1620
aagctgcgca tcccgcaatg gacgctgccc tggggcctgc acgagcggct gtggccggtc    1680
aaatacatga tcttcctggg ccttttcggc gtctcgctga tgagcgtcga gcaggccgag    1740
catctggccg aggtcgagcc cttcaagacc gcgatcatcc tgaaattcat ccgcgcctgg    1800
cccttcgtgg cctatgccgc ggcgctgctg atcgccgggc tcttcgtcga gcgcttctat    1860
tgccgctacc tgtgcccgct tggcgcggcg ctggcgatcc cggcgcggat gcgcatgttc    1920
gactggctca agcgctatca cgaatgcggc aatccctgcc agatctgcgc ccagcaatgc    1980
ccggtgcagt cgatccaccc gacgggcgag atcaatccca cgaatgcat caactgcatg     2040 cattgccagg tgctttacca gtccaagacc acctgcccgg tggtgatccg caagttgaaa    2100
cggcgcgagg ccgtggccgc cggcagcacg cccaagctgg ccagccccc ggccggccat     2160 cccaacgcca cccgcaagat cgaagcttga                                     2190
```

<210> SEQ ID NO 18
<211> LENGTH: 2190
<212> TYPE: DNA
<213> ORGANISM: Artificial
<220> FEATURE:
<223> OTHER INFORMATION: codon optimized Pv nosR gene

<400> SEQUENCE: 18

```
atgaaaattt tgcgtcttgt gttaacaatt gcgtcgttgc tcctcccggc tcttcctgcg    60
gcggcggaaa gcgtcttagc ccaattgtta ccagaacaaa atgcagggga actggtacct    120
ggggctgatg gcttcgggcc tattcgtgcg gacctggccg tgccccggt acttaagggg     180 ggtgaaaccg ttgctcacgc atttgtaacc tcggactttg tgggtaccac cggttactca    240
gggaaaccaa ttcacacgct ggtcgcttta gacaaagacg ctaaagttgc aggggtgcgc    300
ctggttaaac attcagagcc tattgtcctg attggtattc ctgaagccaa agtgaaggcc    360
ctcgtggaag gttatcgcgg cctggacctg gttgccgaag ctcaatcggg ggggacggct    420
catgaggtag agattatctc aggggcaaca gttactgtga tggtgattga cgactcgatc    480
gtccgcagtg gtctcaaggt ggcacgcgct ctcggcctcg ggggcttgc ggcagaaact     540 gtggccgccg gccctaagtt tgagatcgac ccagatgcag ccccgtccgc cgattggcac    600
gaaatggagg gggatggcac attacgccgc ctttcgttag acgtcggcca ggttaacgct    660
gccttcgctc gaaccccaga tcgtcgcgcc gcgagcgtg cattgtcaga agcacctgat     720
acaacattca ttgagatgca ggctgggctc gtttcggttc cggcgatcgg taaggccctc    780
ctcggtgacg cccaagcggc aaatttgcaa gcttggttgg cccctggtga ccaggccatt    840
gcggttatgg gccgcggctt atattcgttc aaagggagtg gctacgttcg cggtggtatc    900
ttcgatcgta tcgtattaat ccaagatgac gtgtcagttc gctttcgcga ccgtgatcat    960
cgtcgcctca acgccgtggc gcggacggt gcccgggact tcacagagat ggacctgttc     1020
aaaatcccgg cagcaagtgg cttcgaccca acgaaaccgt tcgcattca acttttagta     1080 catcgcgaag taggccctat tgagaaggtc tttcatactt tcgacctcgg ctatcagctg    1140
cctcaaaaat atctgcgctc ggtcgccgca ccggctccgg ccccagaggc agccgcacct    1200
```

```
gttgcccaaa gcgatgaatc acaggcgcaa gcgcagctct ggaagcgcat ttggctcgat    1260
agtaagccaa aaatcgccgg cttggccgcg atgcttttag ttctcactgg tgcctttttc    1320
tttcagagtt tcgccactcg caacgaacgc gccttctata ttttccgcat gggcttcctc    1380
acagtcactc tgattttttct ggctggtat gctaatgctc aactgagcgt ggtaaatctt    1440
atggcacttt tgggagtttt ggtgaacggg ttctcgtggc aggcttttct cttggatcct    1500
ctcacattca ttttgtggtt cgcagttgcc gcagctcttc tcttttgggg cgtggtgct    1560
tattgtggtt ggctgtgtcc atttggcgca ttacaagaat tgaccaatca aattgctcgt    1620
aagcttcgca ttccgcagtg gaccctgcct tggggcctgc atgagcgctt atggccggta    1680
aagtatatga tcttccttgg tttatttggc gttagtttaa tgtcggtgga acaagcagaa    1740
catttggccg aagtggaacc ttttaaaacg gcaattattc tgaaatttat tcgcgcatgg    1800
ccattcgtcg cttatgcggc tgcgctgctc atcgcaggtt tgttcgtaga acgcttctac    1860
tgccgctatc tgtgtccgtt gggcgcagct ctcgcgattc cggcccgtat gcgtatgttc    1920
gattggctga agcgttatca cgagtgcggt aatccgtgcc agatttgcgc acaacagtgc    1980
ccggtccagt cgatccaccc gaccggggaa attaacccga cgaatgtat taattgcatg    2040
cactgccaag tattatacca atcgaaaacc acttgtccgg tagtcatccg caagctcaag    2100
cgccgtgaag cggttgctgc gggttcaacg ccgaaattgg ggcaacctcc tgccggtcat    2160
ccgaatgcga cacgtaaaat tgaagcgtaa                                      2190
```

<210> SEQ ID NO 19
<211> LENGTH: 434
<212> TYPE: PRT
<213> ORGANISM: Pseudomonas stutzeri

<400> SEQUENCE: 19

```
Met Arg Ala Cys Tyr Thr Leu Ala Leu Thr Ala Leu Met Ile Pro Ala
1               5                   10                  15

Gly Ala Ala Leu Ala Glu Pro Gln Pro Leu Thr Ser Leu Pro Leu Gln
            20                  25                  30

Ala Gln Gly Glu Asn Arg Trp Thr Leu Pro Ala Gly Glu Tyr Ile Gly
        35                  40                  45

Gln Phe Ile Ile Asp Gln Pro Leu Ala Leu His Cys Ala Pro Gly Ala
    50                  55                  60

Val Ile Lys Ala Pro Gly Gln Gly Asn Val Leu Thr Val Arg Ala Ala
65                  70                  75                  80

Asn Val Thr Ile Glu Gly Cys Ala Leu Arg Asp Trp Gly Arg Asp Leu
                85                  90                  95

Thr Ala Met Asn Ala Ala Ile Phe Leu Glu Pro Thr Ala Thr Gly Ala
            100                 105                 110

Gln Ile Arg Asn Asn Asp Leu Gln Gly Pro Phe Gly Ile Trp Ala
        115                 120                 125

Asp Arg Asn Arg Asp Leu Leu Val Glu Gly Asn Arg Ile Glu Gly Asp
    130                 135                 140

Leu Gly Leu Arg Ser Gln Asp Arg Gly Asn Gly Ile His Leu Phe Ser
145                 150                 155                 160

Val Arg Gly Ala Arg Val Ile Asp Asn His Val Trp Asn Thr Arg Asp
                165                 170                 175

Gly Ile Tyr Ile Asp Asn Ser Asn Gly Asn Ser Ile Glu Arg Asn Leu
            180                 185                 190

Phe Glu Asp Leu Arg Tyr Gly Val His Tyr Met Phe Ser His Glu Asn
```

```
                    195                 200                 205
Arg Val Ile Ala Asn Val Thr Arg Arg Thr Arg Thr Gly Tyr Ala Leu
        210                 215                 220

Met Gln Ser Arg Lys Leu Thr Val Ile Gly Asn Arg Ser Glu His Asp
225                 230                 235                 240

Gln Asn Tyr Gly Ile Leu Met Asn Tyr Ile Thr Tyr Ser Thr Leu Lys
                245                 250                 255

Asp Asn Phe Val Thr Asp Val Glu Arg Gly Thr Gly Gly Asp Ser
            260                 265                 270

Met Ile Ser Gly Gly Glu Gly Lys Ala Leu Phe Ile Tyr Asn Ser Leu
        275                 280                 285

Phe Asn Thr Ile Glu Asn Asn His Phe Gln Arg Ser Asp Leu Gly Ile
        290                 295                 300

His Leu Thr Ala Gly Ser Glu Asp Asn Arg Ile Ser Ser Asn Ala Phe
305                 310                 315                 320

Val Gly Asn Ala Gln Gln Val Lys Tyr Val Ala Ile Arg Thr Gln Glu
                325                 330                 335

Trp Ser Val Asp Gly Arg Gly Asn Tyr Trp Ser Asp Tyr Leu Gly Trp
            340                 345                 350

Asp Arg Asn Glu Asp Gly Leu Gly Asp Ile Ala Tyr Glu Pro Asn Asp
        355                 360                 365

Asn Val Asp Arg Leu Leu Trp Met Tyr Pro Gln Val Arg Leu Leu Met
        370                 375                 380

Asn Ser Pro Ser Ile Glu Val Leu Arg Trp Val Gln Arg Ala Phe Pro
385                 390                 395                 400

Val Ile Lys Ser Pro Gly Val Gln Asp Ser His Pro Leu Met Lys Pro
                405                 410                 415

Pro Thr Arg Gly Val Thr Glu Glu Pro Met Asn Thr Thr Gln Arg Pro
            420                 425                 430

His Ser

<210> SEQ ID NO 20
<211> LENGTH: 1305
<212> TYPE: DNA
<213> ORGANISM: Pseudomonas stutzeri

<400> SEQUENCE: 20
atgcgtgcgt gctacaccct ggcgcttacc gcgctcatga ttcccgcggg agccgccctg     60
gcggaaccgc aaccgctcac ctcgctgccg ctgcaagcgc agggcgagaa ccgctggaca    120
ctgcccgccg cgaatacat cggcaattc atcatcgatc aaccgctggc gctgcactgc     180
gcgccgggtg cggtgatcaa ggcgccgggg caaggcaacg tcctgaccgt gcgcgcagcg    240
aacgtgacca tcgaggggtg cgcgctgcgt gactggggc gcgacctcac ggcgatgaac    300
gcggcgatct tcctcgaacc gaccgccacc ggcgcgcaga ttcgcaacaa cgacctgcaa    360
gggccgggct tcggcatctg gccgatcgc aatcgtgacc tgctggtcga aggcaaccgt    420
atcgagggcg acctcggcct gcgttcccag gatcgcggca acggcatcca cctgttctcc    480
gtgcgcggtg ctcgagtcat cgacaaccat gtctggaaca cccgcgacgg catctacatc    540
gacaactcca acggcaacag catcgagcgc aacctgttcg aggacctgcg ctacggcgtg    600
cactacatgt tctcccatga gaaccgcgtg atcgccaacg tcacccgccg caccgcacc     660 ggttacgcgc tgatgcagag ccgcaaactg accgtgatcg gcaaccgctc cgagcacgat    720
cagaactacg gcatcctgat gaactacatc acctactcga ccctcaagga caatttcgtc    780
```

```
accgatgtcg agcgtggcga taccggtggc gacagcatga tcagcggcgg tgaaggcaag    840
gcgctgttca tctacaactc gctgttcaac accatcgaga caaccactt ccagcgcagc     900 gatctgggta tccatctgac cgccggctcg aagacaacc gtatttccag caacgccttc    960
gtcggcaacg cgcagcaggt caagtacgtc gccatacgga cccaggagtg gtcggtcgac   1020
gggcgcggca actactggag cgactacctg gctgggacc gcaacgaaga cggcctgggc    1080
gacatcgcct acgagcccaa cgacaacgtc gatcgcctgc tgtggatgta ccgcaggtg    1140 cgtctgctga tgaacagccc gagcatcgaa gtgctgcgct gggtgcagcg cgcgtttccg    1200
gtgatcaagt caccgggcgt acaggacagc catccgttga tgaagccacc tacccgaggc   1260
gtgacagagg aaccgatgaa cacaacgcag aggccccact catga                    1305
```

<210> SEQ ID NO 21
<211> LENGTH: 1305
<212> TYPE: DNA
<213> ORGANISM: Artificial
<220> FEATURE:
<223> OTHER INFORMATION: codon optimized Ps nosD gene

<400> SEQUENCE: 21

```
atgcgcgctt gctacactct cgcccttacg gcgttaatga ttccggccgg ggcggctctt     60
gcggaaccac agccgcttac ctccttgcct ctgcaagccc agggcgaaaa tcgctggacg    120
ctcccagcag gcgagtacat tggccaattc atcattgacc aacgctggc actccattgt     180 gcacctgggg cggttattaa agctccgggg cagggtaatg tcttgacagt ccgcgcagca    240
aacgtgacaa tcgaggggtg cgcattgcgc gactggggcc gcgacctcac ggccatgaat    300
gcagccatct tcttggaacc taccgccacg ggcgcacaga tccgcaataa cgatttacaa    360
ggcccaggtt tcggcatctg gccgaccgt aatcgtgatt tgcttgtgga aggcaatcgt     420
atcgaaggtg accttggctt gcgttcccag gaccgcggga atggcatcca cctttttctct   480 gtacgtggcg cacgcgtaat tgacaaccat gtttggaaca cacgcgatgg catctatatt     540
gacaactcca acggcaattc tatcgagcgt aatctgtttg aggacttgcg ctacgggta     600 cactatatgt tctcacacga aaaccgcgtt atcgcgaacg tcacccgccg cactcgcaca    660
ggctacgctt taatgcagag tcgcaaattg accgttatcg gcaatcgctc cgaacacgat    720
caaaactatg gattttaat gaactacatt acttatagca ccctcaaaga taattttgtc    780
acggatgtcg aacgcggtga tactggcggg gattctatga tctcagggg tgaaggtaaa    840 gctctcttta tctacaatag tctcttcaat acaattgaaa acaaccactt caacgttcc    900 gatctcggca tccatctgac agccggctca gaggataatc gcatctcctc caacgcattc     960
gtggggaatg ctcagcaagt caaatacgtg gcaatccgta tcaagagtg gagtgtggac    1020 ggccgcggta actactggtc ggattacctt gggtgggatc gcaacgaaga cgggcttggc    1080
gatattgcct atgaacctaa cgacaatgta gaccgtcttc tttggatgta tccacaggtt    1140
cgcttattga tgaatagccc ttcaatcgag gttcttcgtt gggttcaacg tgcctttcct    1200
gtgatcaaaa gccctggtgt ccaggattcc catccgctta tgaaacctcc aacgcgcggt   1260
gtgactgagg aaccatatgaa cacgactcag cgtcctcata gctaa                   1305
```

<210> SEQ ID NO 22
<211> LENGTH: 421
<212> TYPE: PRT
<213> ORGANISM: Pseudomonas aeruginosa

<400> SEQUENCE: 22

```
Met Ala Gly Arg Arg Ala Gly Pro Leu Leu Ala Leu Leu Leu Gly
1               5                   10                  15

Leu Ala Thr Ala Arg Ala Glu Pro Val Asp Gly Leu Pro Leu Arg Ala
            20                  25                  30

Asp Gly Asp Gly Arg Trp Ser Leu Ala Ala Gly Arg Tyr Ala Gly Asn
        35                  40                  45

Phe Val Ile Asp Arg Pro Leu His Leu Arg Cys Glu Ala Gly Ala Glu
    50                  55                  60

Leu Asp Gly Gly His Gly Ser Leu Thr Leu Thr Ser Pro Gly
65              70                  75                  80

Ile Thr Val Glu Gly Cys Arg Leu Arg Asn Trp Gly Arg Asn Leu Thr
                85                  90                  95

Glu Leu Asp Ala Ala Ile Phe Val Gly Lys Ala Ser Gly Ala Val
            100                 105                 110

Ile Arg Gly Asn Asp Leu Arg Gly Ala Gly Phe Gly Val Trp Leu Asp
        115                 120                 125

Ala Thr Ala Gly Ala Gln Val Leu Asp Asn Arg Ile Glu Gly Asp Glu
130                 135                 140

Ser Val Arg Ser Gln Asp Arg Gly Asn Gly Ile His Leu Tyr Ala Val
145                 150                 155                 160

Lys Asp Ala Leu Val Arg Gly Asn Arg Val Ser His Thr Arg Asp Gly
                165                 170                 175

Val Tyr Ile Asp Thr Ser Asn Asp Ser Ser Ile Glu Ala Asn Arg Phe
            180                 185                 190

Glu Asp Leu Arg Tyr Gly Val His Tyr Met Phe Thr His Asn Ser Arg
        195                 200                 205

Val Thr Asp Asn Leu Thr Arg Arg Thr Arg Thr Gly Tyr Ala Leu Met
    210                 215                 220

Gln Ser Arg Lys Leu Thr Val Thr Gly Asn Arg Ser Ile Asp Asp Glu
225                 230                 235                 240

Asn Tyr Gly Ile Leu Met Asn Tyr Ile Thr Tyr Ser Thr Leu Ala Gly
                245                 250                 255

Asn Arg Val Glu Gly Val Arg Ser Gly Ser Thr Gly Asp Ala Met Ile
            260                 265                 270

Ser Gly Ala Glu Gly Lys Ala Leu Phe Ile Tyr Asn Ser Leu Phe Asn
        275                 280                 285

Arg Ile Glu Gly Asn Ser Phe Ala Asp Ser Ala Leu Gly Ile His Leu
    290                 295                 300

Thr Ala Gly Ser Glu Asp Asn Arg Ile Ala Gly Asn Ala Phe Ile Gly
305                 310                 315                 320

Asn Arg Gln Gln Val Lys Tyr Val Ala Ser Arg Glu Gln Glu Trp Ser
                325                 330                 335

Ala Asp Gly Arg Gly Asn Tyr Trp Ser Asp Tyr Leu Gly Trp Asp Arg
            340                 345                 350

Asp Asp Asp Gly Leu Gly Asp Val Ala Tyr Glu Pro Asn Asp Asn Val
        355                 360                 365

Asp Arg Leu Ile Trp Leu Tyr Pro Gln Val Arg Leu Leu Asn Ser
    370                 375                 380

Pro Ser Ile Glu Leu Leu Arg Trp Val Gln Arg Ala Phe Pro Val Val
385                 390                 395                 400

Arg Ser Pro Gly Val Arg Asp Ser His Pro Leu Met Arg Met Pro Ala
                405                 410                 415
```

Ala Glu Pro Arg Pro
            420

<210> SEQ ID NO 23
<211> LENGTH: 1266
<212> TYPE: DNA
<213> ORGANISM: Pseudomonas aeruginosa

<400> SEQUENCE: 23

| | | | | | | |
|---|---|---|---|---|---|---|
| atggccgggc | gccgggcggg | gccgctcctc | gccctgctcc | tgctcggcct | cgccacggcc | 60 |
| cgcgcggagc | cggtcgacgg | cctgccgctg | cgggccgacg | gcgatggccg | ctggagcctg | 120 |
| gcggcgggcc | gctacgccgg | taacttcgtc | atcgaccggc | cgctgcacct | acgctgcgag | 180 |
| gccggcgccg | aactggacgg | cggcggccac | ggcagtctgc | tgaccctgac | cagccccggg | 240 |
| atcaccgtcg | agggctgccg | gctgcgcaac | tgggggcgca | acctgaccga | actcgacgcc | 300 |
| gcgatcttcg | tcggcaaggc | cgccagcggc | gccgtgatcc | gcggcaacga | cctgcgcggc | 360 |
| gcgggcttcg | gcgtctggct | cgacgccacg | gcgggcgcgc | aggtgctcga | caaccgcatc | 420 |
| gagggcgacg | aaagcgtgcg | ctcccaggat | cgcggcaacg | gcatccacct | ctatgcggtg | 480 |
| aaggacgccc | tggtccgcgg | caaccgggtc | agccacaccc | gcgacggggt | ctacatcgac | 540 |
| acctccaacg | acagcagcat | cgaagccaac | cgcttcgagg | acctgcgcta | cggcgtgcac | 600 |
| tacatgttca | cccacaacag | ccgggtgacc | gacaacctga | cccggcgcac | ccgcaccggc | 660 |
| tacgcgctga | tgcagagccg | caagctgacc | gtgaccggca | accgctccat | cgacgacgag | 720 |
| aactacggca | tcctgatgaa | ctacatcacc | tactcgaccc | tggccggcaa | ccgcgtcgag | 780 |
| ggcgtgcgca | gcggcagcac | cggcgacgcg | atgatttccg | gcgccgaggg | caaggcgctg | 840 |
| ttcatctaca | ctcgctgtt | caaccgcatc | gaaggcaaca | gcttcgccga | cagcgccctg | 900 |
| ggcatccacc | tcaccgccgg | ctcggaggac | aatcgcatcg | ccggcaacgc | cttcataggc | 960 |
| aaccgccagc | aggtcaagta | cgtcgccagc | cgcgagcagg | agtggtccgc | cgacggccgc | 1020 |
| ggcaactact | ggagcgacta | cctgggctgg | gaccgcgacg | acgacggtct | cggcgacgtc | 1080 |
| gcctacgagc | ccaacgacaa | cgtcgaccgg | ctgatctggc | tgtacccgca | ggtacgcctg | 1140 |
| ctgttgaaca | gcccgagcat | cgagctgctg | cgctgggtcc | agcgcgcctt | cccggtggtg | 1200 |
| cgctcgcccg | gcgtgcgcga | cagccatccg | ctgatgcgga | tgcccgccgc | ggagccgagg | 1260 |
| ccgtga | | | | | | 1266 |

<210> SEQ ID NO 24
<211> LENGTH: 1266
<212> TYPE: DNA
<213> ORGANISM: Artificial
<220> FEATURE:
<223> OTHER INFORMATION: codon optimized Pa nosD gene

<400> SEQUENCE: 24

| | | | | | | |
|---|---|---|---|---|---|---|
| atggcagggc | gccgtgctgg | gccactgttg | gccctcttat | tactcggtct | cgcaactgct | 60 |
| cgtgctgaac | cggtagatgg | cctcccgtta | cgtgctgatg | gcgacggtcg | ctggtcgctg | 120 |
| gctgccggtc | gttatgccgg | taactttgta | attgatcgtc | ctttgcattt | acgttgcgag | 180 |
| gctggggccg | agcttgatgg | tggtggtcat | gggtcattac | tcaccctgac | gtccccgggt | 240 |
| atcacggttg | aaggctgccg | tctccgcaac | tggggccgta | atttgacaga | gcttgatgca | 300 |
| gctattttg | ttggcaaagc | tgcttccggc | gcagtaatcc | gcggcaacga | cctgcgtggg | 360 |
| gcgggttttg | gggtatggtt | agatgccacc | gccggtgccc | aggtccttga | caaccgcatc | 420 |

```
gaaggtgacg agagcgttcg ctcccaggac cgcggtaatg gtatccatct ctacgccgtc    480
aaggacgccc tcgtacgcgg taatcgcgtg tctcacacac gcgacggtgt ctacatcgac    540
acttccaacg actcctccat tgaggcaaat cgctttgaag accttcgcta tggcgtgcac    600
tacatgttca cccataattc tcgtgtaacc gacaacctta cacgccgcac tcgcacaggc    660
tatgcattga tgcagagccg taaactgaca gtgacgggta accgcagcat tgacgacgaa    720
aattacggca tcctcatgaa ttacatcaca tattctacgc ttgctggcaa tcgcgtggag    780
ggggtgcgta gcggctcgac gggtgacgct atgatctcgg gtgcggaagg gaaggcgctt    840
ttcatctaca attctctctt caaccgtatc gagggcaact ctttcgctga ttctgcatta    900
gggattcacc tcaccgccgg ctcagaggac aatcgtatcg cgggcaacgc ctttatcggc    960
aatcgtcaac aggtaaaata cgtcgcttcg cgcgaacagg agtggtctgc cgatggccgc   1020
ggtaactact ggtctgacta cctcggctgg gatcgcgatg atgatggctt gggtgacgtc   1080
gcatacgaac caaacgacaa tgtggatcgt ttaatttggt tgtacccaca agtccgttta   1140
cttctgaata gcccttccat tgagttactt cgctgggtgc aacgtgcttt cccggtggta   1200
cgcagtccag gtgtgcgcga ttcccaccct ttgatgcgca tgccagccgc ggagcctcgc   1260
ccttaa                                                              1266

<210> SEQ ID NO 25
<211> LENGTH: 443
<212> TYPE: PRT
<213> ORGANISM: Pseudomonas versutus

<400> SEQUENCE: 25
```

Met Arg Ser Leu Leu Thr Leu Ala Leu Ala Leu Leu Leu Ala Trp Pro
1               5                   10                  15

Ala Leu Ala Ala Glu His Val Val Ala Pro Gly Gln Gly Ser Leu Ala
            20                  25                  30

Gln Ala Ile Ala Gly Ala Ala Pro Gly Asp Val Leu Arg Leu Gln Asp
        35                  40                  45

Gly Val His Ala Gly Pro Val Ala Ile Asp Arg Pro Leu Thr Val Thr
    50                  55                  60

Gly Ser Arg Ala Ala Val Val Asp Gly Gln Gly Arg Gly Thr Val Val
65                  70                  75                  80

Thr Ile Ala Ala Pro Asp Val Thr Leu Gln Gly Phe Ser Val Thr Gly
                85                  90                  95

Ser Gly Met Ala Asn Lys Asp Leu Asp Ala Gly Val Lys Ile Leu Lys
            100                 105                 110

Gly Ala Asp Arg Ala Gln Val Arg Gln Leu Arg Leu Thr Gly Asn Met
        115                 120                 125

His Gly Ile Asp Val His Gly Gly Arg Asp Ala Gln Val Val Gly Asn
    130                 135                 140

Glu Ile Ile Gly Thr Arg Asp Pro Arg Met Asn Glu Arg Gly Asn Gly
145                 150                 155                 160

Ile Tyr Val Trp Asn Ser Pro Gly Thr Leu Val Gln Gly Asn Ser Val
                165                 170                 175

Arg Tyr Gly Arg Asp Gly Ile Phe Ser Asn Ala Ser Asp Ser Ala
            180                 185                 190

Tyr Arg Asp Asn Leu Phe Arg Asp Leu Arg Phe Ala Val His Phe Met
        195                 200                 205

Tyr Thr Arg Asn Thr Glu Val Ser Gly Asn Val Ser Ile Gly Asn His

```
                210             215             220
Leu Gly Phe Ala Ile Met Phe Ser Asp Arg Ala Val Ile Arg Asp Asn
225                 230                 235                 240

Arg Ser Leu Gly Asp Arg Glu His Gly Leu Met Leu Asn Tyr Ala Asn
            245                 250                 255

Asn Ala Asp Val Thr Gly Asn Leu Ile Arg Gly Thr Lys Lys Cys
                260                 265                 270

Leu Phe Ile Tyr Asn Ala His Lys Asn Leu Ile Trp Asp Asn Arg Phe
        275                 280                 285

Gln Asp Cys Gly Ile Gly Ile His Phe Thr Ala Gly Ser Glu Arg Asn
    290                 295                 300

Val Leu Thr Ala Asn Ala Phe Val Gly Asn Arg Glu Gln Val Lys Tyr
305                 310                 315                 320

Val Gly Thr Arg His Ile Glu Trp Ser His Glu Gly Arg Gly Asn Phe
                325                 330                 335

Trp Ser Asp His Pro Gly Phe Asp Leu Asn Gly Asp Gly Ile Ala Asp
            340                 345                 350

Gly Val Tyr Arg Pro Asn Asp Leu Met Asp His Ile Leu Trp Ser Gln
        355                 360                 365

Pro Ala Ala Ala Leu Leu Thr Gly Ala Pro Ala Val Gln Leu Ile Arg
    370                 375                 380

Trp Ser Gln Gln Ser Phe Pro Ala Thr Leu Pro Gly Gly Val Gln Asp
385                 390                 395                 400

Ser Ala Pro Leu Met Arg Pro Leu Thr Ile Pro Val Pro Pro Glu Ile
                405                 410                 415

Ala Ala Tyr Glu Ala Glu Val Ala Gly Arg Trp Ala Lys Gly Thr Tyr
            420                 425                 430

Asp Asp Ile Asp Pro Asp Leu Thr Ser His
        435                 440

<210> SEQ ID NO 26
<211> LENGTH: 1332
<212> TYPE: DNA
<213> ORGANISM: Pseudomonas versutus

<400> SEQUENCE: 26
atgcgcagcc tgctgaccct tgcccttgcc ctgctgcttg cctggcccgc gctcgcggcc      60
gagcatgtcg tggcgccggg ccagggcagc cttgcccaag ccatcgccgg ggccgccccc     120
ggcgatgtgc tgcgactgca ggacggggtc atgccggcc cgtcgccat cgaccgtccc      180 ttgaccgtca ccggcagccg tgccgcggtg gtggacgggc agggacgggg cacggtcgtc     240
accatcgccg cgcccgacgt caccttgcag ggcttttccg tcacgggctc gggcatggcg     300
aacaaggatc tggacgccgg ggtcaagatc ctcaagggcg ccgaccgggc gcaggtgcgg     360
cagttgcggc tgaccgggaa catgcacggc atcgacgtgc atggcggccg cgacgcccag     420
gtcgtcggca acgagatcat cggcacccgc gacccgcgca tgaacgagcg cggcaacggc     480
atctatgtct ggaacagccc cggcacgctg gtgcagggca attccgtccg ctacggccgc     540
gacggcatct tttcgaacgc cagcggcgac agcgcctatc gcgacaacct gtttcgcgac     600
ctgcgctttg ccgtgcattt catgtatacc cgcaacaccg aggtgtcggg caatgtcagc     660
atcggcaacc acctgggctt cgccatcatg ttctcggacc gggcggtgat ccgcgacaac     720
cgcagcctgg gcgaccgcga gcatgggctg atgctgaact atgccaacaa tgccgacgtg     780
accggcaacc tgatccgcgg cggcaccaag aaatgcctgt tcatctataa cgcccacaag     840
```

```
aacctgatct gggacaaccg cttccaggat tgcggcatcg gcatccactt caccgccggg    900
tccgagcgca acgtgctgac cgcaaacgcc tttgtcggca atcgcgagca ggtgaaatac    960
gtgggcaccc gccatatcga atggagccac gaggggcgcg gcaatttctg gtccgaccat   1020
ccgggcttcg acctgaacgg cgacggcatc gccgacggcg tctatcgccc caacgacctg   1080
atggaccata tcctgtggtc gcagcccgcc gccgcgcttc tgaccggcgc ccccgccgtg   1140
cagctgatcc gctggagcca gcagagcttt cccgccaccc tgccgggcgg cgtgcaggac   1200
agcgcgcccc tgatgcgacc cctgaccatc cccgtcccgc ccgagatcgc ggcctacgag   1260
gccgaggtcg cggggcgttg ggcaaaagga acctacgatg acatcgaccc tgacgatctc   1320
acgtctcact aa                                                       1332
```

<210> SEQ ID NO 27
<211> LENGTH: 1332
<212> TYPE: DNA
<213> ORGANISM: Artificial
<220> FEATURE:
<223> OTHER INFORMATION: codon optimized Pv nosD gene

<400> SEQUENCE: 27

```
atgcgtagtc ttttgacact tgcgctggca ttgctcttag cttggccggc attggcggca     60
gagcacgttg ttgccccggg tcagggttcc ttagcccagg ctatcgcggg tgctgctcca    120
ggcgatgtgc ttcgcttgca agacggggta catgcggggc cagtagctat tgatcgtccg    180
ttgactgtca cgggcagccg cgctgcggtg gttgacggtc aaggccgtgg tacggttgta    240
actatcgccg caccggatgt tacactgcaa gggttctcgg taacggggtc tgggatggct    300
aataaggacc ttgatgccgg ggtgaaaatt ttaaaggggg cagatcgtgc gcaggtgcgc    360
caattacgct tgacggggaa catgcatggt atcgacgtcc atggggggcg cgacgcgcaa    420
gtcgttggta acgaaattat cggtactcgc gacccacgca tgaatgagcg cggtaacggt    480
atctatgtat ggaatagccc gggcacttta gttcaaggga atagcgttcg ctacgggcgc    540
gatggcatct ttagcaacgc gtcgggcgat tctgcatacc gcgataattt gttccgtgac    600
ctgcgtttcg ctgttcactt tatgtataca cgcaatactg aggtttctgg taacgtctcc    660
atcgggaatc atcttgggtt cgcgattatg ttctccgacc gcgctgttat tcgcgacaat    720
cgctctctgg gtgatcgtga gcatggcctc atgcttaatt acgcgaataa cgccgatgtc    780
accggcaatt taatccgcgg tggtactaag aaatgcctct tcatctataa cgcacacaag    840
aacttgatct gggacaatcg tttccaagac tgtgggatcg gcatccactt tacggccggt    900
tccgaacgca atgttttaac ggctaacgcg tttgtaggta atcgtgagca ggtaaagtac    960
gtcgggacac gtcacattga gtggtctcac gaaggtcgcg gtaacttctg gtctgatcat   1020
cctgggtttg acctcaatgg tgatggtatt gcagatggtg tctaccgccc aaatgatctt   1080
atggaccata tcctttggag tcaacctgct gcagcacttc ttaccggggc acctgctgta   1140
cagttgatcc gttggtcaca gcaatcattc ccagcgacgt tgccgggggg tgtgcaagac   1200
tccgcaccac ttatgcgccc gctcactatc ccagtcccac cagagatcgc ggcgtatgaa   1260
gcagaggtag cgggtcgttg ggcaaagggc acgtatgacg acattgaccc agacgattta   1320
actagtcatt ga                                                       1332
```

<210> SEQ ID NO 28
<211> LENGTH: 308
<212> TYPE: PRT

<213> ORGANISM: Pseudomonas stutzeri

<400> SEQUENCE: 28

```
Met Asn Ala Val Glu Ile Gln Gly Val Ser Gln Arg Tyr Gly Asn Met
1               5                   10                  15

Thr Val Leu His Asp Leu Asn Leu Asn Leu Gly Glu Gly Glu Val Leu
            20                  25                  30

Gly Leu Phe Gly His Asn Gly Ala Gly Lys Thr Thr Ser Met Lys Leu
        35                  40                  45

Ile Leu Gly Leu Leu Gln Ala Ser Glu Gly Arg Val Gln Val Leu Gly
50                  55                  60

Arg Asp Pro Arg Thr Thr Asp Val Arg Arg His Leu Gly Tyr Leu Pro
65                  70                  75                  80

Glu Asn Val Thr Phe Tyr Pro Gln Leu Thr Gly Arg Glu Thr Leu Arg
                85                  90                  95

His Phe Ala Arg Leu Lys Ser Thr Pro Leu Gly Gln Val Asp Asp Leu
            100                 105                 110

Leu Glu Gln Val Gly Leu Ala His Ala Ala Asp Arg Arg Val Lys Thr
        115                 120                 125

Tyr Ser Lys Gly Met Arg Gln Arg Leu Gly Leu Ala Gln Ala Val Leu
130                 135                 140

Gly Glu Pro Arg Leu Leu Leu Leu Asp Glu Pro Thr Val Gly Leu Asp
145                 150                 155                 160

Pro Ile Ala Thr Gln Glu Leu Tyr Leu Leu Ile Asp Arg Leu Arg Gln
                165                 170                 175

Thr Gly Thr Ser Val Ile Leu Cys Ser His Val Leu Pro Gly Val Glu
            180                 185                 190

Ala His Ile Asn Arg Ala Ala Ile Leu Ala Lys Gly Arg Leu Gln Ala
        195                 200                 205

Ile Gly Ser Leu Lys Gln Leu Arg Ser Glu Ala Gly Leu Pro Val Arg
210                 215                 220

Ile Arg Ala Ser Gly Ile Ser Gln Ser Glu Ala Trp Leu Glu Arg Trp
225                 230                 235                 240

Ala Asn Ala Gly His Ser Ala Gln Arg Leu Gly Glu Asp Gly Val Glu
                245                 250                 255

Val Ile Ala Ile Asn Gly His Lys Leu Pro Leu Leu Arg Glu Leu Leu
            260                 265                 270

Gly Glu Ser Glu Pro Asp Asp Val Glu Ile His Gln Pro Ser Leu Glu
        275                 280                 285

Asp Leu Tyr Arg Tyr Tyr Met Glu Arg Ala Gly Asp Val Gln Ala Ala
290                 295                 300

Glu Gly Arg Val
305
```

<210> SEQ ID NO 29
<211> LENGTH: 927
<212> TYPE: DNA
<213> ORGANISM: Pseudomonas stutzeri

<400> SEQUENCE: 29

```
atgaatgccg tcgagatcca gggcgtcagc cagcgttacg gcaacatgac cgtgttgcat      60
gatttgaacc tgaacctcgg cgaaggcgag gtactggggc tgttcggcca taacggcgcc     120
ggcaagacca ccagcatgaa actgattctc ggcctgctgc aggccagcga agggcgcgtc     180
caggtactgg gtcgcgatcc gcgcaccacc gacgtgcgcc gtcacctggg ctatctgccg     240
```

```
gagaacgtca ccttctatcc gcaactgacg gggcgcgaga ccctgcgtca tttcgcgcgc    300
ctgaagagca cgccgctggg ccaggtggac gatctgctcg agcaggtcgg cctcgcccac    360
gccgccgatc gccgcgtgaa gacctattcc aagggcatgc ccagcggct cggcctggcc     420 caggcggtgc tcggcgagcc gcgcctgctg ctgctcgacg aacccaccgt ggggctcgac    480
cccatcgcca cccaggagct ctacctgctg atcgatcggc tgcgccagac gggtaccagc    540
gtgatcctct gttcccacgt gctgcccggc gtggaggcgc atatcaaccg tgcggcgatt    600
ctcgccaagg ggcgcctgca ggccatcggc agcctcaagc agctgcgcag cgaggccggc    660
ctgccggtgc gtatccgcgc cagtggcatc agtcagagcg aggcctggct ggagcgctgg    720
gccaatgcgg ggcactcggc gcagcgtctc ggcgaggatg cgtcgaggt gatcgccatc     780 aacggccaca gctgccgtt gctgcgtgag ctgctcgggg aaagcgaacc cgacgatgtg     840
gaaatccacc agccttcgct ggaggatctg taccgctatt acatggagcg cgccggcgat    900
gtgcaggccg cggagggcag ggtatga                                        927
```

<210> SEQ ID NO 30
<211> LENGTH: 927
<212> TYPE: DNA
<213> ORGANISM: Artificial
<220> FEATURE:
<223> OTHER INFORMATION: codon optimized Ps nosF gene

<400> SEQUENCE: 30

```
atgaacgctg tggaaattca aggggtttct cagcgctatg gaatatgac tgtactgcat       60 gatttgaact tgaacttagg ggaaggtgaa gtgcttgggt tattcggtca caatggcgct    120
gggaagacaa catcaatgaa acttatcctg ggcctcctgc aagcatccga gggtcgtgtc    180
caggtgctgg gccgtgaccc acgtaccact gatgtgcgtc gccacctcgg ttacttacct    240
gaaaatgtca cgttttatcc tcaacttaca gggcgcgaga ctttacgtca cttcgccccgt    300 ctgaagtcca cccctctggg ccaagtggac gatctgctgg agcaagttgg tctcgctcac    360
gctgcagacc gccgcgtgaa aacctactca aaaggtatgc ccaacgcctt gggcttagcg    420
caggcggtac tgggtgagcc tcgccttctg ctgctggatg aaccaactgt tgggttggac    480
cctattgcga cgcaagagct ctatctctta attgatcgcc tccgtcaaac tggtacgtcg    540
gttatcctgt gttcacacgt tcttccaggt gtagaggctc acattaatcg cgcagcgatc    600
cttgctaagg gtcgcctcca agccatcggg tcactcaaac aattacgcag cgaagccggg    660
ttacctgtcc gtattcgtgc ctcgggtatt tcccagagtg aggcctggtt agagcgttgg    720
gcgaatgcgg ggcattcggc gcaacgttta ggcgaggatg cgttgaagt gattgcgatc     780 aatgggcaca aactgccatt gctccgtgag ttattggggg aatcagaacc agacgacgtg    840
gaaattcacc aaccgtcgct ggaagatctg tatcgctact atatggaacg tgcaggtgac    900
gtgcaggccg cagaagggcg cgtataa                                        927
```

<210> SEQ ID NO 31
<211> LENGTH: 304
<212> TYPE: PRT
<213> ORGANISM: Pseudomonas aeruginosa

<400> SEQUENCE: 31

```
Met Ser Leu Val Glu Ile Asp Gly Ala Thr Leu Arg Tyr Gly Ala Leu
1               5                   10                  15

Thr Ala Leu Ser Gly Leu Asp Leu Arg Leu Glu Pro Gly Glu Val Leu
```

```
            20                  25                  30
Gly Leu Leu Gly His Asn Gly Ala Gly Lys Thr Thr Thr Ile Lys Leu
             35                  40                  45

Val Leu Gly Leu Leu Ala Pro Ser Glu Gly Arg Val Arg Val Leu Gly
 50                  55                  60

His Asp Ala Arg Ser Leu Glu Ala Arg Arg Gln Leu Gly Tyr Leu Pro
 65                  70                  75                  80

Glu Asn Val Thr Phe Tyr Pro Gln Leu Ser Gly Ala Glu Thr Leu Arg
                 85                  90                  95

His Phe Ala Arg Leu Lys Gly Val Ala Pro Ala Glu Ala Ala Arg Leu
            100                 105                 110

Leu Glu Gln Val Gly Leu Gly His Ala Ala Arg Arg Leu Lys Thr
            115                 120                 125

Tyr Ser Lys Gly Met Arg Gln Arg Leu Gly Leu Ala Gln Ala Leu Leu
            130                 135                 140

Gly Glu Pro Arg Leu Leu Leu Asp Glu Pro Thr Val Gly Leu Asp
145                 150                 155                 160

Pro Leu Ala Thr Val Glu Leu Tyr Gln Leu Leu Asp Arg Leu Arg Gly
                165                 170                 175

Gln Gly Thr Gly Ile Val Leu Cys Ser His Val Leu Pro Gly Val Glu
            180                 185                 190

Thr His Ile Asp Arg Ala Ala Ile Leu Ala Gly Gly Arg Leu Gln Val
            195                 200                 205

Ala Gly Ser Leu Ala Glu Leu Arg Arg Lys Ala Ala Leu Pro Thr Arg
210                 215                 220

Val Arg Leu Ala Ser Pro His Asn Pro Gln Trp Leu Glu Arg Trp His
225                 230                 235                 240

Arg Ala Gly Leu Ala Ala Arg Arg Leu Asp Asp Gln Arg Ile Glu Val
                245                 250                 255

Leu Leu Asp Asp Ala Glu Arg Asp Gly Val Leu Glu Ala Leu Leu Ala
            260                 265                 270

Ala Arg Glu Phe Asp Leu Glu Ile Leu Pro Pro Ser Leu Glu Asp Leu
            275                 280                 285

Tyr Arg His His Met Ser Pro Ala Pro Ala Gly Ala Thr Pro Cys Pro
            290                 295                 300

<210> SEQ ID NO 32
<211> LENGTH: 915
<212> TYPE: DNA
<213> ORGANISM: Pseudomonas aeruginosa

<400> SEQUENCE: 32
gtgagcctgg tcgagatcga cggcgcgacc ctgcgctacg gcgccctcac cgccctgagc      60
gggctcgacc tgcgcctgga gcccggcgag gtgctcggcc tgctcggcca caacggcgcc     120
ggcaagacca ccaccatcaa gctggtcctc ggcctgctgg cccccagcga aggccgcgtg     180
cgggtcctcg gccacgatgc gaggagcctg gaggcgcgcc gccagctcgg ctacctgccg     240
gagaacgtga ccttctaccc gcagctcagc ggcgcggaaa ccctgcgcca cttcgcccgc     300
ctcaagggcg tggcgccggc cgaagccgcg cgcctgctgg aacaggtcgg cctcggccat     360
gccgccaggc ggcgcctgaa aacctactcg aagggcatgc gccagcgcct cggcctggcc     420
caggcgctgc tcggcgaacc gcgcctgctg ctgctcgacg aaccgacggt gggcctcgac     480
ccgctggcca ccgtcgagct ctaccaattg ctcgaccgcc tgcgcggcca gggcaccggg     540
```

```
atcgtcctttt gctcccatgt gctgcccggc gtcgagacgc acatcgaccg cgccgcgatt      600
ctcgccggcg gccgcctgca agtggccggc agcctcgccg aattgcgccg caaggcggct      660
ctgccgaccc gcgtgcgcct ggccagcccg cataacccgc agtggctcga acgctggcac      720
cgggccggcc tggcggcgcg gagactggac gaccagcgca tcgaggtact gctggacgat      780
gccgagcgcg acggcgtgct ggaagcgctg ctggccgcgc gcgagttcga cctggaaatc      840
ctgccgccgt cgctggagga cctctatcgc caccacatgt ccccgcccc cgccggagcc      900 acgccatgcc cgtag                                                       915
```

<210> SEQ ID NO 33  
<211> LENGTH: 915  
<212> TYPE: DNA  
<213> ORGANISM: Artificial  
<220> FEATURE:  
<223> OTHER INFORMATION: codon optimized Pa nosF gene

<400> SEQUENCE: 33

```
atgagccttg tggaaattga cggtgcgact ttacgctacg gggcgctcac tgcgctttct       60
ggcttggatt tacgcttaga gccaggggaa gtcttaggct tattagggca taacggcgct      120
ggcaagacta caacgatcaa gcttgttctc gggttgctcg cgccgagcga aggccgcgtc      180
cgtgtcctcg gcatgatgc gcgcagtttg aagctcgcc gccagttagg ttatctgcca        240
gagaacgtga cctttatcc tcaattaagt ggggcggaga ctttacgcca tttcgctcgt       300
ttaaagggtg tagcccctgc cgaggctgca cgtcttctgg agcaagtcgg tttaggtcac      360
gcggcgcgcc gccgtcttaa aacgtactct aaagggatgc gccagcgctt gggcctcgca      420
caggccctgc ttggggagcc gcgccttctt ttgttagatg aaccgacggt aggtttggac      480
ccacttgcga ccgtggagtt atatcaactc ttggatcgcc ttcgtgggca ggggaccggg      540
atcgttttat gtagtcatgt tctgccaggg gttgagactc atatcgatcg cgctgctatt      600
ctggcaggcg gccgtcttca ggtcgcaggt tcgcttgcag aattacgccg taaagctgct      660
ttgccaaccc gcgttcgtct cgcttcaccg cacaatcctc aatggttgga acgctggcac      720
cgtgctggtc tggcagcccg ccgcttagac gaccaacgca tcgaggtatt attagacgat      780
gcggagcgcg atggtgtact tgaggctctg ctggcggccc gtgaatttga cctggaaatc      840
ctgccaccga gcttagaaga tctgtatcgc caccacatgt ccccagcgcc ggcgggtgca      900
acgccatgtc catga                                                       915
```

<210> SEQ ID NO 34  
<211> LENGTH: 299  
<212> TYPE: PRT  
<213> ORGANISM: Pseudomonas versutus

<400> SEQUENCE: 34

```
Met Thr Ser Thr Leu Thr Ile Ser Arg Leu Thr Lys Arg Phe Gln Thr
1               5                   10                  15

Val Glu Ala Leu Ala Glu Val Ser Leu Asp Leu Gly Pro Gly Met Arg
            20                  25                  30

Val Ala Leu Leu Gly His Asn Gly Ala Gly Lys Ser Thr Met Met Lys
        35                  40                  45

Ile Ile Leu Gly Leu Ile Pro Phe Asp Ala Gly Glu Val Arg Val Cys
    50                  55                  60

Gly Ala Ala Pro Gly Ser Ala Gln Ala Arg Met Gln Val Ala Tyr Leu
65                  70                  75                  80
```

Pro Glu Asn Ala Ala Phe His Pro Ala Leu Thr Gly Glu Glu Gln Ile
             85                  90                  95

Arg His Tyr Leu Ser Leu Arg Gly Glu Ser Pro Arg Arg Ala Met Glu
        100                 105                 110

Leu Leu Glu Arg Val Gly Leu Ala Lys Ala Ala Arg Arg Ile Gly
        115                 120                 125

Thr Tyr Ser Lys Gly Met Arg Gln Arg Val Gly Leu Ala Gln Thr Leu
        130                 135                 140

Ile Gly Arg Pro Arg Leu Val Leu Asp Glu Pro Thr Ser Gly Leu
145                 150                 155                 160

Asp Pro Val Ser Arg Arg Asp Phe Tyr Ala Leu Leu Asp Gly Leu Ala
                165                 170                 175

Ala Glu Gly Ala Ala Ile Leu Leu Ser Ser His Val Leu Thr Glu Val
            180                 185                 190

Glu Ala Arg Thr Asp Arg Ile Leu Ile Leu Ser Gln Gly Arg Leu Val
        195                 200                 205

Ala Glu Gly Thr Leu Ala Glu Leu Arg Arg Arg Ala Ala Leu Pro Val
        210                 215                 220

Gly Leu Thr Val Val Pro Ala Pro Gly Ala Ala Glu Ala Leu Ala Ala
225                 230                 235                 240

Ala Leu Pro Gln Ala Arg Leu Ala Gly Asp Gly Thr Leu His Leu Ala
                245                 250                 255

Cys Ala Gln Asp Glu Lys Leu Gly Leu Leu Ala Arg Ile Ala Gly Leu
            260                 265                 270

Gly Gly Gln Val Ala Asp Leu Asp Val Ile Pro Pro Ser Leu Glu Asp
        275                 280                 285

Ile Tyr Ser His Phe Ser Arg Arg Asp Gly Gln
        290                 295

<210> SEQ ID NO 35
<211> LENGTH: 900
<212> TYPE: DNA
<213> ORGANISM: Pseudomonas versutus

<400> SEQUENCE: 35

| | | |
|---|---|---|
| atgacatcga cccctgacgat ctcacgtctc actaagcgct tccagaccgt cgaggcgctg | 60 |
| gccgaggtct cgctggacct ggggccgggg atgcgcgtcg cgcttttggg ccataacggc | 120 |
| gcgggcaagt ccacgatgat gaagatcatc ctgggcctga tccccttga cgcgggcgag | 180 |
| gtccgggtct gcggcgccgc gcccggctcg gcccaggcgc ggatgcaggt ggcctatctg | 240 |
| ccggaaaacg ccgccttcca cccggccctg accggagagg agcagatccg ccactacctt | 300 |
| tccctgcgcg gcgaaagccc cgcgccggcc atggaactgc tggagcgggt ggggctggcc | 360 |
| aaggccgcgc gccgccgcat cggcacctat tccaagggca tgcgccagcg cgtcggcctg | 420 |
| gcccagacgc tgatcgggcg gccgcggctt ctggttctgg acgagccgac ctcggggctc | 480 |
| gacccggtgt cgcggcgcga cttctatgcg ctgctcgacg gctggcggc cgaggggcg | 540 |
| gcgatcctct tgtcctcgca tgtgctgacc gaggtcgagg cccgcaccga ccgcatcctg | 600 |
| atcctgtcgc agggccggct ggtggccgag ggcacgctgg ccgagttgcg ccgccgcgcc | 660 |
| gccctgccgg tggggctgac cgtggtcccc cgcgccggcg cggccgaggc gctggccgcc | 720 |
| gcgttgccgc aggcgcggct ggcgggcgac ggcacgctgc acctggcctg cgcgcaggac | 780 |
| gaaaagctgg gcctgctggc gcgcatcgcc gggcttggcg gccaggtcgc ggacctggac | 840 |
| gtgatcccgc ccagcctcga ggacatctac agccatttca gccggaggga cgggcaatga | 900 |

<210> SEQ ID NO 36
<211> LENGTH: 900
<212> TYPE: DNA
<213> ORGANISM: Artificial
<220> FEATURE:
<223> OTHER INFORMATION: codon optimized Pv nosF gene

<400> SEQUENCE: 36

```
atgacaagta cactgacgat tagccgctta actaaacgtt ccagaccgt agaggcatta      60
gctgaagtta gtctcgacct cggcccgggc atgcgcgtag cgcttttggg ccataatggt     120
gcgggtaaat caacaatgat gaaaatcatt ttggggctca tcccgtttga cgctggcgag    180
gtccgcgtct gcggggccgc cccagggtca gctcaagccc gcatgcaagt agcatactta    240
ccagagaacg ctgctttcca ccctgcactt actggtgaag agcaaattcg ccattattta    300
tcactccgcg gggagtctcc acgtcgtgct atggaattgc tggagcgcgt tgggttagct    360
aaggccgcac gccgtcgtat cggtacgtat tcaaagggta tgcgtcaacg tgtaggcttg    420
gcccaaacgc ttatcggtcg cccgcgcctc ctcgtcttag atgagccaac ctcaggtctg    480
gacccggtga gccgccgcga ctttatgcg ttactgacg gcctcgctgc tgagggtgct    540
gccattctcc tctccagcca tgttctcaca gaggtcgaag cgcgtaccga ccgtattta    600
atcctgagcc aaggccgcct tgtggccgag ggtacgttag cagagttgcg ccgtcgcgca    660
gctttgccag ttggccttac ggtcgtacca gcgccaggtg ctgctgaagc ccttgcagca    720
gcgctgcctc aagcccgtct ggcaggtgat gggacgctgc atctcgcatg tgcacaagat    780
gagaaattgg ggttactggc tcgtatcgcc gggttagggg gtcaagtcgc cgatctggac    840
gtaatcccgc cttctctcga agatattat tcacactta gtcgccgcga cgggcagtaa    900
```

<210> SEQ ID NO 37
<211> LENGTH: 275
<212> TYPE: PRT
<213> ORGANISM: Pseudomonas stutzeri

<400> SEQUENCE: 37

```
Met Asn Gln Val Trp Asn Ile Ala Arg Lys Glu Leu Ser Asp Gly Leu
1               5                   10                  15

Arg Asn Arg Trp Leu Leu Ala Ile Ser Leu Leu Phe Ala Val Leu Ala
            20                  25                  30

Val Gly Ile Ala Trp Leu Gly Ala Ala Ala Ser Gly Gln Val Gly Phe
        35                  40                  45

Thr Ser Ile Pro Ala Thr Ile Ala Ser Leu Ala Ser Leu Ala Thr Phe
    50                  55                  60

Leu Met Pro Leu Ile Ala Leu Leu Ala Tyr Asp Ala Ile Val Gly
65                  70                  75                  80

Glu Asp Glu Gly Gly Thr Leu Met Leu Leu Thr Tyr Pro Leu Gly
                85                  90                  95

Arg Gly Glu Ile Leu Leu Gly Lys Phe Val Gly His Gly Leu Ile Leu
            100                 105                 110

Ala Leu Ala Val Leu Ile Gly Phe Gly Gly Ala Leu Ala Ile Ala
        115                 120                 125

Leu Leu Val Glu Asp Ile Glu Leu Gly Leu Leu Leu Trp Ala Phe Gly
    130                 135                 140

Arg Phe Met Val Ser Ser Thr Leu Leu Gly Trp Val Phe Leu Ala Leu
145                 150                 155                 160
```

Ala Tyr Val Leu Ser Gly Lys Val Asn Glu Lys Ser Ala Ala Gly
        165                 170                 175

Leu Ala Leu Gly Ile Trp Phe Leu Phe Val Leu Val Phe Asp Leu Val
            180                 185                 190

Leu Leu Ala Leu Leu Val Leu Ser Glu Gly Lys Phe Ser Pro Glu Leu
        195                 200                 205

Leu Pro Trp Leu Leu Leu Leu Asn Pro Thr Asp Ile Tyr Arg Leu Ile
        210                 215                 220

Asn Leu Ser Gly Phe Glu Gly Gly Ala Met Gly Val Leu Ser Leu
225                 230                 235                 240

Gly Ser Asp Leu Pro Val Pro Asn Ala Val Leu Trp Leu Cys Leu Leu
                245                 250                 255

Ala Trp Ala Gly Ala Ser Leu Leu Leu Ala Tyr Gly Ile Phe Arg Arg
            260                 265                 270

Arg Leu Ala
        275

<210> SEQ ID NO 38
<211> LENGTH: 828
<212> TYPE: DNA
<213> ORGANISM: Pseudomonas stutzeri

<400> SEQUENCE: 38
atgaaccagg tctggaacat cgcccgcaag gaactcagcg atggcctgcg caaccgctgg      60
ctgctggcca tcagcctgtt gttcgcggtg ctggccgtgg ggatcgcctg gctcggtgcg     120
gccgcctcgg ggcaggtggg gttcacctcg atcccggcga ccatcgccag cctggccagc     180
ctggccacct tcctgatgcc gctgatcgcg ctgctgctgg cctatgacgc catcgtcggc     240
gaggacgaag gcggcacgct gatgctgctg ctgacctacc gctgggggcg cggcgagatc     300
ctgctcggca agttcgtcgg ccacgggctg atccttgccc tggcggtgtt gatcggcttc     360
ggcggcgccg ctctggccat cgccctgctg gtcgaggata tcgagctggg cctgctgctc     420
tgggccttcg gtcgcttcat ggtttcctcc acgctgctgg gctgggtgtt ccttgccctg     480
gcctacgtgc tcagcggcaa ggtcaacgag aaatccagcg ccgccggcct ggcgctgggg     540
atctggttcc tgttcgtgct ggtgttcgac ctggtgctgc tggcgctgct ggtgctcagc     600
gaaggcaagt tcagcccgga gttgctgccc tggctgctgc tgctcaaccc caccgacatc     660
taccggctga tcaacctgtc cggcttcgag ggcggcggcg ccatgggcgt gctgtcgctg     720
ggcagcgacc tgcccgtgcc gaacgccgtg ctctggctct gctgttggc ctgggcaggc     780 gcatcgctgc tgctggccta tggcatcttc cgtcggcgcc tggcctga                 828

<210> SEQ ID NO 39
<211> LENGTH: 828
<212> TYPE: DNA
<213> ORGANISM: Artificial
<220> FEATURE:
<223> OTHER INFORMATION: codon optimized Ps nosY gene

<400> SEQUENCE: 39
atgaaccaag tgtggaacat tgcgcgtaaa gagttgtctg atggtctccg taaccgctgg      60
ttacttgcta tttcattact ctttgccgta ttggctgtcg gcatcgcttg gctcggcgcc     120
gctgcgtctg gtcaagttgg tttcacgtct atcccagcga ctatcgcgtc cttagcgtca     180
ctggcaactt tcctgatgcc tttaattgca cttcttctcg cttatgatgc cattgtcggt     240
gaagatgagg gggggactct catgttatta ctgacctacc gttgggccg tggggaaatc     300

```
ttactgggca agttcgtggg gcatggctta atcttggctt tagctgtact catcgggttt    360
ggcggggcgg ctttagctat tgccctcttg gtcgaggaca ttgaacttgg gctgctgctc    420
tgggcattcg gccgcttcat ggtgagtagt acgctcctcg ggtgggtatt tttggccctc    480
gcttacgttc tttccggcaa agtcaatgag aagtcttctg cggcaggtct ggcgctgggg    540
atttggttct tgtttgtact tgtgttcgat cttgtccttt tagctctgct ggtattgtcc    600
gaagggaagt ttagtcctga attattgcct tggcttttgt tattgaatcc taccgacatc    660
tatcgtctta ttaatttgtc cggctttgaa ggtggtgggg cgatgggggt attgtcattg    720
gggagtgacc ttcctgtacc aaatgcggtc ttatggcttt gcctcctggc ttgggccggc    780
gcgtcattgc ttttggcgta tggcattttc cgtcgtcgct tagcttga              828
```

<210> SEQ ID NO 40
<211> LENGTH: 275
<212> TYPE: PRT
<213> ORGANISM: Pseudomonas aeruginosa

<400> SEQUENCE: 40

```
Met Pro Val Val Trp Thr Ile Ala Arg Lys Glu Leu Ala Asp Gly Leu
1               5                   10                  15

Arg Asn Arg Trp Leu Leu Ala Ile Ser Leu Leu Phe Ala Leu Leu Ser
                20                  25                  30

Val Gly Ile Ala Trp Phe Gly Ala Ala Ala Gly Gln Val Gly Phe
                35                  40                  45

Thr Ser Val Pro Ala Thr Val Ala Ser Leu Thr Ser Leu Ala Thr Phe
    50                  55                  60

Leu Met Pro Leu Ile Ala Leu Leu Ala Tyr Asp Ala Ile Val Gly
65                  70                  75                  80

Glu Glu Glu Gly Gly Thr Leu Leu Leu Leu Thr Tyr Pro Leu Gly
                    85                  90                  95

Arg Gly Gln Leu Leu Gly Lys Phe Leu Gly His Gly Leu Ile Leu
                100                 105                 110

Ala Leu Ala Thr Leu Ile Gly Phe Gly Ser Ala Ala Leu Ala Ile Leu
                115                 120                 125

Ala Leu Val Pro Glu Val Glu Ala Ala Ile Leu Leu Gly Ala Phe Gly
            130                 135                 140

Arg Phe Met Gly Ser Ser Leu Leu Leu Gly Cys Val Phe Leu Ala Leu
145                 150                 155                 160

Ala Tyr Ala Leu Ser Ser Arg Ala Ser Glu Lys Ser Ser Ala Ala Gly
                165                 170                 175

Gln Ala Leu Gly Leu Trp Phe Phe Val Leu Leu Phe Asp Leu Ala
            180                 185                 190

Leu Leu Ala Ile Leu Val Leu Ser Gln Gly His Leu Ser Pro Arg Leu
                195                 200                 205

Leu Pro Trp Leu Leu Leu Asn Pro Thr Asp Leu Tyr Arg Leu Ile
            210                 215                 220

Asn Leu Ser Gly Phe Asp Ala Ala Ala Gly Gly Val Val Pro Leu
225                 230                 235                 240

Ala Ser Asp Leu Pro Val Ser Ala Ser Ala Leu Trp Leu Ala Leu Ala
                245                 250                 255

Leu Trp Ala Cys Ala Ala Leu Ala Leu Ala His Gly Leu Phe Arg Arg
            260                 265                 270

Arg Pro Ile
```

275

<210> SEQ ID NO 41
<211> LENGTH: 828
<212> TYPE: DNA
<213> ORGANISM: Pseudomonas aeruginosa

<400> SEQUENCE: 41

| atgcccgtag tctggaccat cgcccgcaag gaactggccg acggcctgcg caatcgctgg | 60 |
| ctgctggcga tcagcctgct gttcgccctg ctctcggtgg gcatcgcctg gttcggcgcc | 120 |
| gccgcggccg gccaggtcgg cttcacttcg gtgccggcga cggtcgccag cctgaccagc | 180 |
| ctggccacct tcctgatgcc gctgatcgcc ctgctgctgg cctacgacgc catcgtcggc | 240 |
| gaggaggaag gcggcaccct gctgctgctc ctgacctacc cgctggggcg cggccagttg | 300 |
| ctgctcggca agttcctcgg tcacggcctg atcctcgccc tggccaccct gatcggcttc | 360 |
| ggcagcgcgg cgctggcgat cctcgcgctg gtgccgaggg tcgaggcggc catcctgctg | 420 |
| ggcgccttcg gccgcttcat gggttcctcg ctgctgctcg gctgcgtgtt cctcgccctg | 480 |
| gcctacgccc tgagcagccg cgccagcgag aaatccagcg ccgccgggca ggcgctcggc | 540 |
| ctgtggttct tcttcgtcct gctgttcgac ctggccctgc tggcgatcct ggtcctcagc | 600 |
| cagggtcacc tgagcccgcg gctgctgccc tggctgttgc tgctcaaccc gaccgacctc | 660 |
| taccggctga tcaacctgtc cggcttcgac gcagccgccg ccggcggggt ggttcccctg | 720 |
| gccagcgacc tgccggtgtc cgccagcgcc ctctggctgg ccctggccct ctgggcctgc | 780 |
| gctgccctgg cgctggccca cggcctgttc cgccgccgcc ccatctga | 828 |

<210> SEQ ID NO 42
<211> LENGTH: 828
<212> TYPE: DNA
<213> ORGANISM: Artificial
<220> FEATURE:
<223> OTHER INFORMATION: codon optimized Pa nosY gene

<400> SEQUENCE: 42

| atgccggtcg tgtggacgat tgcacgtaaa gagctcgccg acggccttcg taatcgctgg | 60 |
| ctccttgcaa tctcgctgtt gttcgctctc ttatccgtag ggattgcctg gttcggcgca | 120 |
| gccgcagctg gccaagttgg gttcacttcg gttcctgcga cagttgctag tctgacatcc | 180 |
| ctggccactt tcctcatgcc tttgatcgct ttgctcttgg cgtacgatgc tatcgtaggg | 240 |
| gaagaggaag gtggcacact cctgctcctg cttacttacc cattaggccg cggccagctc | 300 |
| ctcctcggga agtttctcgg tcatggcttg atcctcgcgc tggcaactct gattggtttc | 360 |
| ggttccgcag cacttgctat ccttgcactc gtgcctgaag tggaagccgc aattttactc | 420 |
| ggtgcattcg gtcgctttat ggggtcctca cttcttttag gttgcgtgtt cctggctttg | 480 |
| gcttatgcct tatcgagccg tgctagcgaa aagtcttctg ctgcagggca agccttaggg | 540 |
| ttgtggtttt tcttcgtgtt gcttttcgac ttagcattat tggctattct ggttctgagc | 600 |
| caaggtcact tatcaccacg tctccttcca tggttactct tgcttaaccc gacagacctg | 660 |
| taccgtctga ttaacttaag cggctttgat gcagccgccg ccggggggt cgtccctttg | 720 |
| gcttccgact tgccagtatc agccagtgcg ctttggctcg cgttggcgtt atgggcttgc | 780 |
| gcggcgttag cccttgctca tggcttgttc cgccgtcgcc caatttaa | 828 |

<210> SEQ ID NO 43
<211> LENGTH: 274

<212> TYPE: PRT
<213> ORGANISM: Pseudomonas versutus

<400> SEQUENCE: 43

Met Ile Arg Arg Ile Leu Ser Thr Ala Ala Leu Glu Phe Arg Ile Ala
1               5                   10                  15

Leu Arg Asn Arg Trp Val Ala Ile Ala Thr Ala Leu Met Val Val Phe
            20                  25                  30

Ala Leu Val Leu Ala Ala Gly Ala Ala Pro Thr Gly Asp Ile Gly
        35                  40                  45

Ala Asp Arg Leu Ser Val Val Val Ala Ser Leu Thr Ser Leu Ala Val
    50                  55                  60

Tyr Leu Val Pro Leu Leu Ala Leu Leu Met Ser Phe Asp Ala Val Ala
65                  70                  75                  80

Gly Glu Val Glu Arg Gly Thr Leu Pro Leu Leu Leu Thr Tyr Pro Val
                85                  90                  95

Ala Arg Ala Glu Val Leu Ala Gly Lys Leu Val Ala His Met Ala Ile
            100                 105                 110

Leu Ala Leu Ala Val Gly Ala Gly Tyr Gly Ala Ala Ala Leu Ala Ala
        115                 120                 125

Val Trp Ser Asp Pro Ala Ser Thr Ala Gly Leu Pro Ala Leu Trp Arg
    130                 135                 140

Leu Met Trp Ser Ser Thr Leu Leu Gly Ala Thr Phe Leu Gly Ala Gly
145                 150                 155                 160

Tyr Ala Leu Ser Ser Ile Ala Arg Arg Pro Ser Gly Ala Ala Gly Leu
                165                 170                 175

Ala Val Gly Leu Trp Leu Gly Leu Val Val Leu Tyr Asp Leu Ala Leu
            180                 185                 190

Leu Ala Leu Ile Val Ala Asp Gly Gly Gly Phe Thr Thr Glu Val
        195                 200                 205

Leu Pro Val Ala Leu Leu Ala Asn Pro Ala Asp Ala Phe Arg Leu Phe
    210                 215                 220

Asn Leu Ser Ala Ala Gln Ala Thr Ala Ala Ala Gly Val Gly Gly
225                 230                 235                 240

Ala Ala Ala Thr Ile Pro Leu Trp Gln Ser Ala Leu Ser Val Leu Ala
                245                 250                 255

Trp Pro Leu Ala Ala Leu Gly Leu Ala Ile Ala Ala Phe Arg Lys Val
            260                 265                 270

Thr Pro

<210> SEQ ID NO 44
<211> LENGTH: 825
<212> TYPE: DNA
<213> ORGANISM: Pseudomonas versutus

<400> SEQUENCE: 44
atgatccgcc gcatcctttc caccgcggcg ctggagttcc gcatcgcgct gcgcaaccgc      60
tgggtcgcca tcgccaccgc gctgatggtg gtctttgcgc tggtgctggc ggcggcgggt     120
gccgcgccca ccggcgacat cggcgccgac cggctgtcgg tcgtcgtcgc ctcgctgacc     180
tcgcttgccg tctacctggt gccgctgctg gcgctgctga tgagcttcga tgccgtcgcc     240
ggcgaggtcg agcgcggcac cttgcccttg ctgctgacct atcccgtggc gcgggccgag     300
gtgctggccg gcaagctggt cgcgcatatg gcgattctgg cgctggcggt gggcgcgggc     360
tacggcgcgg cggccctggc ggcggtctgg agcgatccgg cctcgaccgc ggggcttccg     420

```
gcgctgtggc ggctgatgtg gagctcgacc ctgctgggcg cgaccttcct gggcgccggc      480
tatgcgctgt ccagcatcgc gcgccggccc tcgggcgcgg ccgggctggc ggtcgggctg      540
tggctggggc tggtggtgct ttacgacctg gccctgctgg cgctgatcgt cgccgatggc      600
ggcggcggct tcaccaccga ggtgctgccg gtcgcgctgc ttgccaaccc ggccgacgcc      660
ttccgcctgt tcaacctctc ggccgcccag gccaccgccg ccgctgccgg cgtcggcggg      720
gccgccgcga ccatcccgct ttggcaatcg gcgctgtcgg tcctggcctg gccgctggcc      780
gcgcttggcc ttgccattgc cgcattccga aaggtcacgc catga                     825
```

<210> SEQ ID NO 45
<211> LENGTH: 825
<212> TYPE: DNA
<213> ORGANISM: Artificial
<220> FEATURE:
<223> OTHER INFORMATION: codon optimized Pv nosY gene

<400> SEQUENCE: 45

```
atgatccgtc gcattctcag tacagcggcc ttggaatttc gtattgctct ccgcaaccgt      60
tgggtggcca ttgcgactgc actcatggta gtgtttgctt tagttcttgc ggctgctggc     120
gcggcgccaa cgggtgatat tggcgcggac cgtttgagcg tagttgtggc ctcgctcact     180
tcactcgcag tgtatcttgt tcctctgtta gcacttctta tgtcgttcga cgctgtagct     240
ggcgaggtcg agcgcgggac gcttccgttg ttgcttacct atccggttgc acgcgcggag     300
gtactcgcgg ggaagctcgt tgcccacatg gcaattttag ctttagccgt gggtgctggt     360
tatggtgcag cagcgctcgc agcagtttgg tcggaccctg ccagcactgc agggcttcca     420
gcactttggc gtcttatgtg gagttccaca ttgctgggtg caacctttct gggcgcaggc     480
tacgcacttt cctcgattgc acgccgccct tctggcgcag ccgggttagc ggtggggctg     540
tggttgggcc tcgttgttct ttatgatctc gcattgttgg cactcatcgt agccgatggt     600
ggtggtggtt tcaccacgga agtgctccca gtggctttat agcgaaccc agccgatgcg     660 tttcgccttt taatttgtc cgctgcacaa gcaacagctg ccgctgcagg gttggtggc      720 gctgcagcca ctatcccact ttggcaaagc gccctcagcg ttctggcgtg ccattggct     780 gcattgggtc ttgcgattgc ggcgttccgt aaggttactc cgtaa                     825
```

<210> SEQ ID NO 46
<211> LENGTH: 192
<212> TYPE: PRT
<213> ORGANISM: Pseudomonas stutzeri

<400> SEQUENCE: 46

```
Met Met Asn Asn Leu Tyr Arg Thr Gly Ala Gln Ala Leu Leu Ala Met
1               5                   10                  15

Leu Leu Ala Phe Gly Leu Ala Ala Cys Gly Asp Lys Gln Glu Val Gln
                20                  25                  30

Gln Ser Leu Asp Pro Val Ala Phe His Glu Ser Asp Cys His Val
        35                  40                  45

Cys Gly Met Ile Ile Ala Asp Phe Pro Gly Pro Lys Gly Gln Ala Val
    50                  55                  60

Asp Lys Ala Gly Val Lys Lys Phe Cys Ser Thr Ala Glu Met Leu Gly
65                  70                  75                  80

Trp Tyr Leu Gln Pro Glu Asn Lys Leu Leu Asp Ala Lys Leu Tyr Val
                85                  90                  95
```

```
His Asp Met Gly Lys Ser Glu Trp Ala His Pro Ser Asp Glu His Leu
                100                 105                 110
Ile Asp Ala Arg Thr Ala Trp Tyr Val Ala Gly Thr Pro Leu Lys Gly
            115                 120                 125
Ala Met Gly Val Ser Leu Ala Ser Phe Ala Asp Glu Gln Gln Ala Gln
130                 135                 140
Gln Leu Ala Ala Glu His Gly Gly Arg Val Leu Arg Phe Glu Glu Ile
145                 150                 155                 160
Asp His Gly Val Leu Gln Gln Gly Ala Asp Met Gln His His Asp Met
                165                 170                 175
His Glu Gln His Met Ser Glu Thr Glu His Asn Asp His Ala Gly His
            180                 185                 190

<210> SEQ ID NO 47
<211> LENGTH: 579
<212> TYPE: DNA
<213> ORGANISM: Pseudomonas stutzeri

<400> SEQUENCE: 47
atgatgaaca atctgtaccg taccggcgcc caggcgctgc tcgcgatgct cctggcattc      60
gggttggccg cctgtggcga caagcaagaa gtccagcaat cgctcgatcc ggtggctttc     120
catgaaagcg acgaatgcca cgtctgcggc atgatcatcg ccgacttccc cggcccgaaa     180
ggccaggcgg tggataaggc cggcgtgaag aaattctgct ccaccgccga gatgctcggc     240
tggtacctgc agccggaaaa caagctgctc gatgccaagc tctatgtgca tgacatgggc     300
aagagcgaat gggcgcaccc cagcgacgag cacctgatcg acgcccgcac ggcctggtac     360
gtcgccggta cgccgctcaa gggcgccatg gtgtgtctcc tggccagttt cgccgatgag     420
cagcaggcgc agcagctcgc tgccgagcat ggcggacggg tgctgcgttt cgaagagatc     480
gaccatgggg tgctgcagca gggcgcggac atgcagcacc acgacatgca tgagcagcac     540
atgtccgaaa ccgaacacaa cgatcacgcg ggtcattga                            579

<210> SEQ ID NO 48
<211> LENGTH: 579
<212> TYPE: DNA
<213> ORGANISM: Artificial
<220> FEATURE:
<223> OTHER INFORMATION: codon optimized Ps nosL gene

<400> SEQUENCE: 48
atgatgaata atttgtaccg caccggtgct caggcgttgc ttgctatgct tttggctttt      60
ggtctcgcgg cgtgtggcga caagcaagaa gtccagcaat ccttggatcc agtagcgttc     120
catgagtccg atgaatgtca cgtgtgcggc atgattattg ccgacttccc tggtccaaaa     180
ggccaggcag ttgataaggc cggtgtcaag aagttttgca gcacagcaga gatgcttggg     240
tggtatctcc agccagaaaa taaattgctc gatgcgaaac tttacgtaca tgatatgggt     300
aagtcagaat gggcacatcc gagcgatgag cacctgatcg acgcacgcac tgcctggtat     360
gttgctggta caccattaaa gggtgcaatg ggcgtctcct tagcctcttt cgccgacgaa     420
caacaggcgc agcaactggc agcagaacac ggcgggcgtg tactgcgctt cgaggagatt     480
gaccacggtg tgctccagca gggggccgat atgcagcacc acgatatgca cgaacaacac     540
atgagcgaaa cagaacataa tgaccatgca ggccattga                            579

<210> SEQ ID NO 49
<211> LENGTH: 178
```

```
<212> TYPE: PRT
<213> ORGANISM: Pseudomonas aeruginosa

<400> SEQUENCE: 49

Met Gln Arg His Thr Leu Pro Leu Arg Pro Leu Leu Gly Thr Leu Leu
1               5                   10                  15

Leu Gly Leu Leu Leu Ala Gly Cys Asp Ala Ser Arg Asp Asp Ala Thr
            20                  25                  30

Ala Leu Gly Pro Val Pro Ile Ala Ser Gly Asp Glu Cys His Val Cys
        35                  40                  45

Gly Met Leu Ile Glu Glu Met Pro Gly Pro Lys Gly Glu Ala Val Leu
    50                  55                  60

Pro Gly Ala Val Arg Lys Phe Cys Ser Thr Ala Glu Leu Phe Gly Trp
65                  70                  75                  80

Trp Leu Gln Pro Glu Asn Arg Gln Gly Gln Ala Arg Leu Tyr Val His
                85                  90                  95

Asp Met Ser Gln Ala Asp Trp Arg His Pro Asp Asp Ala Arg Leu Ile
            100                 105                 110

Asp Ala Thr Arg Ala Tyr Tyr Val Val Gly Ile Gln Arg Pro Gly Gly
        115                 120                 125

Met Gly Ala Thr Leu Ala Ser Phe Ala Asp Glu Glu Ala Ala Thr Arg
    130                 135                 140

Leu Ala Ala Glu Glu Gly Gly Arg Val Leu Arg Phe Asp Glu Ile Asp
145                 150                 155                 160

Gln Ala Val Leu Gln Gly Val Gly Gly Asp His Pro His Arg His Pro
                165                 170                 175

Ala His

<210> SEQ ID NO 50
<211> LENGTH: 537
<212> TYPE: DNA
<213> ORGANISM: Pseudomonas aeruginosa

<400> SEQUENCE: 50
atgcaacgtc ataccctccc cctgcgccct ctgctcggca cgctcctgct cggcctgctg      60
ctggccggct gcgatgcgtc gcgggacgac gccacggcac tcggcccggt gccgatcgcc     120
agcggcgacg aatgccacgt ctgcggcatg ctcatcgagg aaatgcccgg tcccaagggc     180
gaggcggtgc ttcccggcgc ggtgcgcaag ttctgctcca ccgccgaact gttcggctgg     240
tggctgcaac ggaaaaccg ccagggccag gcgcgcctgt atgtccacga catgagccag     300
gccgactggc ggcaccccga cgatgcccgc ctgatcgacg ccacccgcgc ctactacgtg     360
gtcggcatcc agcggccggg cggcatgggc gccaccctcg cctcgttcgc cgacgaagag     420
gccgcgacgc gcctggcggc cgaggaaggc ggccgggtac tgcgcttcga cgagatcgac     480
caggcggtgc tgcaaggcgt gggcggcgac caccccgcac cggcacccgg cactga        537

<210> SEQ ID NO 51
<211> LENGTH: 537
<212> TYPE: DNA
<213> ORGANISM: Artificial
<220> FEATURE:
<223> OTHER INFORMATION: codon optimized Pa nosL gene

<400> SEQUENCE: 51
atgcaacgtc acaccctccc gctgcgccct ttgttgggga ccctttattt gggtcttctg      60
cttgcgggtt gtgacgcttc acgcgacgat gcgactgcgt tgggtccggt gccgatcgct     120
```

```
tcgggtgatg agtgccatgt gtgcggcatg cttatcgagg agatgccggg tcctaaaggc      180
gaggcggttt tgcctggtgc tgtccgcaag ttttgctcca ccgcagaact ctttggttgg      240
tggttacaac cggagaatcg ccaaggtcag gcacgtctgt atgtgcatga catgagccaa      300
gccgattggc gccatcctga cgacgctcgt ttaattgatg ctacacgcgc gtattacgtt      360
gtcggtattc aacgccctgg gggtatgggt gccactttgg cttcctttgc tgacgaggag      420
gccgccactc gcttagcagc cgaagagggg ggccgtgtgc tccgctttga tgaaattgat      480
caagcagtct tacaagggt aggtggcgac cacccacacc gccacccggc tcattaa        537
```

<210> SEQ ID NO 52
<211> LENGTH: 191
<212> TYPE: PRT
<213> ORGANISM: Pseudomonas aeruginosa

<400> SEQUENCE: 52

```
Met Arg His Ala Leu Leu Val Leu Leu Gly Leu Ala Ala Cys
1               5                   10                  15

Arg Glu Glu Val Ala Gln Asp Thr Thr Pro Val Glu Met Asn Ala Gln
                20                  25                  30

Thr Leu Gly His Phe Cys Gln Met Asn Leu Leu Glu His Pro Gly Pro
            35                  40                  45

Lys Ala Gln Val His Leu Glu Gly Met Pro Gly Thr Pro Leu Phe Phe
        50                  55                  60

Ser Gln Val Arg Asp Ala Ile Ala Tyr Ala Arg Met Pro Glu Gln Ser
65                  70                  75                  80

His Pro Ile Leu Ala Ile Gln Val Asn Asp Met Gly Ala Pro Gly Ala
                85                  90                  95

Thr Trp Glu Glu Pro Gly Gln Gly Asn Trp Ile Glu Ala Lys Asp Ala
            100                 105                 110

Phe Phe Val Met Gly Ser Val Gln Val Gly Gly Met Gly Ala Pro Glu
        115                 120                 125

Ala Val Pro Phe Ser Ser Arg Glu Ala Ala Asp Ala Phe Val Ala Ala
    130                 135                 140

Gln Gly Gly Gln Val Met Arg Leu Asp Ala Ile Pro Asp Glu Met Val
145                 150                 155                 160

Leu Ala Pro Glu Glu Thr Val Pro Asp Ala Ser Thr Glu Ala Asp Phe
                165                 170                 175

Ile Asn Arg Leu Arg Ala Leu Ser Gln Pro Lys Glu Pro Ala Thr
            180                 185                 190
```

<210> SEQ ID NO 53
<211> LENGTH: 576
<212> TYPE: DNA
<213> ORGANISM: Pseudomonas aeruginosa

<400> SEQUENCE: 53

```
atgagacatg cgctgctgct ggtgctgctg ctgggccttg ccgcctgccg cgaggaggtc       60
gcacaggaca ccacgccggt cgagatgaac gcccagacgc tgggccattt ctgccagatg      120
aacctgctgg agcatccgg ccccaaggcg caggtgcatc tggagggat gccgggcacg      180 ccgctgttct tcagccaggt ccgcgacgcc atcgcctatg ccaggatgcc gagcaaagc      240 cacccgatcc tggccatcca ggtgaacgac atgggtgcgc ccggcgcgac ctgggaagag      300
ccggggcagg gcaactggat cgaggcgaag gacgccttct cgtcatggg ctcggtccag      360
```

```
gtcggcggca tgggcgcgcc cgaggcggtg ccctttttcca gccgcgaggc cgccgatgcc    420
ttcgtcgccg cgcagggcgg gcaggtgatg cggctggacg cgatccccga cgagatggtg    480
ctggcgcccg aggagaccgt gcccgacgcc agcacggaag ccgatttcat caaccgcctg    540
cgcgcgctga gccaacccaa ggagcccgcg acatga                              576

<210> SEQ ID NO 54
<211> LENGTH: 576
<212> TYPE: DNA
<213> ORGANISM: Artificial
<220> FEATURE:
<223> OTHER INFORMATION: codon optimized Pv nosL gene

<400> SEQUENCE: 54
atgcgccacg ctctcttgct tgtgttgttg cttggcttag ctgcctgccg tgaagaggtc     60
gcccaagata caaccccctgt tgaaatgaac gcacagaccc ttgggcattt ctgccaaatg   120
aacttgcttg agcatcctgg cccgaaggcg caggttcacc ttgagggcat gcctgggaca   180
cctttatttt tttcccaagt gcgtgacgct atcgcctacg ctcgcatgcc tgagcagagc   240
cacccaatcc tcgcaattca ggtgaatgac atgggggcac ctggcgcgac atggggaggag  300 cctggtcagg ggaattggat cgaagctaag gatgcttttt tcgtgatggg ttccgtccag   360
gtcgggggca tgggggcgcc tgaggcagta ccgttttcct cacgcgaagc ggcggatgcc   420
ttcgtggcgg cacagggcgg tcaagtaatg cgtttgatg ccatccccga tgaaatggtg    480
ttggctccag aagagaccgt gccagatgct tcgactgaag cggacttcat caaccgcctt   540
cgcgctcttt cacagcctaa agaaccggcg acctaa                             576

<210> SEQ ID NO 55
<211> LENGTH: 341
<212> TYPE: PRT
<213> ORGANISM: Pseudomonas stutzeri

<400> SEQUENCE: 55

Met Gly Arg Ala Ser Leu Gln Pro Val Ile Ala Val Ala Leu Ala Ala
 1               5                  10                  15

Ala Leu Thr Gly Cys Leu Phe Gln Asp Lys Val Glu Asp Phe Gly Gly
            20                  25                  30

Pro Thr Met Gly Ser Thr Tyr Ser Val Lys Tyr Val Ala Ser Asp Gly
        35                  40                  45

Ala Ala Ala Lys Ala Gln Leu Gln Arg Glu Thr Glu Ser Ile Leu Ala
    50                  55                  60

Gln Leu Asp Glu Gln Leu Ser Thr Tyr Arg Ala Asp Ser Asp Ile Glu
65                  70                  75                  80

Ala Phe Asn Ala Leu Pro Ala Gly Gln Cys Met Ala Met Pro Glu Ser
                85                  90                  95

Ala Arg Glu Leu Val Leu Ala Gly Gln Gln Leu Ser Gln Glu Ser Asp
            100                 105                 110

Gly Ala Leu Asp Leu Thr Ile Gln Pro Leu Leu Asn Leu Trp Gly Phe
        115                 120                 125

Gly Pro Gln Gly Arg Arg Glu Gln Val Pro Ser Ala Glu Ile Ala
    130                 135                 140

Arg Ala Arg Glu Thr Val Gly His Arg His Leu Gln Val Val Gly Glu
145                 150                 155                 160

Gln Leu Cys Lys Asp Ala Ala Val Glu Val Asp Phe Asn Ser Ile Ala
                165                 170                 175
```

Ala Gly Tyr Ala Val Asp Leu Val Ala Gln Arg Leu Glu Ala Leu Gly
            180                 185                 190

Val Glu Ser Tyr Leu Val Glu Ile Thr Gly Glu Leu Lys Ala Arg Gly
        195                 200                 205

Arg Lys Pro Gly Asp Ala Pro Trp Arg Ile Ala Ile Glu Ala Pro Arg
    210                 215                 220

Asp Asn Glu Arg Val Ala Gln Arg Val Ile Glu Leu Asp Gly Tyr Gly
225                 230                 235                 240

Val Ser Thr Ser Gly Asp Tyr Arg Asn Tyr Phe Glu Arg Asp Gly Lys
                245                 250                 255

Arg Tyr Ser His Thr Leu Asp Pro Gln Thr Gly Ala Pro Ile Glu His
            260                 265                 270

Arg Leu Ala Ala Val Thr Val Val Asp Pro Ser Ala Leu Arg Ala Asp
        275                 280                 285

Gly Leu Ser Thr Val Leu Met Val Leu Gly Pro Glu Arg Gly Leu Ala
    290                 295                 300

Tyr Ala Ala Glu His Arg Ile Ala Ala Leu Phe Val Ile His Glu Glu
305                 310                 315                 320

Gln Glu Phe Ile Ser Lys Ser Thr Ala Ala Phe Asp Glu Leu Phe Gly
                325                 330                 335

Ala Gly Ala Glu Gln
            340

<210> SEQ ID NO 56
<211> LENGTH: 1026
<212> TYPE: DNA
<213> ORGANISM: Pseudomonas stutzeri

<400> SEQUENCE: 56

```
atgggccgag cgtcactcca acccgtcatc gctgtcgccc tggcggcagc cctgacgggt     60
tgtctgtttc aggacaaggt agaagacttc ggtggcccga ccatgggcag tacctactcg    120
gtgaagtacg ttgccagtga tggtgcggct gccaaggcac aactgcagcg cgagaccgaa    180
tcgattctgg cccagctgga cgagcagttg tcgacctacc gcgccgattc ggatatcgaa    240
gccttcaatg ccctcccggc agggcagtgc atggccatgc ccgagtccgc ccgcgagctc    300
gtgctggctg gcagcagct gtcgcaggaa agcgacggcg cactggacct gaccattcag    360
ccgctgctca acctctgggg gttcggcccg caggggcgcc gtgagcaggt accttctgcc    420
gaggaaattg ccagggcccg cgagactgtc ggtcaccggc atctgcaggt tgtcggcgag    480
cagctgtgca aggatgcggc cgtcgaggtc gatttcaaca gcatcgctgc gggttacgct    540
gtcgatctgg tggcgcaaag gctggaagcg ctcggggtcg aaagctatct ggtggaaatc    600
actggcgagc tcaaggcacg aggccgaaag ccgggtgacg cgccgtggcg gatcgccatc    660
gaagcgccgc gggataatga gcgtgtggcg cagcgcgtca tcgagctcga tggctatggc    720
gtttccacct cgggtgacta ccgcaattat ttcgagcgtg atggcaagcg ctactcgcat    780
acgctggatc cgcaaaccgg tgccccgatc gagcatcgcc tggcggccgt gacggtcgtc    840
gatccatcag cactgcgcgc ggacgggttg tctaccgtcc tgatggtgct ggggccggaa    900
cgtggcctgg cgtatgccgc ggagcacagg atccagcgc tcttcgtgat tcatgaagag    960
caggaattca tcagcaaaag caccgcagcc ttcgatgagc tgttcggtgc gggagcagag   1020
caatga                                                              1026
```

<210> SEQ ID NO 57

<211> LENGTH: 1026
<212> TYPE: DNA
<213> ORGANISM: Artificial
<220> FEATURE:
<223> OTHER INFORMATION: codon optimized Ps apbE gene

<400> SEQUENCE: 57

| | | |
|---|---|---|
| atggggcgtg cgagcctgca accagtaatt gctgttgctt tagcggcggc gctgaccggt | 60 |
| tgccttttcc aggataaggt cgaagatttt ggggggccga ccatgggtag tacttactct | 120 |
| gtcaaatacg tcgccagcga tggcgcggct gcgaaagctc aactccaacg cgaaactgag | 180 |
| agtatcttgg cacagttgga tgagcaactc tccacttatc gtgctgacag cgatattgaa | 240 |
| gcctttaacg ccctgccagc tggtcaatgc atggcgatgc agaaagcgc tcgcgaactg | 300 |
| gtattagcag tcagcaact tagtcaagag tccgacggtg cgctggatct cacaatccaa | 360 |
| ccattactga atttatgggg tttcggccct cagggccgcc gtgaacaagt cccatcggca | 420 |
| gaggaaatcg ctcgtgcccg tgagaccgtg ggtcatcgtc atctccaggt tgtgggcgaa | 480 |
| caactgtgca aggacgcagc tgtcgaggtg gattttaact caattgcggc aggctatgct | 540 |
| gtggacctcg ttgcacagcg tcttgaagcg ctcggtgttg agtcttatct ggtggaaatc | 600 |
| actggggaac tgaaggcccg tggtcgcaaa ccaggcgatg cgccgtggcg tatcgcgatc | 660 |
| gaagctccgc gtgataacga gcgtgtggcg cagcgtgtaa ttgaattgga tggttacggc | 720 |
| gtcagcaccct caggtgacta tcgcaactat tttgaacgtg acgggaagcg ttactctcac | 780 |
| actctcgatc ctcagaccgg cgcacctatc gaacaccgcc tggctgcggt aacggtggta | 840 |
| gatccatcag ctcttcgcgc agatggggttg tccactgtgc ttatggtgct cggcccagaa | 900 |
| cgtgggttgg cgtatgcggc tgagcaccgt atcgcggcac tctttgtgat ccatgaggaa | 960 |
| caggaattta tcagcaaatc cactgccgct tttgacgagc tcttcggggc gggggcagag | 1020 |
| cagtga | 1026 |

<210> SEQ ID NO 58
<211> LENGTH: 333
<212> TYPE: PRT
<213> ORGANISM: Pseudomonas aeruginosa

<400> SEQUENCE: 58

Met Ala Gly Leu Ala Ala Leu Ala Leu Val Leu Ala Gly Cys Gly Asp
1               5                   10                  15

Thr Leu Glu Ser Phe Gly Gly Pro Thr Met Gly Ser Thr Tyr Ser Ile
            20                  25                  30

Lys Tyr Val Arg Gly Ala Ser Ala Pro Asp Val Gln Thr Ala Lys Ala
        35                  40                  45

Ala Val Glu Ala Ile Leu Ala Glu Val Asp Arg Gln Met Ser Thr Tyr
    50                  55                  60

Arg Asp Asp Ser Leu Val Ser Arg Phe Asn Ala Leu Pro Ala Gln Ser
65                  70                  75                  80

Cys Met Glu Leu Pro Pro Met Leu Glu Leu Leu Arg Tyr Gly Gly
                85                  90                  95

Glu Leu Ser Glu Gln Ser Gln Gly Ala Phe Asp Met Thr Val Glu Pro
            100                 105                 110

Leu Met Asn Leu Trp Gly Phe Gly Pro Gln Ala Arg Val Glu Lys Val
        115                 120                 125

Pro Ser Ala Glu Gln Ile Ala Val Arg Arg Asp Val Gly His Arg
    130                 135                 140

His Leu Arg Ile Asp Gly Gln Arg Leu Cys Lys Asp Ala Ala Val Gln
145                 150                 155                 160

Leu Asp Phe Asp Ser Ile Ala Ala Gly Tyr Thr Val Asp Ala Val Gly
            165                 170                 175

Glu Arg Leu Lys Glu Leu Gly Val Arg Ser Tyr Leu Ala Glu Ile Thr
        180                 185                 190

Gly Glu Leu Lys Ala Glu Gly Arg Lys Pro Asp Gly Thr Pro Trp Arg
        195                 200                 205

Ile Ala Ile Glu Ala Pro Arg Glu Gly Gln Arg Val Ala Gln Gln Val
210                 215                 220

Leu Ala Leu Asp Gly Tyr Gly Val Ser Thr Ser Gly Asp Tyr Arg Asn
225                 230                 235                 240

Tyr Phe Glu Glu Asn Gly Gln Arg Tyr Ser His Thr Phe Asp Pro Arg
                245                 250                 255

Thr Gly Ala Pro Ile Asp His His Leu Ala Ser Val Thr Val Ile Asp
            260                 265                 270

Pro Ser Thr Arg Asn Ala Asp Gly Leu Ser Thr Leu Leu Met Ala Leu
        275                 280                 285

Gly Pro Glu Glu Gly Tyr Arg Phe Ala Glu Lys His Arg Leu Ala Ala
290                 295                 300

Leu Phe Val Ser Arg Gln Gly Asn Gly Phe Asp Ser Arg Thr Thr Pro
305                 310                 315                 320

Arg Tyr Glu Gln Leu Phe Gly Asn Gln Gly Glu Arg Pro
                325                 330

<210> SEQ ID NO 59
<211> LENGTH: 1002
<212> TYPE: DNA
<213> ORGANISM: Pseudomonas aeruginosa

<400> SEQUENCE: 59

```
atggccggac tggcagcgct ggcgctggtc ctggccggtt gcggcgacac cctggaaagc      60
ttcggcggcc cgaccatggg cagcacctat tcgatcaagt acgtacgcgg cgcctcggcg     120
cccgacgtcc agacggcgaa agccgcggtg gaggcgatcc tcgccgaggt cgaccggcag     180
atgtccacct accgcgacga ttccctggtc tcgcgtttca atgcgctgcc ggcgcagtcc     240
tgcatggagc tgccgccacc gatgctggag ttgctgcgct acggcggcga gttgtcggag     300
cagagccagg gcgccttcga catgaccgtc gagccgctga tgaacctctg gggcttcggt     360
ccgcaggcgc gggtagagaa ggttcccagc gccgagcaga tcgccgcggt gcgccgtgac     420
gtcggccatc gacacctgcg catcgacggc cagcgcctgt gcaaggacgc cgccgtacaa     480
ttggacttcg acagcatcgc cgctggctat acggtggacg cggtaggcga acgcctgaag     540
gagctcggcg tgcgcagcta cctggcggaa atcaccggcg agttgaaagc cgaagggcgc     600
aagccggacg gcacgccctg gcgcatcgct atcgaagcgc cgcgcgaggg ccagcgggtc     660
gcccagcagg tactggcgct ggacggctac ggcgtctcga cctcgggcga ttaccgcaac     720
tatttcgaag agaacggcca gcgctattcg cacaccttcg acccgcgcac cggcgcgccg     780
atcgaccatc acctggcttc ggtcacggtg atcgatccgt cgacgcgcaa cgccgacggc     840
ctgtcgaccc tgctgatggc gctcggtccg gaggagggct accgtttcgc cgagaagcac     900
cgactggcgg cgctgttcgt cagtcgccag ggcaacggtt tcgacagccg caccacgcca     960
cgctacgagc aactgttcgg caaccaagga gaacgtccat ga                       1002
```

<210> SEQ ID NO 60
<211> LENGTH: 1002
<212> TYPE: DNA
<213> ORGANISM: Artificial
<220> FEATURE:
<223> OTHER INFORMATION: codon optimized Pa apbE1 gene

<400> SEQUENCE: 60

```
atggcggggt tagcagcgct ggcacttgtt ctggccgggt gtggtgacac tttggaaagt      60
ttcggcggtc ctactatggg gtccacttat tccattaagt acgttcgcgg cgcttcggct     120
cctgacgtac agaccgccaa ggccgcagtt gaggccattt tggcggaagt ggaccgccag     180
atgagtacat accgtgacga cagcctggtt tctcgtttta atgcattgcc agcgcaatcg     240
tgtatggaat tgccgccacc tatgctcgaa ttgttacgct acggtggtga gctttcagaa     300
caaagtcagg gcgcttttga tatgactgtc gagcctctga tgaacctgtg ggggttcggc     360
ccgcaagccc gcgtggaaaa ggttccttcg gcagaacaga tcgccgcggt gcgccgcgat     420
gtggggcatc gtcatctccg tatcgacggt cagcgcttgt gtaaagatgc ggccgtacaa     480
ctcgactttg attcaattgc agccggctac acagtagatg cagtgggcga cgtttaaag     540
gagcttggtg tccgttcata tttggccgaa attactggcg aattgaaagc agaggggcgc     600
aagcctgatg ggacgccatg gcgtatcgct attgaggcgc acgcgaggg ccagcgtgtg     660
gcccagcagg tgcttgcgct cgatggctac ggtgtgtcta cgtctgggga ttaccgcaac     720
tattttgagg aaaacggtca acgctatagt cacacgtttg accctcgtac aggtgcgccg     780
atcgatcacc acttagcgtc agtcacagtg atcgacccga gcactcgcaa cgcagatggc     840
ttatccactc tcctgatggc gctcggtcct gaagagggtt accgttttgc agagaaacac     900
cgtcttgcgg cgcttttgt gagccgccaa gggaatggtt tcgactcacg gacaactccg     960
cgctatgaac aactgttcgg gaatcagggt gaacgcccat aa                      1002
```

<210> SEQ ID NO 61
<211> LENGTH: 302
<212> TYPE: PRT
<213> ORGANISM: Pseudomonas versutus

<400> SEQUENCE: 61

```
Met Ser Arg Arg Arg Phe Leu Thr Ile Thr Ala Ala Val Ala Leu Ala
1               5                   10                  15

Pro Ala Ala Leu Arg Ala Gln Pro Gly Arg His Trp Val Gly Gln Ala
            20                  25                  30

Leu Gly Ala Arg Ala Ser Ile Arg Ile Asp His Pro Glu Ala Glu Ala
        35                  40                  45

Ile Thr Ala Arg Cys Leu Ala Glu Ile Asp Arg Leu Glu Gly Ile Leu
    50                  55                  60

Ser Leu Tyr Arg Pro Asp Ser Ala Leu Ser Arg Leu Asn Arg Asp Ala
65                  70                  75                  80

Ala Leu Glu Ala Pro Pro Phe Glu Leu Leu Glu Cys Leu Ser Leu Ala
                85                  90                  95

Gly Thr Val His Arg Ala Ser Gly Gly Leu Phe Asp Pro Thr Val Gln
            100                 105                 110

Pro Leu Trp Ser Leu Trp Ala Glu Ala Ala Leu Ala Gly Arg Arg Pro
        115                 120                 125

Thr Ala Asp Glu Arg Arg Ala Ala Leu Ala Arg Thr Gly Trp Glu Arg
    130                 135                 140

Val Arg Leu Asp Ala Ala Arg Ile Thr Leu Glu Pro Gly Met Ala Leu
```

```
            145                 150                 155                 160
Thr Leu Asn Gly Ile Gly Gln Gly Tyr Val Ala Asp Arg Val Ala Ala
                165                 170                 175

Leu Leu Glu Ala Glu Gly Leu Gly Asp Ile Leu Ile Asp Thr Gly Glu
            180                 185                 190

Leu Arg Ala Leu Gly Ser Arg Pro Asp Gly Thr Asp Trp Pro Val Arg
            195                 200                 205

Leu Ala Glu Gly Gly Ala Val Gly Leu Arg Gly Arg Ala Leu Ala Thr
210                 215                 220

Ser Ala Pro Leu Gly Thr Ser Phe Asp Gln Ala Gly Arg Asp Gly His
225                 230                 235                 240

Ile Leu Asp Pro Arg Ser Gly Ala Pro Ala Arg Pro Ala Trp Arg Ala
                245                 250                 255

Ile Ser Ile Ser Ala Pro Gly Ala Gly Leu Ala Asp Ala Leu Ser Thr
                260                 265                 270

Ala Ala Cys Leu Ala Gly Asp Arg Gln Glu Ile Leu Ala Leu Leu Ala
            275                 280                 285

Arg Phe Asp Gly Ala Arg Leu Glu Ala Ala Pro Arg Gly Ala
            290                 295                 300
```

<210> SEQ ID NO 62
<211> LENGTH: 909
<212> TYPE: DNA
<213> ORGANISM: Pseudomonas versutus

<400> SEQUENCE: 62

```
ctgtcccgcc gtcgctttct gaccatcacc gccgccgtgg cgcttgcgcc cgcggccctg      60
cgtgcccagc ccggccggca ttgggtcggg caggcgcttg cgcccgcgc ctcgatccgc      120
atcgaccacc ccgaggccga ggcgatcacc gcccgctgcc tggccgagat cgaccggctg      180
gaaggcatcc tcagcctcta tcgtcccgac agcgccctgt cgcggctgaa ccggacgcg      240
gcgctggagg cgccgccctt cgagctgctg gaatgcctgt cgctgccgg cacggtgcat      300
cgcgccagcg gcgggctgtt cgaccctacc gtgcagccgc tctggtcgct ctgggccgag      360
gccgccttgg ccggccgccg ccccaccgcg gacgagcgtc gcgcggcgct ggcgcgcacc      420
ggctgggagc gggtgcggct ggacgcggcc gcatcacgc tggagccggg gatggcgctg      480
acgctgaacg gcatcggcca gggctatgtc gccgaccgcg tcgccgcgct ctcgaggcc      540
gaggggctgg cgacatcct gatcgacacc ggcgaattgc gcgccctggg cagccggccc      600
gacggcaccg actggccggt gcggctggcc gagggcggcg cggtgggcct gcgcggccgg      660
gcgctggcga catcggcgcc gctgggcacc agcttcgacc aggcggggcg cgacggccat      720
atcctcgacc cgcgcagcgg cgcgccggcg cgtccggcct ggcgcgcgat cagcatctcg      780
gcccccggcg cgggcttggc cgatgcgctg tccaccgccg cctgcctggc cggcgaccgg      840
caggagatcc tggcgctgct ggcccgtttc gacggcgccc ggcttgaagc ggcgccgcgc      900
ggggcatag                                                              909
```

<210> SEQ ID NO 63
<211> LENGTH: 909
<212> TYPE: DNA
<213> ORGANISM: Artificial
<220> FEATURE:
<223> OTHER INFORMATION: codon optimized Pv apbE1 gene

<400> SEQUENCE: 63

```
atgtcacgcc gtcgtttcct gactattact gcagctgtgg cgctggctcc tgctgcgctg      60
cgcgcgcaac caggccgcca ttgggtaggc caagcattag gtgctcgtgc atccattcgc     120
attgaccatc cagaggctga ggctattaca gcacgctgct tggctgagat tgatcgcctg     180
gagggtatcc tttcccttta tcgtccggac agcgcgctta gtcgcttgaa ccgcgatgcc     240
gcgctggaag cgccaccatt cgaactcctg gaatgcttaa gtctcgctgg cacggtccat     300
cgtgcgtctg gtggtctctt tgacccaact gtgcagcctc tttggtcatt atgggccgaa     360
gccgcgcttg ccggtcgccg tccaactgcg gatgaacgtc gtgcagcttt agcacgtaca     420
ggttgggagc gcgtacgctt ggacgcagct cgtatcacct tagagccagg catggctctc     480
accctcaatg gtattgggca aggttatgtc gccgaccgcg ttgctgccct gctcgaagca     540
gagggccttg gtgacatcct gattgacacc ggggaactcc gcgctctcgg gagtcgcccg     600
gacgggaccg attggccagt acgcctcgcc gaaggtgggg ccgtggggct tcgtgggcgt     660
gcattagcta cctccgcgcc gctgggtacc tccttcgacc aggctgggcg cgacggccat     720
atcttggacc cacgttcggg cgcgccagct cgcccggctt ggcgtgcgat ctcaatttcg     780 gccccctggcg caggtcttgc agacgcctta agcaccgccg catgtttggc tggtgaccgt     840
caggaaattt tagcgttact tgcacgcttc gacggggccc gccttgaggc ggctcctcgc     900
ggtgcctga                                                              909
```

<210> SEQ ID NO 64
<211> LENGTH: 76
<212> TYPE: PRT
<213> ORGANISM: Pseudomonas stutzeri

<400> SEQUENCE: 64

Met Gly Leu Gly Gly Ile Ser Val Trp Gln Leu Leu Ile Ile Leu Leu
1               5                   10                  15

Ile Val Ile Met Leu Phe Gly Thr Lys Arg Leu Lys Gly Leu Gly Ser
            20                  25                  30

Asp Leu Gly Asp Ala Ile Lys Gly Phe Arg Lys Ser Met Gly Thr Asp
        35                  40                  45

Glu Glu Lys Pro Gly Val Glu Glu Lys Gln Ser His Thr Ile Asp Ala
    50                  55                  60

Glu Ala Arg Lys Val Glu Asp Pro Thr Lys Lys Asn
65                  70                  75

<210> SEQ ID NO 65
<211> LENGTH: 231
<212> TYPE: DNA
<213> ORGANISM: Pseudomonas stutzeri

<400> SEQUENCE: 65

```
atgggtttgg gtggaattag cgtctggcaa ctcctgatca tcctgctgat cgtgatcatg      60
ctgttcggca ccaagcgcct caagggcctg gctcggacc tgggcgacgc gatcaagggg     120
ttccgcaagt cgatgggtac cgacgaagag aagcccggcg tcgaagaaaa gcagagccac     180
accatcgatg ccgaggcccg caaggtcgaa gacccgacca agaagaactg a              231
```

<210> SEQ ID NO 66
<211> LENGTH: 231
<212> TYPE: DNA
<213> ORGANISM: Artificial
<220> FEATURE:
<223> OTHER INFORMATION: codon optimized Ps tatA gene

<400> SEQUENCE: 66

```
atggggctcg gtggtattag cgtatggcaa ctcctgatta tcctgcttat tgtaattatg      60
ctctttggta cgaagcgtct taaagggttg ggtagcgatt tggggatgc cattaagggt      120
ttccgcaaat caatggggac agatgaagaa aaaccagggg tcgaagaaaa acagtcccac      180
accattgacg ccgaagcacg taaggtggag gacccaacca aaaagaactg a              231
```

<210> SEQ ID NO 67
<211> LENGTH: 119
<212> TYPE: PRT
<213> ORGANISM: Pseudomonas stutzeri

<400> SEQUENCE: 67

```
Met Phe Asp Ile Gly Phe Thr Glu Leu Leu Val Gly Leu Val Ala
1               5                   10                  15
Leu Val Val Leu Gly Pro Glu Arg Leu Pro Gly Ala Val Arg Thr Thr
            20                  25                  30
Gly Leu Trp Val Gly Arg Leu Lys Arg Ser Phe Ser Asn Ile Lys Ala
        35                  40                  45
Glu Val Glu Arg Glu Ile Gly Ala Asp Glu Ile Arg Arg Gln Leu His
    50                  55                  60
Asn Glu Arg Ile Leu Asp Leu Glu Arg Glu Met Lys Ala Met Lys Glu
65                  70                  75                  80
Ser Ile Met Pro Pro Ser Pro Ser Ser Ser Asp Ala Arg Pro Ala
                85                  90                  95
Thr Thr Glu Val Thr Lys Pro Ala Pro Glu Pro Ala Pro Ala Ser Asn
            100                 105                 110
Pro Asp Arg Ser Pro Glu Pro
        115
```

<210> SEQ ID NO 68
<211> LENGTH: 360
<212> TYPE: DNA
<213> ORGANISM: Pseudomonas stutzeri

<400> SEQUENCE: 68

```
atgttcgata tcggtttcac ggagctgctc ctggtggggc tggtggcctt ggtcgtgctc      60
ggccccgagc gtttgcccgg cgcagtgcgc acgaccggat gtgggtcgg ccgcttgaag      120
cgcagcttca gcaatatcaa ggccgaggtc gagcgggaaa tcggcgcgga cgagattcgc      180
cgccaactgc acaacgagcg cattctcgac ctcgaaagag aaatgaaggc gatgaaggaa      240
agcatcatgc cgccctcgcc ctcatcctcc agtgacgctc gcccggcaac gacggaagtg      300
accaaacccg ccccgaacc agccccagct ccaacccgg acagatcgcc tgaaccatga      360
```

<210> SEQ ID NO 69
<211> LENGTH: 360
<212> TYPE: DNA
<213> ORGANISM: Artificial
<220> FEATURE:
<223> OTHER INFORMATION: codon optimized Ps tatB gene

<400> SEQUENCE: 69

```
atgttcgaca tcggttttac cgagctcctc cttgtcgggc tcgtcgcact cgtagtactg      60
ggtccagaac gccttcctgg tgctgtccgt acaactgggc tctgggttgg ccgtttgaaa      120
cgtagcttca gtaatattaa ggcagaggtg gaacgtgaga ttggggcgga cgagatccgt      180
cgccagttgc acaacgaacg cattcttgat ttagaacgtg aaatgaaagc tatgaaggag      240
```
agtatcatgc cacctagtcc ttcttcatcc agtgatgcac gtccagccac aactgaggtg    300
acgaaacctg ccccagagcc tgcacctgcc agtaatccgg atcgcagccc ggagccgtaa    360

<210> SEQ ID NO 70
<211> LENGTH: 266
<212> TYPE: PRT
<213> ORGANISM: Pseudomonas stutzeri

<400> SEQUENCE: 70

```
Met Ser Lys His Ala Ser Asn Asp Gln Glu Met Pro Leu Ile Ala His
1               5                   10                  15

Leu Thr Glu Leu Arg Lys Arg Leu Met Arg Cys Val Val Ala Ile Val
            20                  25                  30

Leu Leu Phe Ala Gly Leu Phe Tyr Phe Ser Gln Gln Ile Tyr Ala Leu
        35                  40                  45

Val Ala Ala Pro Leu Arg Ala Tyr Leu Pro Glu Gly Ala Thr Met Ile
    50                  55                  60

Ala Thr Gly Val Ala Ser Pro Phe Leu Thr Pro Phe Lys Leu Thr Leu
65                  70                  75                  80

Met Val Ala Leu Phe Leu Ser Met Pro Ile Ile Leu His Gln Ile Trp
                85                  90                  95

Gly Phe Ile Ala Pro Gly Leu Tyr Lys His Glu Lys Arg Ile Ala Val
            100                 105                 110

Pro Leu Leu Ile Ser Ser Ile Ile Leu Phe Tyr Ala Gly Met Ala Phe
        115                 120                 125

Ala Tyr Phe Val Val Phe Pro Ile Met Phe Gly Phe Phe Ala Ser Val
    130                 135                 140

Thr Pro Glu Gly Val Glu Met Met Thr Asp Ile Gly Gln Tyr Leu Asp
145                 150                 155                 160

Phe Val Leu Thr Leu Phe Phe Ala Phe Gly Val Ala Phe Glu Ile Pro
                165                 170                 175

Val Ala Thr Phe Leu Leu Ile Trp Val Gly Ile Val Asp Val Ala Thr
            180                 185                 190

Leu Arg Lys Ser Arg Pro Tyr Val Val Gly Cys Phe Val Val Gly
        195                 200                 205

Met Val Leu Thr Pro Pro Asp Val Phe Ser Gln Thr Leu Leu Ala Val
    210                 215                 220

Pro Met Trp Leu Leu Phe Glu Ala Gly Val Ile Cys Gly Ser Met Val
225                 230                 235                 240

Ser Lys Arg Glu Ala Gly Phe Arg Gly Asp Ala Asp Glu Asp Lys Pro
                245                 250                 255

Glu Arg Asp Gln Pro Pro Val Ser Arg Pro
            260                 265
```

<210> SEQ ID NO 71
<211> LENGTH: 801
<212> TYPE: DNA
<213> ORGANISM: Pseudomonas stutzeri

<400> SEQUENCE: 71
atgagcaaac acgctagcaa cgatcaggaa atgccgctga tcgctcacct gaccgaactg    60
cgcaaacgcc tgatgcgctg cgtggtagcg atcgtgctgc tgttcgccgg gttgttctac    120
ttctcgcaac agatctatgc gctggtggcc gcgccgctgc gcgcctacct gccggaaggg    180
gcgaccatga tcgccaccgg cgtcgcctcg ccgttcctga cgccgttcaa gctgacgctg    240

```
atggtggcgc tgttcctgtc gatgccgatc atcctgcacc agatctgggg tttcatcgct      300
cccggcctgt acaagcatga aagcgcatt gccgtaccct tgctgatttc cagcatcatc      360
ctgttctacg ccggcatggc gttcgcctat ttcgtggtct ccccgatcat gttcggcttc      420
ttcgccagcg tgacgcccga aggcgtcgag atgatgaccg acatcggcca ataccctggat     480 ttcgtgctca cgctgttctt cgccttcggc gtggccttcg agatcccggt ggcgaccttt      540
ctgctgatct gggtcggcat cgtcgacgtg caaccctgc gcaagagcag gcctatgtc       600 gtcgtcggct gcttcgtggt cggcatggtg ctgaccccgc cgacgtgtt ctcgcaaacc      660 ctgctcgccg tgccgatgtg gctgctgttc gaagccggtg tgatctgcgg cagcatggtc      720
agcaagcgcg aggcagggtt cgcggcgat gccgacgaag acaagcccga gcgcgaccag      780
ccgcccgtct cgcgcccttg a                                                801

<210> SEQ ID NO 72
<211> LENGTH: 801
<212> TYPE: DNA
<213> ORGANISM: Artificial
<220> FEATURE:
<223> OTHER INFORMATION: codon optimized Ps tatC gene

<400> SEQUENCE: 72
atgtctaaac acgcatctaa tgatcaagaa atgcctctta tcgcgcacct tactgagtta      60
cgcaaacgcc tcatgcgttg tgtcgttgcc atcgttctgc tgtttgcagg gctcttttat     120
tttagccagc aaatctacgc ccttgtggcc gcgccgctcc gcgcctattt accagaaggg     180
gctactatga ttgcaaccgg ggtcgcctct ccttttttga cgccgtttaa gttaactctt     240
atggtagcac tgttttttgtc catgcctatc attttgcacc aaatctgggg ctttatcgct     300
cctgggttat acaaacacga aaaacgcatt gctgtgcctt tgttaatcag ctccatcatt     360
ttgttctacg caggtatggc attcgcttat ttttgttgtct cccgatcat gttcgggttt      420 tttgcgtcag tcacaccgga aggtgtggag atgatgacgg acattgggca ataccctggac     480 tttgttctca cactttttttt tgcgtttggg gtcgcgtttg aaattccggt agcgactttt      540
ctgctgatct gggtcgggat tgtagatgtg gctactcttc gcaaaagccg tccgtacgtc      600
gtcgttggct gctttgttgt ggggatggt ctgactccgc ctgacgtttt ctctcagacc      660
ttgttagctg tgcctatgtg gcttttgttc gaggctggtg tgatctgtgg gtcgatggtg      720
tctaaacgtg aggcgggctt cgcggtgac gcagatgagg acaaaccgga gcgcgatcag      780
ccgccggtct ctcgtccgta a                                                801

<210> SEQ ID NO 73
<211> LENGTH: 82
<212> TYPE: PRT
<213> ORGANISM: Pseudomonas aeruginosa

<400> SEQUENCE: 73

Met Gly Ile Phe Asp Trp Lys His Trp Ile Val Ile Leu Ile Val Val
1               5                   10                  15

Val Leu Val Phe Gly Thr Lys Arg Leu Lys Asn Leu Gly Ser Asp Val
            20                  25                  30

Gly Glu Ala Ile Lys Gly Phe Arg Lys Ala Val Asn Thr Glu Glu Asp
        35                  40                  45

Asp Lys Lys Asp Gln Pro Ala Ala Gln Pro Ala Gln Pro Leu Asn Gln
    50                  55                  60
```

-continued

```
Pro His Thr Ile Asp Ala Gln Ala Gln Lys Val Glu Glu Pro Ala Arg
65                  70                  75                  80

Lys Asp
```

<210> SEQ ID NO 74
<211> LENGTH: 249
<212> TYPE: DNA
<213> ORGANISM: Pseudomonas aeruginosa

<400> SEQUENCE: 74

```
atgggcattt ttgactggaa acactggatc gtcatcctga tcgtcgtggt actggtgttc      60
ggcaccaagc gcctgaagaa cctcggttcc gacgtcggcg aagcgatcaa gggcttccgc     120
aaggcggtga acaccgagga agacgacaag aaggaccagc ccgccgccca gccggcccaa     180
ccgctgaacc agccgcacac catcgacgcc caggcgcaga aggtcgaaga gccggcgcgc     240
aaggactga                                                            249
```

<210> SEQ ID NO 75
<211> LENGTH: 249
<212> TYPE: DNA
<213> ORGANISM: Artificial
<220> FEATURE:
<223> OTHER INFORMATION: codon optimized Pa tatA gene

<400> SEQUENCE: 75

```
atggggattt tcgactggaa gcattggatc gtcatcctca tcgtcgttgt tctcgtcttt      60
gggaccaaac gtctgaaaaa tcttggttcc gatgtcggcg aggctatcaa aggttttcgt     120
aaagctgtca atacagagga agatgataag aaggaccagc ctgcggcaca accagcacag     180
cctctgaacc agccacacac tatcgacgca caggctcaaa aggtagaaga accggcccgt     240
aaagactga                                                            249
```

<210> SEQ ID NO 76
<211> LENGTH: 142
<212> TYPE: PRT
<213> ORGANISM: Pseudomonas aeruginosa

<400> SEQUENCE: 76

```
Met Phe Gly Ile Ser Phe Ser Glu Leu Leu Val Gly Leu Val Ala
1               5                   10                  15

Leu Leu Val Leu Gly Pro Glu Arg Leu Pro Gly Ala Ala Arg Thr Ala
                20                  25                  30

Gly Leu Trp Ile Gly Arg Leu Lys Arg Ser Phe Asn Thr Ile Lys Gln
            35                  40                  45

Glu Val Glu Arg Glu Ile Gly Ala Asp Glu Ile Arg Arg Gln Leu His
50                  55                  60

Asn Glu His Ile Leu Ser Met Glu Arg Glu Ala Gln Lys Leu Leu Ala
65                  70                  75                  80

Pro Leu Thr Gly Gln Asn Pro Ser Gln Glu Pro Gln Pro Pro Thr Val
                85                  90                  95

Glu Ser Pro Ala Pro Pro Ser Val Pro Thr Pro Pro Thr Ser Thr
                100                 105                 110

Pro Ala Val Pro Pro Ala Asp Ala Ala Pro Ala Val Ala Ala
            115                 120                 125

Ser Thr Pro Pro Ser Pro Pro Ser Glu Thr Pro Arg Asn Pro
        130                 135                 140
```

-continued

<210> SEQ ID NO 77
<211> LENGTH: 429
<212> TYPE: DNA
<213> ORGANISM: Pseudomonas aeruginosa

<400> SEQUENCE: 77

```
atgttcggaa tcagcttcag cgaactgttg ctggtcgggt tggtcgccct gctggtgctc      60
ggccccgagc gcctgccggg cgccgcacgt accgccggcc tgtggatcgg ccgcctgaag     120
cgcagtttca ataccatcaa gcaggaagtg aacgggaaa tcggcgcgga cgagatccgc      180
cggcaactgc acaacgagca catcctctcg atggagcgcg aagcgcagaa gctgctggcc     240
ccgctgaccg gccagaatcc ctcgcaggaa ccccagccgc cgacggtcga gagcccggcg     300
ccgccgagcg tacccacgcc gccgccgacc agcacgcctg cggttccgcc cgcggacgcc     360
gcggcaccgc cggcagtcgc tgcctccact ccccccttcgc caccgtccga cgccgcgt     420
aatccatga                                                             429
```

<210> SEQ ID NO 78
<211> LENGTH: 429
<212> TYPE: DNA
<213> ORGANISM: Artificial
<220> FEATURE:
<223> OTHER INFORMATION: codon optimized Pa tatB gene

<400> SEQUENCE: 78

```
atgttcggga tttccttttc agagttgctg ttggtgggcc ttgtggcttt gttggtactc      60
ggtccggagc gtctgccagg cgccgctcgt accgctggtc tgtggatcgg ccgtcttaaa     120
cgttccttca atacgattaa gcaagaagtc gaacgcgaaa ttggggcgga cgaaatccgc     180
cgccagcttc acaacgagca cattctgtct atggagcgcg aagctcaaaa gttattggct     240
cctttgacgg gccagaaccc aagtcaggag cctcagcctc ctacggttga gtccccagca     300
ccaccttccg ttcctacacc tccgccgacc tccacgcctg ctgttcctcc ggcagacgct     360
gcggcccctc cagcagtcgc tgcaagcact cctccttcac caccatcaga gacaccacgc     420
aacccataa                                                             429
```

<210> SEQ ID NO 79
<211> LENGTH: 267
<212> TYPE: PRT
<213> ORGANISM: Pseudomonas aeruginosa

<400> SEQUENCE: 79

```
Met Ser Ala Asp Lys Pro Glu Gln Pro Glu His Asp Gln Glu Met Pro
1               5                   10                  15

Leu Val Ser His Leu Thr Glu Leu Arg Thr Arg Leu Leu Arg Ser Val
            20                  25                  30

Ala Ala Ile Phe Leu Ile Phe Ala Gly Leu Phe Tyr Phe Ser Gln Lys
        35                  40                  45

Ile Tyr Thr Leu Val Ser Glu Pro Leu Arg Arg Phe Leu Pro Glu Gly
    50                  55                  60

Thr Ser Met Ile Ala Thr Asp Val Ala Ser Pro Phe Leu Ala Pro Phe
65                  70                  75                  80

Lys Leu Thr Met Val Val Ala Leu Phe Leu Ala Met Pro Val Ile Leu
                85                  90                  95

Ala Gln Val Trp Gly Phe Ile Ala Pro Gly Leu Tyr Lys His Glu Lys
            100                 105                 110

Arg Val Ala Leu Pro Leu Leu Val Ser Ser Ile Ile Leu Phe Tyr Ala
```

```
              115                 120                 125
Gly Met Ala Phe Ala Tyr Phe Leu Val Phe Pro Met Ile Phe His Phe
        130                 135                 140

Phe Ala Ser Val Thr Pro Glu Gly Val Ala Met Met Thr Asp Ile Asn
145                 150                 155                 160

Ser Tyr Leu Asp Phe Val Leu Thr Leu Phe Ala Phe Gly Val Ala
                165                 170                 175

Phe Glu Ile Pro Val Ala Thr Val Leu Leu Ile Trp Ile Gly Val Val
                180                 185                 190

Asp Val Glu Tyr Leu Lys Lys Ile Arg Pro Tyr Val Ile Ile Gly Cys
                195                 200                 205

Phe Val Val Gly Met Val Leu Thr Pro Pro Asp Ile Phe Ser Gln Thr
        210                 215                 220

Met Leu Ala Val Pro Met Trp Leu Leu Phe Glu Ile Gly Leu Leu Phe
225                 230                 235                 240

Gly Arg Leu Val Arg Lys Arg Gly Glu His Pro Asp Asp Gln Pro Ala
                245                 250                 255

Ser Asp Gly Asp Gln Pro Pro Ala Thr Arg Gln
                260                 265

<210> SEQ ID NO 80
<211> LENGTH: 804
<212> TYPE: DNA
<213> ORGANISM: Pseudomonas aeruginosa

<400> SEQUENCE: 80
atgagcgccg ataaacccga gcagcccgag cacgaccagg aaatgcccct ggtctcgcac      60
ctgaccgaac tgcgtacgcg cctgctccgc agcgtggcgg cgatcttcct gatcttcgcc     120
ggcctgttct acttctcgca gaagatctac accctggtct ccgagccgtt cgccgcgcttc   180 cttccggaag caccagcat gatcgccacc gacgtcgcct cgccgttcct cgcgccgttc     240
aagctgacca tggtggtggc gctgttcctc gccatgccgg tgatcctcgc gcaggtctgg    300
ggcttcatcg cgcccggcct gtacaagcac gagaagcgcg tggcgctgcc gctgctggtg    360
tccagcatca tcctgttcta cgccgggatg gccttcgcct acttcctggt gttcccgatg    420
atcttccact tcttcgccag cgtgacgccc gagggcgtgg cgatgatgac ggacatcaac    480
agctacctgg acttcgtcct gaccctgttc ttcgccttcg gcgtcgcctt cgagatcccg    540
gtggccacgg tgctgctgat ctggatcggg gtggtcgacg tcgagtacct gaagaagatc    600
cgcccgtacg tgatcatcgg ctgcttcgtg gtcggcatgg tcctgacccc gccggacatc    660
ttctcccaga ccatgctcgc ggtgccgatg tggctgctgt tcgagatcgg cctgctgttc    720
ggccgcctgg tacgcaagcg cggcgagcat ccggacgacc aaccggccag cgacggcgac    780
cagcctccgg ccacccgcca gtga                                             804

<210> SEQ ID NO 81
<211> LENGTH: 804
<212> TYPE: DNA
<213> ORGANISM: Artificial
<220> FEATURE:
<223> OTHER INFORMATION: codon optimized Pa tatC gene

<400> SEQUENCE: 81
atgtccgcag ataaacctga gcagccagaa catgatcaag aaatgccgtt ggtgagccat      60
ttgacagagc ttcgtacacg tctcctccgc tcggttgcgg ccatcttttt gatctttgcc    120
```

```
ggtctctttt acttcagcca gaagatttat acattggttt ccgaaccact tcgtcgtttt      180
ttgcctgaag ggacatctat gattgcaacg gacgttgcgt ccccattctt agctcctttc      240
aaactgacga tggtcgtggc tttatttta gcgatgccgg taatcctcgc ccaagtgtgg       300
ggctttattg cgccgggtct gtacaaacac gagaaacgtg tggctttgcc tttactggta      360
tcttccatta ttttgtttta tgcggggatg gcgttcgctt acttcttggt gtttccaatg      420
atctttcatt tctttgcgag cgtgacacct gaggggtcg cgatgatgac cgacatcaac       480
agttaccttg actttgtgtt gaccttattc tttgcctttg gggtagcctt cgaaatcccg      540
gtggctacgg tgcttttgat ttggatcggc gtggtggatg ttgagtattt aaagaaaatt      600
cgtccttacg ttatcattgg gtgttttgtc gtcgggatgg tcctcacgcc tcctgacatt      660
ttctctcaga ccatgttggc ggtcccgatg tggctgcttt ttgaaattgg ccttttattt      720
ggtcgtttgg ttcgtaaacg tggtgagcat ccagacgacc agccagcgtc tgacggcgat      780
cagccgccag caacacgtca ataa                                             804

<210> SEQ ID NO 82
<211> LENGTH: 108
<212> TYPE: PRT
<213> ORGANISM: Pseudomonas versutus

<400> SEQUENCE: 82

Met His Ala Pro Ser Pro Met Ala Leu Leu Ile Ala Ile Val Val
1               5                   10                  15

Leu Val Leu Phe Gly Arg Gly Lys Val Ser Ser Leu Met Gly Glu Val
            20                  25                  30

Gly Lys Gly Ile Thr Ala Phe Lys Lys Gly Val Lys Glu Gly Ala Glu
        35                  40                  45

Asp Ile Asp Ala Ala Ala His Ser Glu Pro Lys Glu Leu Glu Gln Leu
    50                  55                  60

Lys Thr Ala Asp Asp Ile Glu Arg Ala Arg Ala Asp Leu Ala Ala Glu
65                  70                  75                  80

Arg Ala Lys Leu Asp Ala Glu Arg Ala Arg Thr Gly Ala Asp Ser Ala
                85                  90                  95

Leu Arg Asp Val Thr Pro Thr Asp Ser Thr Lys Leu
                100                 105

<210> SEQ ID NO 83
<211> LENGTH: 327
<212> TYPE: DNA
<213> ORGANISM: Pseudomonas versutus

<400> SEQUENCE: 83
atgcacgcac cttcacccat ggcgctattg ctgatcgcaa tcgtcgttct ggttctttc        60 gggcgcggca aggtctcgtc cctgatgggc gaggtcggca aggggatcac cgccttcaag      120
aaaggcgtca aggaaggcgc cgaggatatc gacgccgccg cccacagcga gcccaaggaa      180
ctggagcagc tgaagaccgc cgacgacatc gagcgcgccc gcgccgacct ggccgccgaa      240
cgcgccaagc ttgacgccga gcgcgcccgc accggcgccg acagcgcgct gcgcgacgtg      300
acgccgaccg actcgaccaa gctctga                                          327

<210> SEQ ID NO 84
<211> LENGTH: 327
<212> TYPE: DNA
<213> ORGANISM: Artificial
<220> FEATURE:
```

<223> OTHER INFORMATION: codon optimized Pv tatA gene

<400> SEQUENCE: 84

```
atgcacgccc cgtctcctat ggcattactt ttaattgcta tcgtcgttct cgtactcttt    60
gggcgcggca aagtctcatc tctgatgggc gaggtcggca agggtattac agcgtttaag   120
aaaggcgtaa agaaggtgc agaagatatt gacgcggctg ctcattcgga gcctaaagag   180
ctggagcagt tgaaaacagc tgacgatatt gaacgtgcac gtgcagactt ggctgcggaa   240
cgtgcaaagc tggacgcaga gcgtgcacgc acaggggcag attctgccct tcgtgacgtt   300
actcctactg attccacgaa actgtaa                                       327
```

<210> SEQ ID NO 85
<211> LENGTH: 169
<212> TYPE: PRT
<213> ORGANISM: Pseudomonas versutus

<400> SEQUENCE: 85

```
Met Leu Asp Ile Gly Trp Ser Glu Leu Leu Ile Gly Val Val Ala
1               5                   10                  15
Leu Ile Val Ile Gly Pro Lys Asp Leu Pro Lys Leu Phe His Thr Leu
            20                  25                  30
Gly Arg Ile Thr Ala Arg Ala Arg Ser Met Ala Arg Glu Phe Ser Ser
        35                  40                  45
Ala Met Glu Asp Ala Ala Lys Ser Ser Gly Leu Asp Asp Ala Ala Lys
    50                  55                  60
Thr Leu Lys Asp Val Asn Ala Leu Ser Ser Lys Arg Ala Leu Gly Leu
65                  70                  75                  80
Asp Ala Leu Glu Arg Ala Thr Glu Arg Phe Glu Lys Trp Asp Pro Leu
                85                  90                  95
Asn Pro Lys Asp Glu Ala Gly Arg Lys Ala Pro Val Pro Asp Pro Ser
            100                 105                 110
Ala Pro Leu Pro Pro Gln Pro Ala Ala Asn Gly Ser Ala Pro Ala
        115                 120                 125
Ala Pro Pro Ala Asp Leu Pro Pro Ala Pro Gly Val Ala Ala Pro Pro
    130                 135                 140
Val Ala Ala Glu Asp Ala Leu Asp Thr Ala Glu Gly Arg Arg Arg Leu
145                 150                 155                 160
His Ala Val Arg Arg Ser Asp Arg Ala
                165
```

<210> SEQ ID NO 86
<211> LENGTH: 510
<212> TYPE: DNA
<213> ORGANISM: Pseudomonas versutus

<400> SEQUENCE: 86

```
atgttggata tcggctggag cgagttgctg ctgatcggcg tggtggcgct gatcgtcatc    60
ggacccaagg atctgcccaa gctgtttcac acgctgggcc ggatcaccgc gcgcgcgcgc   120
tcgatggcgc gcgagttcag cagcgcgatg gaggatgcgg ccaagagctc gggccttgac   180
gacgcggcca agacgctcaa ggacgtgaac gcgctgagct cgaaacgcgc gctgggcctt   240
gacgcgctgg aacgcgcgac cgagcggttc gagaaatggg atccgctgaa ccccaaggac   300
gaggccggcc gcaaggcgcc cgtccccgat ccctcggccc cgctgccgcc gcagcccgcg   360
gcgaacggca gcgacgcgcc tgccgccccg cccgccgacc tgccgcccgc gccgggcgtc   420
```

```
gccgccccgc cggtagccgc cgaggatgcg ctggacacgg ccgaggggcg ccgccgcctg    480
cacgccgtgc gccggtccga ccgcgcttga                                     510
```

<210> SEQ ID NO 87
<211> LENGTH: 510
<212> TYPE: DNA
<213> ORGANISM: Artificial
<220> FEATURE:
<223> OTHER INFORMATION: codon optimized Pv tatB gene

<400> SEQUENCE: 87

```
atgttggata ttggttggtc agagcttctt ctgatcggtg tagtagccct gatcgtgatt     60
ggtccaaagg acctcccaaa gttattccat acgttagggc gtattaccgc gcgcgctcgc    120
tcgatggctc gcgagttttc ttcggcaatg gaggacgccg caaaatcgtc tggtcttgac    180
gacgccgcta agacgctcaa ggatgttaac gcgctttcat cgaagcgtgc actcgggctc    240
gacgcgctgg agcgtgcaac cgaacgcttt gaaaagtggg accgcttaa cccaaaagat    300 gaagcagggc gcaaggcacc tgtgcctgat ccatcagctc cgcttccacc gcagcctgct    360
gcaaatggct cggatgcacc tgctgctcct cctgcggatt tgccaccagc cccgggggtg    420
gctgctccac tgtcgcagc tgaggatgcg ctcgacactg cagaggggcg tcgtcgtttg    480
catgcggttc gtcgtagtga ccgtgcttaa                                     510
```

<210> SEQ ID NO 88
<211> LENGTH: 286
<212> TYPE: PRT
<213> ORGANISM: Pseudomonas versutus

<400> SEQUENCE: 88

```
Met Lys Ser Ala Lys Pro Asp Asp Ile Asp Thr Ser Ala Pro Leu
1               5                  10                  15

Ile Glu His Leu Ala Glu Leu Arg Thr Arg Leu Ile Trp Ser Val Leu
                20                  25                  30

Ala Phe Val Val Ala Met Val Leu Cys Tyr Phe Val Trp Asn Pro Ile
            35                  40                  45

Phe Asp Phe Leu Thr Gln Pro Ile Cys His Ala Leu Glu Lys Arg Asp
        50                  55                  60

Gln Ala Cys Gly Leu Ile Leu Leu Lys Leu Gln Glu Gly Phe Phe Val
65                  70                  75                  80

Ala Met Arg Ile Ala Phe Phe Gly Gly Phe Val Leu Ala Phe Pro Val
                85                  90                  95

Val Gly Tyr Gln Leu Trp Arg Phe Val Ala Pro Gly Leu Tyr Arg Ser
            100                 105                 110

Glu Lys Asn Ala Leu Leu Pro Phe Leu Val Ala Ser Pro Val Met Phe
        115                 120                 125

Leu Ile Gly Ala Ala Phe Ala Tyr Tyr Ile Ile Leu Pro Trp Ala Phe
    130                 135                 140

Asp Phe Phe Leu Gly Phe Gln Gln Gly Pro Ala Ala Gln Pro Ala Asp
145                 150                 155                 160

Pro Ala Ala Ala Ala Ala Gly Ala Ala Gly Ala Ala Gly Ala Glu
                165                 170                 175

Gln Pro Trp Ala Gly Ile Val Phe Gln Gly Ser Val Glu Glu Tyr Leu
            180                 185                 190

Ala Leu Thr Thr Lys Phe Ile Leu Ala Phe Gly Leu Ser Phe Gln Leu
        195                 200                 205
```

```
Pro Val Ala Leu Thr Leu Met Gly Lys Ala Gly Leu Val Ser Ser Glu
    210                 215                 220

Gly Leu Ala Ser Val Arg Arg Tyr Ala Ile Val Val Ile Leu Ile Leu
225                 230                 235                 240

Ala Ala Met Val Thr Pro Pro Asp Val Ile Ser Gln Ile Val Leu Phe
                245                 250                 255

Ser Val Ile Tyr Gly Leu Tyr Glu Val Ser Ile Phe Leu Val Arg Arg
                260                 265                 270

Met Glu Lys Lys Arg Glu Leu Glu Glu Gln Glu Ala Asp Val
    275                 280                 285
```

<210> SEQ ID NO 89
<211> LENGTH: 861
<212> TYPE: DNA
<213> ORGANISM: Pseudomonas versutus

<400> SEQUENCE: 89

```
atgaaatctg ccaagccgga cgatatcgac gacacatccg cccccctgat cgagcatctg      60
gccgagctgc gcacgcggct gatctggtcg gttctcgcct cgtcgtggc gatggtgctg      120
tgctatttcg tctggaaccc gatcttcgac ttcctgaccc agccgatctg ccacgcgctg     180
gaaaagcgcg accaggcctg cggtctgatc ctgctgaaac tgcaggaggg gttcttcgtc    240
gccatgcgca tcgccttctt cggcggtttc gtgctggcct ttccggtggt cggctaccag    300
ctgtggcgtt tcgttgcgcc ggggctttac cgcagcgaaa agaacgcgct gctgcccttc    360
ctggtcgcct cgccggtgat gttcctgatc ggcgcggcct cgcctatta tcatcatcctg   420
ccctgggcct tcgacttctt cctgggcttc cagcaaggtc cggcggcaca gcccgccgat    480
ccggcggccg ccgccgcggc tggggcggcg ggtgcggcgg gtgccgagca gccctgggcc    540
ggcatcgtct tccagggctc ggtcgaggaa tacctggcgc tgaccaccaa gttcatcctg    600
gccttcggcc tgtccttcca gttgccggtg gcgctgacgc tgatgggcaa ggcggggctg    660
gtgtcctcgg aagggctggc cagcgtgcgc cgctatgcca tcgtggtgat cctgatcctt    720
gccgccatgg tcacgccgcc cgatgtcatc agccagatcg tgctgttctc ggtgatctac    780
gggctttacg aggtgtcgat cttcctggtg cggcggatgg agaagaaacg cgagctggaa    840
gaacaggaag ccgatgtctg a                                               861
```

<210> SEQ ID NO 90
<211> LENGTH: 861
<212> TYPE: DNA
<213> ORGANISM: Artificial
<220> FEATURE:
<223> OTHER INFORMATION: codon optimized Pv tatC gene

<400> SEQUENCE: 90

```
atgaaatccg ccaaaccaga tgatattgac gatacaagtg ccccgcttat tgagcacctg     60
gcagagttac gtactcgcct gatctggtca gtacttgctt cgttgtggc gatggtatta    120
tgctactttg tctggaaccc tatctttgat tttttgactc aacctatttg tcatgcattg    180
gaaaagcgtg atcaagcctg tggtcttatt ctcttaaagt tgcaagaggg gttctttgtg    240
gcgatgcgta ttgcattctt tggcggcttt gtgttggcgt tcccggtcgt ggggtaccag   300
ctctggcgtt tcgtcgctcc aggtctgtat cgtagcgaga agaatgctct gttaccattt    360
ctggtagcct caccggttat gtttctgatt ggtgctgcct ttgcatacta cattatcctt    420
ccgtgggctt tcgacttctt tctcggtttt caacagggtc cggcggcaca gcctgcagat    480
```

-continued

```
ccagccgccg ctgcagcagc tggtgctgca ggtgcagctg gtgccgaaca accgtgggcc      540
gggatcgtat tccaaggctc ggtggaagag tacctcgctt taacgactaa attcattctg      600
gcgttcgggc tttcattcca actgcctgtc gcattgactt taatggggaa ggcaggctta      660
gtttccagtg aagggctcgc tagtgtgcgc cgttatgcca ttgtggtaat tcttatcctc      720
gcagcgatgg ttaccccgcc tgatgttatc agccaaatcg tcttattttc tgtcatctat      780
gggctgtatg aagtctccat ctttctggtg cgtcgcatgg agaagaaacg tgagctggag      840
gagcaagaag ccgacgttta a                                                861
```

<210> SEQ ID NO 91
<211> LENGTH: 49
<212> TYPE: DNA
<213> ORGANISM: Artificial
<220> FEATURE:
<223> OTHER INFORMATION: primer

<400> SEQUENCE: 91

```
ctttaagaag gagatatacc atgtccgaca atgacagcaa aaatacgcc                49
```

<210> SEQ ID NO 92
<211> LENGTH: 29
<212> TYPE: DNA
<213> ORGANISM: Artificial
<220> FEATURE:
<223> OTHER INFORMATION: primer

<400> SEQUENCE: 92

```
tcatgctggt tctacaatca tgcgaccta                                      29
```

<210> SEQ ID NO 93
<211> LENGTH: 66
<212> TYPE: DNA
<213> ORGANISM: Artificial
<220> FEATURE:
<223> OTHER INFORMATION: primer

<400> SEQUENCE: 93

```
tgattgtaga accagcatga ctttaagaag gagatatacc atgaagccgt taggtttcgc      60
cgtcgt                                                                66
```

<210> SEQ ID NO 94
<211> LENGTH: 26
<212> TYPE: DNA
<213> ORGANISM: Artificial
<220> FEATURE:
<223> OTHER INFORMATION: primer

<400> SEQUENCE: 94

```
tcaaggctca accacttgga ccactg                                         26
```

<210> SEQ ID NO 95
<211> LENGTH: 69
<212> TYPE: DNA
<213> ORGANISM: Artificial
<220> FEATURE:
<223> OTHER INFORMATION: primer

<400> SEQUENCE: 95

```
tccaagtggt tgagccttga ctttaagaag gagatatacc atgatgaata atttgtaccg      60
caccggtgc                                                             69
```

```
<210> SEQ ID NO 96
<211> LENGTH: 49
<212> TYPE: DNA
<213> ORGANISM: Artificial
<220> FEATURE:
<223> OTHER INFORMATION: primer

<400> SEQUENCE: 96
gctttgttag cagccggatc tcaatggcct gcatggtcat tatgttctg                49

<210> SEQ ID NO 97
<211> LENGTH: 45
<212> TYPE: DNA
<213> ORGANISM: Artificial
<220> FEATURE:
<223> OTHER INFORMATION: primer

<400> SEQUENCE: 97
ctttaagaag gagatatacc atgtccgatg ataccaaatc cccgc                   45

<210> SEQ ID NO 98
<211> LENGTH: 24
<212> TYPE: DNA
<213> ORGANISM: Artificial
<220> FEATURE:
<223> OTHER INFORMATION: primer

<400> SEQUENCE: 98
tcaagccttc tccaccagca tccg                                          24

<210> SEQ ID NO 99
<211> LENGTH: 63
<212> TYPE: DNA
<213> ORGANISM: Artificial
<220> FEATURE:
<223> OTHER INFORMATION: primer

<400> SEQUENCE: 99
tgctggtgga aaggcttga ctttaagaag gagatatacc atgcgcgcac ttcgtttctc    60
ggc                                                                 63

<210> SEQ ID NO 100
<211> LENGTH: 25
<212> TYPE: DNA
<213> ORGANISM: Artificial
<220> FEATURE:
<223> OTHER INFORMATION: primer

<400> SEQUENCE: 100
tcagaggttc tccgcaggga tacgt                                         25

<210> SEQ ID NO 101
<211> LENGTH: 64
<212> TYPE: DNA
<213> ORGANISM: Artificial
<220> FEATURE:
<223> OTHER INFORMATION: primer

<400> SEQUENCE: 101
tccctgcgga gaacctctga ctttaagaag gagatatacc atgcaacgtc acccctccc    60 gctg                                                                64

<210> SEQ ID NO 102
<211> LENGTH: 44
<212> TYPE: DNA
```

<213> ORGANISM: Artificial
<220> FEATURE:
<223> OTHER INFORMATION: primer

<400> SEQUENCE: 102
gctttgttag cagccggatc ttaatgagcc gggtggcggt gtgg       44

<210> SEQ ID NO 103
<211> LENGTH: 49
<212> TYPE: DNA
<213> ORGANISM: Artificial
<220> FEATURE:
<223> OTHER INFORMATION: primer

<400> SEQUENCE: 103
ctttaagaag gagatatacc atggaaacaa aacagcagaa cggtttatc       49

<210> SEQ ID NO 104
<211> LENGTH: 27
<212> TYPE: DNA
<213> ORGANISM: Artificial
<220> FEATURE:
<223> OTHER INFORMATION: primer

<400> SEQUENCE: 104
tcacgcagct tttggttcca ccatcat       27

<210> SEQ ID NO 105
<211> LENGTH: 75
<212> TYPE: DNA
<213> ORGANISM: Artificial
<220> FEATURE:
<223> OTHER INFORMATION: primer

<400> SEQUENCE: 105
tggaaccaaa agctgcgtga ctttaagaag gagatatacc atgaaaattt tgcgtcttgt       60
gttaacaatt gcgtc       75

<210> SEQ ID NO 106
<211> LENGTH: 28
<212> TYPE: DNA
<213> ORGANISM: Artificial
<220> FEATURE:
<223> OTHER INFORMATION: primer

<400> SEQUENCE: 106
ttacgcttca attttacgtg tcgcattc       28

<210> SEQ ID NO 107
<211> LENGTH: 64
<212> TYPE: DNA
<213> ORGANISM: Artificial
<220> FEATURE:
<223> OTHER INFORMATION: primer

<400> SEQUENCE: 107
cacgtaaaat tgaagcgtaa ctttaagaag gagatatacc atgcgccacg ctctcttgct       60
tgtg       64

<210> SEQ ID NO 108
<211> LENGTH: 44
<212> TYPE: DNA
<213> ORGANISM: Artificial
<220> FEATURE:
<223> OTHER INFORMATION: primer

<400> SEQUENCE: 108
gctttgttag cagccggatc ttaggtcgcc ggttctttag gctg         44

<210> SEQ ID NO 109
<211> LENGTH: 39
<212> TYPE: DNA
<213> ORGANISM: Artificial
<220> FEATURE:
<223> OTHER INFORMATION: primer

<400> SEQUENCE: 109
ataaggagat ataccatgcg cgcttgctac actctcgcc              39

<210> SEQ ID NO 110
<211> LENGTH: 46
<212> TYPE: DNA
<213> ORGANISM: Artificial
<220> FEATURE:
<223> OTHER INFORMATION: primer

<400> SEQUENCE: 110
ggtatatctc cttcttaaag ttagctatga ggacgctgag tcgtgt      46

<210> SEQ ID NO 111
<211> LENGTH: 44
<212> TYPE: DNA
<213> ORGANISM: Artificial
<220> FEATURE:
<223> OTHER INFORMATION: primer

<400> SEQUENCE: 111
ctttaagaag gagatataca tgaaccaagt gtggaacatt gcgc         44

<210> SEQ ID NO 112
<211> LENGTH: 40
<212> TYPE: DNA
<213> ORGANISM: Artificial
<220> FEATURE:
<223> OTHER INFORMATION: primer

<400> SEQUENCE: 112
tggctgctgc ccatgtcaag ctaagcgacg acggaaaatg             40

<210> SEQ ID NO 113
<211> LENGTH: 41
<212> TYPE: DNA
<213> ORGANISM: Artificial
<220> FEATURE:
<223> OTHER INFORMATION: primer

<400> SEQUENCE: 113
gaaggagata tacatatggg gctcggtggt attagcgtat g           41

<210> SEQ ID NO 114
<211> LENGTH: 26
<212> TYPE: DNA
<213> ORGANISM: Artificial
<220> FEATURE:
<223> OTHER INFORMATION: primer

<400> SEQUENCE: 114
ttacggacga gagaccggcg gctgat                            26

<210> SEQ ID NO 115

```
<211> LENGTH: 68
<212> TYPE: DNA
<213> ORGANISM: Artificial
<220> FEATURE:
<223> OTHER INFORMATION: primer

<400> SEQUENCE: 115
cgccggtctc tcgtccgtaa ctttaagaag gagatatacc atggggcgtg cgagcctgca    60
accagtaa                                                             68

<210> SEQ ID NO 116
<211> LENGTH: 42
<212> TYPE: DNA
<213> ORGANISM: Artificial
<220> FEATURE:
<223> OTHER INFORMATION: primer

<400> SEQUENCE: 116
ggtatatctc cttcttaaag tcactgctct gcccccgccc cg                       42

<210> SEQ ID NO 117
<211> LENGTH: 46
<212> TYPE: DNA
<213> ORGANISM: Artificial
<220> FEATURE:
<223> OTHER INFORMATION: primer

<400> SEQUENCE: 117
ctttaagaag gagatatacc atgaacgctg tggaaattca agggt                    46

<210> SEQ ID NO 118
<211> LENGTH: 40
<212> TYPE: DNA
<213> ORGANISM: Artificial
<220> FEATURE:
<223> OTHER INFORMATION: primer

<400> SEQUENCE: 118
attgagatct gccatattat acgcgccctt ctgcggcctg                          40

<210> SEQ ID NO 119
<211> LENGTH: 37
<212> TYPE: DNA
<213> ORGANISM: Artificial
<220> FEATURE:
<223> OTHER INFORMATION: primer

<400> SEQUENCE: 119
ataaggagat ataccatggc agggcgccgt gctgggc                             37

<210> SEQ ID NO 120
<211> LENGTH: 42
<212> TYPE: DNA
<213> ORGANISM: Artificial
<220> FEATURE:
<223> OTHER INFORMATION: primer

<400> SEQUENCE: 120
ggtatatctc cttcttaaag ttaagggcga ggctccgcgg ct                       42

<210> SEQ ID NO 121
<211> LENGTH: 43
<212> TYPE: DNA
<213> ORGANISM: Artificial
<220> FEATURE:
<223> OTHER INFORMATION: primer
```

```
<400> SEQUENCE: 121
ctttaagaag gagatataca tgccggtcgt gtggacgatt gca            43

<210> SEQ ID NO 122
<211> LENGTH: 41
<212> TYPE: DNA
<213> ORGANISM: Artificial
<220> FEATURE:
<223> OTHER INFORMATION: primer

<400> SEQUENCE: 122
tggctgctgc ccatgttaaa ttgggcgacg gcggaacaag c              41

<210> SEQ ID NO 123
<211> LENGTH: 44
<212> TYPE: DNA
<213> ORGANISM: Artificial
<220> FEATURE:
<223> OTHER INFORMATION: primer

<400> SEQUENCE: 123
gaaggagata tacatatggg gattttcgac tggaagcatt ggat           44

<210> SEQ ID NO 124
<211> LENGTH: 27
<212> TYPE: DNA
<213> ORGANISM: Artificial
<220> FEATURE:
<223> OTHER INFORMATION: primer

<400> SEQUENCE: 124
ttattgacgt gttgctggcg gctgatc                              27

<210> SEQ ID NO 125
<211> LENGTH: 60
<212> TYPE: DNA
<213> ORGANISM: Artificial
<220> FEATURE:
<223> OTHER INFORMATION: primer

<400> SEQUENCE: 125
cgccagcaac acgtcaataa ctttaagaag gagatatacc atggcggggt tagcagcgct   60

<210> SEQ ID NO 126
<211> LENGTH: 19
<212> TYPE: DNA
<213> ORGANISM: Artificial
<220> FEATURE:
<223> OTHER INFORMATION: primer

<400> SEQUENCE: 126
ttatgggcgt tcaccctga                                       19

<210> SEQ ID NO 127
<211> LENGTH: 43
<212> TYPE: DNA
<213> ORGANISM: Artificial
<220> FEATURE:
<223> OTHER INFORMATION: primer

<400> SEQUENCE: 127
ctttaagaag gagatatacc atgagccttg tggaaattga cgg            43

<210> SEQ ID NO 128
```

```
<211> LENGTH: 36
<212> TYPE: DNA
<213> ORGANISM: Artificial
<220> FEATURE:
<223> OTHER INFORMATION: primer

<400> SEQUENCE: 128
attgagatct gccatattat ggacatggcg ttgcac                                    36

<210> SEQ ID NO 129
<211> LENGTH: 42
<212> TYPE: DNA
<213> ORGANISM: Artificial
<220> FEATURE:
<223> OTHER INFORMATION: primer

<400> SEQUENCE: 129
ataaggagat ataccatgcg tagtcttttg acacttgcgc tg                             42

<210> SEQ ID NO 130
<211> LENGTH: 49
<212> TYPE: DNA
<213> ORGANISM: Artificial
<220> FEATURE:
<223> OTHER INFORMATION: primer

<400> SEQUENCE: 130
ggtatatctc cttcttaaag tcaatgacta gttaaatcgt ctgggtcaa                      49

<210> SEQ ID NO 131
<211> LENGTH: 45
<212> TYPE: DNA
<213> ORGANISM: Artificial
<220> FEATURE:
<223> OTHER INFORMATION: primer

<400> SEQUENCE: 131
ctttaagaag gagatataca tgatccgtcg cattctcagt acagc                          45

<210> SEQ ID NO 132
<211> LENGTH: 40
<212> TYPE: DNA
<213> ORGANISM: Artificial
<220> FEATURE:
<223> OTHER INFORMATION: primer

<400> SEQUENCE: 132
tggctgctgc ccatgttacg gagtaacctt acggaacgcc                                40

<210> SEQ ID NO 133
<211> LENGTH: 41
<212> TYPE: DNA
<213> ORGANISM: Artificial
<220> FEATURE:
<223> OTHER INFORMATION: primer

<400> SEQUENCE: 133
gaaggagata tacatatgca cgccccgtct cctatggcat t                              41

<210> SEQ ID NO 134
<211> LENGTH: 26
<212> TYPE: DNA
<213> ORGANISM: Artificial
<220> FEATURE:
<223> OTHER INFORMATION: primer

<400> SEQUENCE: 134
```
ttaaacgtcg gcttcttgct cctcca                                          26

<210> SEQ ID NO 135
<211> LENGTH: 64
<212> TYPE: DNA
<213> ORGANISM: Artificial
<220> FEATURE:
<223> OTHER INFORMATION: primer

<400> SEQUENCE: 135
agcaagaagc cgacgtttaa ctttaagaag gagatatacc atgtcacgcc gtcgtttcct     60
gact                                                                  64

<210> SEQ ID NO 136
<211> LENGTH: 24
<212> TYPE: DNA
<213> ORGANISM: Artificial
<220> FEATURE:
<223> OTHER INFORMATION: primer

<400> SEQUENCE: 136
tcaggcaccg cgaggagccg cctc                                            24

<210> SEQ ID NO 137
<211> LENGTH: 46
<212> TYPE: DNA
<213> ORGANISM: Artificial
<220> FEATURE:
<223> OTHER INFORMATION: primer

<400> SEQUENCE: 137
ctttaagaag gagatatacc atgacaagta cactgacgat tagccg                    46

<210> SEQ ID NO 138
<211> LENGTH: 41
<212> TYPE: DNA
<213> ORGANISM: Artificial
<220> FEATURE:
<223> OTHER INFORMATION: primer

<400> SEQUENCE: 138
attgagatct gccatattac tgcccgtcgc ggcgactaaa g                         41

<210> SEQ ID NO 139
<211> LENGTH: 1430
<212> TYPE: DNA
<213> ORGANISM: Artificial
<220> FEATURE:
<223> OTHER INFORMATION: primer

<400> SEQUENCE: 139
atggggctcg gtggtattag cgtatggcaa ctcctgatta tcctgcttat tgtaattatg     60
ctctttggta cgaagcgtct taaagggttg ggtagcgatt tggggatgc cattaagggt     120 ttccgcaaat caatggggac agatgaagaa aaaccagggg tcgaagaaaa acagtcccac    180
accattgacg ccgaagcacg taaggtggag gacccaacca aaaagaactg actttaagaa    240
ggagatatac atgttcgaca tcggttttac cgagctcctc cttgtcgggc tcgtcgcact    300
cgtagtactg ggtccagaac gccttcctgg tgctgtccgt acaactgggc tctgggttgg    360
ccgtttgaaa cgtagcttca gtaatattaa ggcagaggtg gaacgtgaga ttggggcgga    420
cgagatccgt cgccagttgc acaacgaacg cattcttgat ttagaacgtg aaatgaaagc    480

```
tatgaaggag agtatcatgc cacctagtcc ttcttcatcc agtgatgcac gtccagccac    540
aactgaggtg acgaaacctg ccccagagcc tgcacctgcc agtaatccgg atcgcagccc    600
ggagccgtaa ctttaagaag gagatataca tgtctaaaca cgcatctaat gatcaagaaa    660
tgcctcttat cgcgcacctt actgagttac gcaaacgcct catgcgttgt gtcgttgcca    720
tcgttctgct gtttgcaggg ctcttttatt ttagccagca aatctacgcc cttgtggccg    780
cgccgctccg cgcctattta ccagaagggg ctactatgat tgcaaccggg gtcgcctctc    840
cttttttgac gccgtttaag ttaactctta tggtagcact gttttttgtcc atgcctatca    900 ttttgcacca aatctggggc tttatcgctc ctgggttata caaacacgaa aaacgcattg    960
ctgtgccttt gttaatcagc tccatcattt tgttctacgc aggtatggca ttcgcttatt   1020
ttgttgtctt cccgatcatg ttcgggtttt tgcgtcagt cacaccggaa ggtgtggaga    1080
tgatgacgga cattgggcaa tacctggact tgttctcac acttttttt gcgtttgggg     1140 tcgcgtttga aattccggta gcgactttc tgctgatctg ggtcgggatt gtagatgtgg    1200
ctactcttcg caaaagccgt ccgtacgtcg tcgttggctg ctttgttgtg gggatggttc   1260
tgactccgcc tgacgttttc tctcagacct tgttagctgt gcctatgtgg cttttgttcg   1320
aggctggtgt gatctgtggg tcgatggtgt ctaaacgtga ggcgggcttt cgcggtgacg   1380
cagatgagga caaaccggag cgcgatcagc cgccggtctc tcgtccgtaa               1430
```

<210> SEQ ID NO 140  
<211> LENGTH: 1520  
<212> TYPE: DNA  
<213> ORGANISM: Artificial  
<220> FEATURE:  
<223> OTHER INFORMATION: primer

<400> SEQUENCE: 140

```
atggggattt tcgactggaa gcattggatc gtcatcctca tcgtcgttgt tctcgtcttt     60
gggaccaaac gtctgaaaaa tcttggttcc gatgtcggcg aggctatcaa aggttttcgt   120
aaagctgtca atacagagga agatgataag aaggaccagc ctgcggcaca accagcacag   180
cctctgaacc agccacacac tatcgacgca caggctcaaa aggtagaaga accggcccgt   240
aaagactgac tttaagaagg agatatacat gttcgggatt ccttttcag agttgctgtt   300 ggtgggcctt gtggctttgt tggtactcgg tccggagcgt ctgccaggcg ccgctcgtac   360
cgctggtctg tggatcggcc gtcttaaacg ttccttcaat acgattaagc aagaagtcga   420
acgcgaaatt ggggcggacg aaatccgccg ccagcttcac aacgagcaca ttctgtctat   480
ggagcgcgaa gctcaaaagt tattggctcc tttgacgggc cagaacccaa gtcaggagcc   540
tcagcctcct acggttgagt ccccagcacc accttccgtt cctacacctc cgccgacctc   600
cacgcctgct gttcctccgg cagacgctgc ggcccctcca gcagtcgctg caagcactcc   660
tccttcacca ccatcagaga caccacgcaa cccataactt taagaaggag atatacatgt   720
ccgcagataa acctgagcag ccagaacatg atcaagaaat gccgttggtg agccatttga   780
cagagcttcg tacacgtctc ctccgctcgg ttgcggccat cttttgatc tttgccggtc    840 tcttttactt cagccagaag atttatacat tggtttccga accacttcgt cgttttttgc    900
ctgaagggac atctatgatt gcaacggacg ttgcgtcccc attcttagct cctttcaaac   960
tgacgatggt cgtggcttta ttttagcga tgccggtaat cctcgcccaa gtgtgggggt   1020
ttattgcgcc gggtctgtac aaacacgaga acgtgtggc tttgcctta ctggtatctt    1080 ccattatttt gttttatgcg gggatggcgt tcgcttactt cttggtgttt ccaatgatct   1140
```

```
ttcatttctt tgcgagcgtg acacctgagg gggtcgcgat gatgaccgac atcaacagtt      1200
accttgactt tgtgttgacc ttattctttg cctttggggt agccttcgaa atcccggtgg      1260
ctacggtgct tttgatttgg atcggcgtgg tggatgttga gtatttaaag aaaattcgtc      1320
cttacgttat cattgggtgt tttgtcgtcg ggatggtcct cacgcctcct gacatttttct     1380 ctcagaccat gttggcggtc ccgatgtggc tgcttttttga aattggcctt ttatttggtc     1440
gtttggttcg taaacgtggt gagcatccag acgaccagcc agcgtctgac ggcgatcagc      1500
cgccagcaac acgtcaataa                                                  1520
```

<210> SEQ ID NO 141
<211> LENGTH: 1736
<212> TYPE: DNA
<213> ORGANISM: Artificial
<220> FEATURE:
<223> OTHER INFORMATION: primer

<400> SEQUENCE: 141

```
atgcacgccc cgtctcctat ggcattactt ttaattgcta tcgtcgttct cgtactcttt      60
gggcgcggca aagtctcatc tctgatgggc gaggtcggca agggtattac agcgtttaag     120
aaaggcgtaa agaaggtgc agaagatatt gacgcggctg ctcattcgga gcctaaagag      180
ctggagcagt tgaaaacagc tgacgatatt gaacgtgcac gtgcagactt ggctgcggaa     240
cgtgcaaagc tggacgcaga gcgtgcacgc acaggggcag attctgccct tcgtgacgtt     300
actcctactg attccacgaa actgtaactt taagaaggag atatacatgt tggatattgg     360
ttggtcagag cttcttctga tcggtgtagt agccctgatc gtgattggtc aaaggaccct     420
cccaaagtta ttccatacgt tagggcgtat taccgcgcgc gctcgctcga tggctcgcga     480
gttttcttcg gcaatggagg acgccgcaaa atcgtctggt cttgacgacg ccgctaagac     540
gctcaaggat gttaacgcgc tttcatcgaa gcgtgcactc gggctcgacg cgctggagcg     600
tgcaaccgaa cgctttgaaa agtgggaccc gcttaaccca aaagatgaag cagggcgcaa     660
ggcacctgtg cctgatccat cagctccgct tccaccgcag cctgctgcaa atggctcgga     720
tgcacctgct gctcctcctg cggatttgcc accagccccg ggggtggctg ctccacctgt     780
cgcagctgag gatgcgctcg acactgcaga gggcgtcgt cgtttgcatg cggttcgtcg      840
tagtgaccgt gcttaacttt aagaaggaga tatacatgaa atccgccaaa ccagatgata     900
ttgacgatac aagtgccccg cttattgagc acctggcaga gttacgtact cgcctgatct     960
ggtcagtact tgctttcgtt gtggcgatgg tattatgcta ctttgtctgg aaccctatct    1020 ttgattttt gactcaacct atttgtcatg cattggaaaa gcgtgatcaa gcctgtggtc    1080
ttattctctt aaagttgcaa gaggggttct ttgtggcgat gcgtattgca ttctttggcg    1140
gctttgtgtt ggcgttcccg gtcgtggggt accagctctg gcgtttcgtc gctccaggtc    1200
tgtatcgtag cgagaagaat gctctgttac catttctggt agcctcaccg gttatgtttc    1260
tgattggtgc tgcctttgca tactacatta tccttccgtg ggctttcgac ttctttctcg    1320
gttttcaaca gggtccggcg gcacagcctg cagatccagc cgccgctgca gcagctggtg    1380
ctgcaggtgc agctggtgcc gaacaaccgt gggccggat cgtattccaa ggctcggtgg     1440
aagagtacct cgctttaacg actaaattca ttctggcgtt cgggctttca ttccaactgc    1500
ctgtcgcatt gactttaatg gggaaggcag gcttagtttc cagtgaaggg ctcgctagtg    1560
tgcgccgtta tgccattgtg gtaattctta tcctcgcagc gatggttacc ccgcctgatg    1620
```

-continued

```
ttatcagcca aatcgtctta ttttctgtca tctatgggct gtatgaagtc tccatctttc    1680
tggtgcgtcg catggagaag aaacgtgagc tggaggagca agaagccgac gtttaa        1736
```